US007288406B2

(12) United States Patent
Bogin et al.

(10) Patent No.: US 7,288,406 B2
(45) Date of Patent: Oct. 30, 2007

(54) ACTIVE VARIANTS OF FGF WITH IMPROVED SPECIFICITY

(75) Inventors: Oren Bogin, Ganei Yohanan (IL); Rivka Adar, Karmei Yosef (IL); Avner Yayon, Moshav Sitria (IL)

(73) Assignee: ProChon Biotech Ltd., Rehovot (IL)

( * ) Notice: Subject to any disclaimer, the term of this patent is extended or adjusted under 35 U.S.C. 154(b) by 508 days.

(21) Appl. No.: 10/424,955

(22) Filed: Apr. 29, 2003

(65) Prior Publication Data

US 2004/0014658 A1 Jan. 22, 2004

Related U.S. Application Data

(63) Continuation of application No. PCT/IL01/00962, filed on Oct. 18, 2001.

(30) Foreign Application Priority Data

Oct. 31, 2000 (IL) .................................... 139380

(51) Int. Cl.

| | |
|---|---|
| ***C07K 14/50*** | (2006.01) |
| ***A61K 38/18*** | (2006.01) |
| ***C12N 15/63*** | (2006.01) |
| ***C12N 15/18*** | (2006.01) |

(52) U.S. Cl. ......................... 435/320.1; 514/2; 514/12; 536/23.4; 536/23.5; 530/350; 530/399

(58) Field of Classification Search ..................... None
See application file for complete search history.

(56) References Cited

U.S. PATENT DOCUMENTS

| | | | | |
|---|---|---|---|---|
| 5,491,220 | A * | 2/1996 | Seddon et al. | 530/399 |
| 5,512,460 | A | 4/1996 | Nauro et al. | |
| 5,571,895 | A | 11/1996 | Kurokawa et al. | |
| 5,622,928 | A | 4/1997 | Naruo et al. | |
| 5,989,866 | A | 11/1999 | Deisher et al. | |
| 5,998,170 | A | 12/1999 | Arakawa et al. | |
| 6,274,712 | B1 | 8/2001 | Springer et al. | |
| 6,294,359 | B1 | 9/2001 | Fiddes et al. | |

FOREIGN PATENT DOCUMENTS

| | | |
|---|---|---|
| WO | WO 01/07595 | 2/2001 |
| WO | WO 01/39788 | 6/2001 |
| WO | WO 02/36732 | 5/2002 |
| WO | WO 02/077199 | 10/2002 |
| WO | WO 2004/069298 | 8/2004 |

OTHER PUBLICATIONS

Cappellen et al., Nature Genet. 23, 18, 1999.
Coughlin et al., J Biol. Chem 263, 988, 1988.
Danilenko et al., Arch. Biochem, Biophys. 1, 361, 1999.
Dvorakova, et al., Br. J. Haematol. 113, 832, 2001.
Faham, et al., Curr. Opin. Struc. Biol. 8, 578, 1998.
Fingl, et al., 1975, The Pharmacological Basis of Therapeutics, Ch. 1, p. 1.
Givol and Yayon, FASEB J. 6, 3369, 1992.
Hecht et al., Acta Crystallogr. D. Biol. Crystallogr. 57, 378, 2001.
Johnson and Williams, Adv. Cancer Res. 60, 1993.
Kirikoshi et al., Biochem Biophys. Res. Commun. 274, 337, 2000.
Kuroda et al., Bone 25, 431, 1999.
Nakatake et al., Biochem Biophys. Acta. 1517, 460, 2001.
Nishimura et al., Biochem. Biophys. Acta. 1492, 203, 2000.
Ornitz, Bioessays 22, 108, 2000.
Ornitz et al., J. Biol. Chem. 271, 15292, 1996.
Ornitz and Itoh, Gen. Biol. 2, 320005.1, 2001.
Pellegrini et al., Nature 407, 1029, 2000.
Pillai and Panchagnula, Curr. Opin. Chem. Biol. 5, 477, 2001.
Plotnikov et al., Cell 98, 641, 1999.
Plotnikov et al., Cell 101, 413, 2000.
Sahni, M. et al., Genes Devel. 13, 1361, 1999.
Schlessinger et al., Mol. Cell. 6, 43, 2000.
Seno et al., Eur. J. Biochem. 188, 239, 1990.
Sleeman et al., Gene 271, 171, 2001.
Stauber et al., PNAS USA 97, 49, 2000.
Vajo et al., Endocrine Rev. 21, 23, 2000.
Yamashita et al., Biochem Biophys. REs. Commun. 277, 494, 2000.
Yayon et al., Cell 64, 841, 1991.
Yee et al., J. Natl. Cancer 92, 1848, 2000.
Zhu et al., Protein Eng. 10, 417, 1997.
Arakawa T, Horan TP, Narhi LO, Rees DC, Schiffer SG, Holst PL, Prestrelski SJ, Tsai LB, Fox GM. Production and characterization of an analog of acidic fibroblast growth factor with enhanced stability and biological activity. Protein Eng. 1993 6(5):541-6.
Springer BA, Pantoliano MW, Barbera FA, Gunyuzlu PL, Thompson LD, Herblin WF, Rosenfeld SA, Book GW. Identification and concerted function of two receptor binding surfaces on basic fibroblast growth factor required for mitogenesis. J Biol Chem. 1994 269(43):26879-84.

* cited by examiner

*Primary Examiner*—Christine J. Saoud
(74) *Attorney, Agent, or Firm*—Winston & Strawn LLP

(57) ABSTRACT

The present invention provides active fibroblast growth factor variants demonstrating enhanced receptor subtype specificity. The preferred novel variants retain binding to FGF Receptor Type 3 (FGFR3) triggering intracellular downstream mechanisms leading to activation of a biological response. Methods of utilizing preferred FGF mutants in preparation of medicaments for the treatment of malignancies and skeletal disorders including osteoporosis and enhancing fracture healing and wound healing processes are provided.

22 Claims, 13 Drawing Sheets

Figure 1A

```
LYCSN---------GGHFLRILPDGTVDGTRDRSDQHIQLQLSAESVG-EVYIKSTETGQYLAMDTDGLLYGSQTPNEE-| FGF1-HUM
LYCKN---------GGFFLRIHPDGRVDGVREKSDPHIKLQLQAEERG-VVSIKGVCANRYLAMKEDGRLLASKCVTDE-| FGF2-HUM
LGGAPRRRKLYC--ATKYHLQLHPSGRVNGSLEN-SAYSILEITAVEVG-GVAIRGLFSGRYLAMNKRGRLYASEHYSAE-| FGF3-HUM
LLGIKRLRRLYCNVGIGFHLQALPDGRIGGAHAD-TRDSLLELSPVERG-VVSIFGVASRFFVAMSSKGKLYGSPFFTDE-| FGF4-HUM
SPSGRRTGSLYCRVGIGFHLQIYPDGKVNGSHEA-NMLSVLEIFAVSQG-IVGIRGVFSNKFLAMSKKGKLHASAKFTDD-| FGF5-HUM
LYCNVG--------IGFHLQVLPDGRISGTHEE-NPYSLLEISTVERG-VVSLFGVRSALFVAMNSKGRLYATPSFQEE-| FGF6-HUM
EGGDIRVRRLFC--RTQWYLRIDKRGKVKGTQEMKNNYNIMEIRTVAVG-IVAIKGVESEFYLAMNKEGKLYAKKECNED-| FGF7-HUM
RRLIRTYQLYSR--TSGKHVQVLANKRINAMAEDGDPFAKLIVETDTFGSRVRVRGAETGLYICMNKKGKLIAKSNGKGKD| FGF8-HUM
LKGILRRRQLYC--RTGFHLEIFPNGTIQGTRKDHSRFGILEFISIAVG-LVSIRGVDSGLYLGMNEKGELYGSEKLTQE-| FGF9-HUM
GKITRL-QYLYSAGPYGFHLEIFPNGTIQGTRKDHSRFGILEFISIAVG-LVSIRGVDSGLYLGMNEKGELYGSEKLTQE-| FGF9-MUS
LQGDVRWRKLFS--FTKYFLKIEKNGKVSGTKKENCPYSILEITSVEIG-VVAVKAINSNYYLAMNKKGKLYGSKEFNND-| FGF10-HUM
LKGIVT--KLFC--RQGFYLQANPDGSIQGTPEDTSSFTHFNLIPVGLR-VVTIQSAKLGHYMAMNAEGLLYSSPHFTAE-| FGF11-HUM
LKGIVT--RLFS--QQGYFLQMHPDGTIDGTKDENSDYTLFNLIPVGLR-VVAIQGVKASLYVAMNGEGYLYSSDVFTPE-| FGF12-HUM
LKGIVT--KLYS--RQGYHLQLQADGTIDGTKDEDSTYTLFNLIPVGLR-VVAIQGVQTKLYLAMNSEGYLYTSELFTPE-| FGF13-HUM
LKGIVT--RLFC--RQGYYLQMHPDGALDGTKDDSTNSTLFNLIPVGLR-VVAIQGVKTGLYIAMNGEGYLYPSELFTPE-| FGF14-HUM
LQYLYSAGPY----VSNCFLRIRSDGSVDCEEDQ-NERNLLEFRAVALK-TIAIKDVSSVRYLCMSADGKIYGLIRYSEED| FGF15-HUM
LKGILRRRQLYC--RTGFHLEIFPNGTVHGTRHDHSRFGILEFISLAVG-LISIRGVDSGLYLGMNERGELYGSKKLTRE-| FGF16-HUM
RRQIREYQLYSR--TSGKHVQVTG-RRISATAEDGNKFAKLIVETDTFGSRVRIKGAESEKYICMNKRGKLIGKPSGKSKD| FGF17-HUM
RKQLRLYQLYSR--TSGKHIQVLG-RRISARGEDGDKYAQLLVETDTFGSQVRIKGKETEFYLCMNRKGKLVGKPDGTSKE| FGF18-HUM
LRHLYTSGPHG---LSSCFLRIRADGVVDCARGQ-SAHSLLEIKAVALR-TVAIKGVHSVRYLCMGADGKMQGLLQYSEED| FGF19-HUM
LHGILRRRQLYC--RTGFHLQILPDGSVQGTRQDHSLFGILEFISVAVG-LVSIRGVDSGLYLGMNDKGELYGSEKLTSE-| FGF20-HUM
RQRYLYTDDAQ---QTEAHLEIREDGTVGGAAD-QSPESLLQLKALKPG-VIQILGVKTSRFLCQRPDGALYGSLHFDPEA| FGF21-HUM
LEGDVRWRRLFS--STHFFLRVDPGGRVQGTRWRHGQDSILEIRSVHVG-VVVIKAVSSGFYVAMNRRGRLYGSRLYTVD-| FGF22-HUM
LYTATAR-------NSYHLQIHKNGHVDGAPHQ-TIYSALMIRSEDAG-FVVITGVMSRRYLCMDFRGNIFGSHYFDPEN| FGF23-HUM
```

Figure 1B

```
CLFLERLEENHYNTYISKKH----------A----EKN--------WFVGLKKNGSCKR--GPRTHYGQKAILFLPLP | FGF1-HUM
CFFFERLESNNYNTYRSRK----------------YTS--------WYVALKRTGQYKL--GSKTGPGQKAILFLPMS | FGF2-HUM
CEFVERIHELGYNTYASRLYRTVSSTPGARRQPSAERL--------WYVSVNGKGRPRR--GFKTRRTQKSSLFLPRV | FGF3-HUM
CTFKEILLPNNYNAYESYKYP---------------G---------MFIALSKNGKTKK--GNRVSPTMKVTHFLPRL | FGF4-HUM
CKFRERFQENSYNTYASAIHR----------TEKTGRE--------WYVALNKRGKAKRGCSPRVKPQHISTHFLPRF | FGF5-HUM
CKFRETLLPNNYNAYESDLYQ-------------------------GTYIALSKYGRVR--GSKVSPIMTVTHFLPRI | FGF6-HUM
CNFKELILENHYNTYASAKW----------THNG-GE---------MFVALNQKGIPVR--GKKTKKEQKTAHFLPMA | FGF7-HUM
CVFTEIVLENNYTALQNAKY----------EG--------------WYMAFTRKGRPRK--GSKTRQHQREVHFMKRL | FGF8-HUM
CVFREQFEENWYNTYSSNLY----------KHVDTGRR--------YYVALNKDGTPRE--GTRTKRHQKFTHFLPRP | FGF9-HUM
CVFREQFEENWYNTYSSNLY----------KHVDTGRR--------YYVALNKDGTPRE--GTRTKRHQKFTHFLPRP | FGF9-MUS
CKLKERIEENGYNTYASFNW----------QHNG-RQ---------MYVALNGKGAPRR--GQKTRRKNTSAHFLPMV | FGF10-HUM
CRFKECVFENYYVLYASALY----------RQRRSGRA--------WYLGLDKEGQVMK--GNRVKKTKAAAHFLPKL | FGF11-HUM
CKFKESVFENYYVIYSSTLY----------RQQESGRA--------WFLGLNKEGQIMK--GNRVEKTKPSSHFVPKP | FGF12-HUM
CKFKESVFENYYVTYSSMIY----------RQQQSGRG--------WYLGLNKEGEIMK--GNHVKKNKPAAHFLPKP | FGF13-HUM
CKFKESVFENYYVIYSSMLY----------RQQESGRA--------WFLGLNKEGQAMK--GNRVKKTKPAAHFLPKP | FGF14-HUM
CTFREEMDCLGYNQYRSMK---------------  HH--------LHIIFIQAKP-RE--QLQDQ---KPSNFIPVF | FGF15-HUM
CVFREQFEENWYNTYASTLY----------KHSDSERQ--------YYVALNKDGSPRE--GYRTKRHQKFTHFLPRP | FGF16-HUM
CVFTEIVLENNYTAFQNARH----------EG--------------WFMAFTRQGRPRQ--ASRSRQNQREAHFIKRL | FGF17-HUM
CVFIEKVLENNYTALMSAKY----------SG--------------WYVGFTKKGRPRK--GPKTRENQQDVHFMKRY | FGF18-HUM
CAFEEEIRPDGYNVYRSEK-----------------HR--------LPVSLSSAKQ-RQ--LYKNRGFLPLSHFLPML | FGF19-HUM
CIFREQFEENWYNTYSSNIY----------KHGDTGRR--------YFVALNKDGTPRD--GARSKRHQKFTHFLPRP | FGF20-HUM
CSFRELLLEDGYNVYQSEAH---------------GL---------PLHLPGNKSPHRD--PAPRG----PARFLPLP | FGF21-HUM
CRFRERIEENGHNTYASQRW----------RRRG-QP---------MFLALDRRGGPRP--GGRTRRYHLSAHFLPVL | FGF22-HUM
CRFQHQTLENGYDVYHSPQYHFLVSLGRAKRAFLPGMNPPPYSQFLSRRNEIPLIHFNTPIPRRHTRSAEDDSERDPL | FGF23-HUM
```

Lane 1, Molecular weight markers [Lysozyme (20.7kDa),Soybean trypsin inhibitor (28.8kDa), Carbonic anhydrase (34.3kDa), Ovalbumin (50kDa)];
Lane 2 FGF-9 (control)
Lane 3 L37M-FGF9
Lane 4 L45M-FGF9
Lane 5 R64M-FGF9
Lane 6 FGF-9-2

Western analysis of JNK activation by FGF variants on RCS cells

αR: antibody specific for the respective FGFR types:
R1, R2, R3: FGFR1, FGFR2, FGFR3
αJNK: antibody specific for activated Jun Kinase
FGF9: native FGF9
L37M: L37M-FGF9 variant
W144G: L37M-W144G-FGF9 variant
W144R: L37M-W144R-FGF9 variant Figure 9
Effect of L37M-W144G-FGF9 on Bone Fracture Healing
A. Autoradiograph of rabbit ulnas that had undergone an Osteotomy.
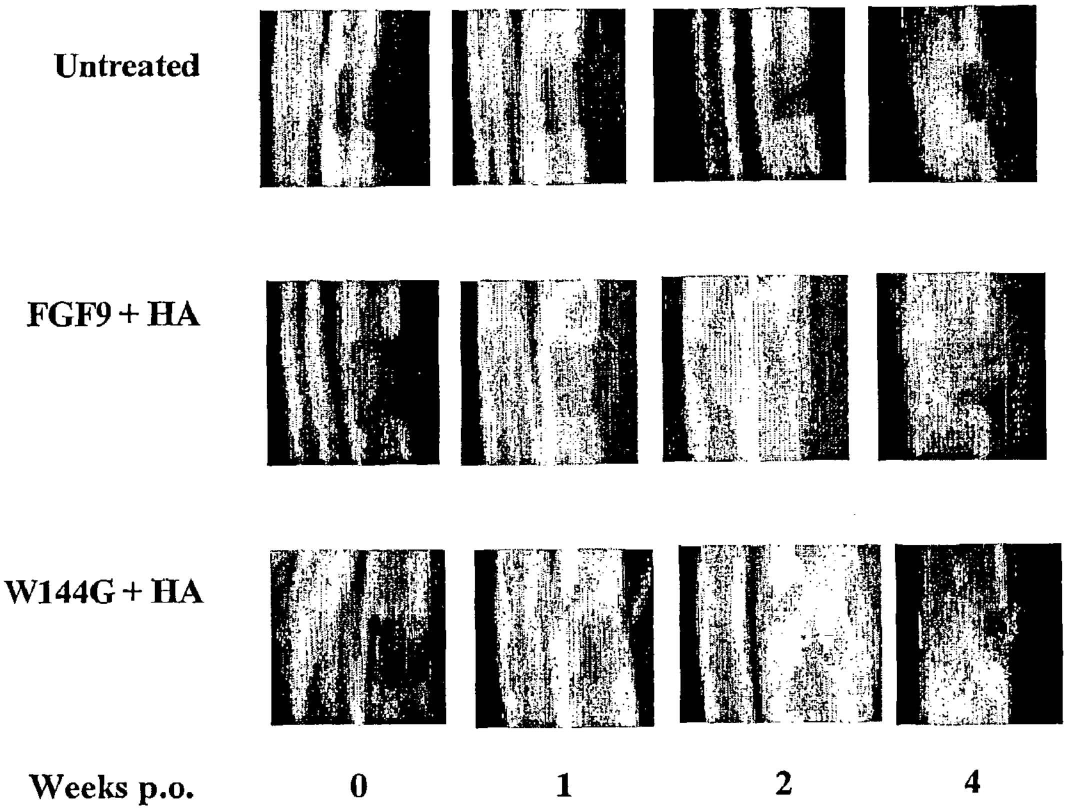
B. Effect of L37M-W144G- FGF9 on Bone Mineral Density (4 weeks p.o.)
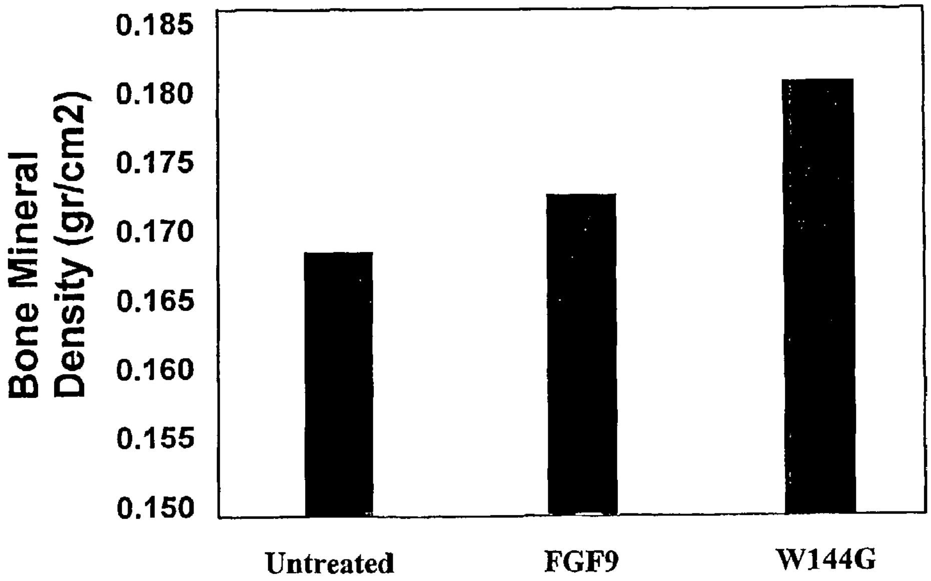

SEQUENCE LISTING

```
<160> NUMBER OF SEQ ID NOS: 80

<210> SEQ ID NO 1
<211> LENGTH: 208
<212> TYPE: PRT
<213> ORGANISM: Homo sapiens
<220> FEATURE:
<221> NAME/KEY: MISC_FEATURE
<222> LOCATION: (144)..(144)
<223> OTHER INFORMATION: X IS OTHER THAN W AND MORE PREFERABLY SELECTED
      FROM: G, R, E, V

<400> SEQUENCE: 1

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
```

-continued

```
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Xaa
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205


<210> SEQ ID NO 2
<211> LENGTH: 172
<212> TYPE: PRT
<213> ORGANISM: Homo sapiens
<220> FEATURE:
<221> NAME/KEY: MISC_FEATURE
<222> LOCATION: (108)..(108)
<223> OTHER INFORMATION: X IS OTHER THAN W AND MORE PREFERABLY SELECTED
      FROM G, R, E, V

<400> SEQUENCE: 2

Met Gly Gln Ser Glu Ala Gly Gly Leu Pro Arg Gly Pro Ala Val Thr
1               5                   10                  15

Asp Leu Asp His Leu Lys Gly Ile Leu Arg Arg Arg Gln Leu Tyr Cys
            20                  25                  30

Arg Thr Gly Phe His Leu Glu Ile Phe Pro Asn Gly Thr Ile Gln Gly
        35                  40                  45

Thr Arg Lys Asp His Ser Arg Phe Gly Ile Leu Glu Phe Ile Ser Ile
    50                  55                  60

Ala Val Gly Leu Val Ser Ile Arg Gly Val Asp Ser Gly Leu Tyr Leu
65                  70                  75                  80

Gly Met Asn Glu Lys Gly Glu Leu Tyr Gly Ser Glu Lys Leu Thr Gln
                85                  90                  95

Glu Cys Val Phe Arg Glu Gln Phe Glu Glu Asn Xaa Tyr Asn Thr Tyr
            100                 105                 110

Ser Ser Asn Leu Tyr Lys His Val Asp Thr Gly Arg Arg Tyr Tyr Val
        115                 120                 125

Ala Leu Asn Lys Asp Gly Thr Pro Arg Glu Gly Thr Arg Thr Lys Arg
    130                 135                 140

His Gln Lys Phe Thr His Phe Leu Pro Arg Pro Val Asp Pro Asp Lys
145                 150                 155                 160

Val Pro Glu Leu Tyr Lys Asp Ile Leu Ser Gln Ser
                165                 170


<210> SEQ ID NO 3
<211> LENGTH: 208
<212> TYPE: PRT
<213> ORGANISM: Homo sapiens
<220> FEATURE:
<221> NAME/KEY: MISC_FEATURE
```

-continued

<222> LOCATION: (143)..(143)
<223> OTHER INFORMATION: X IS OTHER THAN N AND MORE PREFERABLY S

<400> SEQUENCE: 3

```
Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Xaa Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 4
<211> LENGTH: 172
<212> TYPE: PRT
<213> ORGANISM: Homo sapiens
<220> FEATURE:
<221> NAME/KEY: MISC_FEATURE
<222> LOCATION: (107)..(107)
<223> OTHER INFORMATION: X IS OTHER THAN N AND MORE PREFERABLY S

<400> SEQUENCE: 4

```
Met Gly Gln Ser Glu Ala Gly Gly Leu Pro Arg Gly Pro Ala Val Thr
1               5                   10                  15

Asp Leu Asp His Leu Lys Gly Ile Leu Arg Arg Arg Gln Leu Tyr Cys
            20                  25                  30

Arg Thr Gly Phe His Leu Glu Ile Phe Pro Asn Gly Thr Ile Gln Gly
        35                  40                  45

Thr Arg Lys Asp His Ser Arg Phe Gly Ile Leu Glu Phe Ile Ser Ile
    50                  55                  60

Ala Val Gly Leu Val Ser Ile Arg Gly Val Asp Ser Gly Leu Tyr Leu
65                  70                  75                  80

Gly Met Asn Glu Lys Gly Glu Leu Tyr Gly Ser Glu Lys Leu Thr Gln
                85                  90                  95

Glu Cys Val Phe Arg Glu Gln Phe Glu Glu Xaa Trp Tyr Asn Thr Tyr
            100                 105                 110

Ser Ser Asn Leu Tyr Lys His Val Asp Thr Gly Arg Arg Tyr Tyr Val
        115                 120                 125
```

-continued

```
Ala Leu Asn Lys Asp Gly Thr Pro Arg Glu Gly Thr Arg Thr Lys Arg
    130                 135                 140

His Gln Lys Phe Thr His Phe Leu Pro Arg Pro Val Asp Pro Asp Lys
145                 150                 155                 160

Val Pro Glu Leu Tyr Lys Asp Ile Leu Ser Gln Ser
                165                 170


<210> SEQ ID NO 5
<211> LENGTH: 145
<212> TYPE: PRT
<213> ORGANISM: Homo sapiens

<400> SEQUENCE: 5

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg Pro
        115                 120                 125

Val Asp Pro Asp Lys Val Pro Glu Leu Tyr Lys Asp Ile Leu Ser Gln
    130                 135                 140

Ser
145


<210> SEQ ID NO 6
<211> LENGTH: 164
<212> TYPE: PRT
<213> ORGANISM: Homo sapiens

<400> SEQUENCE: 6

Met Pro Arg Gly Pro Ala Val Thr Asp Leu Asp His Leu Lys Gly Ile
1               5                   10                  15

Leu Arg Arg Arg Gln Leu Tyr Cys Arg Thr Gly Phe His Leu Glu Ile
            20                  25                  30

Phe Pro Asn Gly Thr Ile Gln Gly Thr Arg Lys Asp His Ser Arg Phe
        35                  40                  45

Gly Ile Leu Glu Phe Ile Ser Ile Ala Val Gly Leu Val Ser Ile Arg
    50                  55                  60

Gly Val Asp Ser Gly Leu Tyr Leu Gly Met Asn Glu Lys Gly Glu Leu
65                  70                  75                  80

Tyr Gly Ser Glu Lys Leu Thr Gln Glu Cys Val Phe Arg Glu Gln Phe
                85                  90                  95

Glu Glu Asn Trp Tyr Asn Thr Tyr Ser Ser Asn Leu Tyr Lys His Val
            100                 105                 110

Asp Thr Gly Arg Arg Tyr Tyr Val Ala Leu Asn Lys Asp Gly Thr Pro
        115                 120                 125
```

-continued

Arg Glu Gly Thr Arg Thr Lys Arg His Gln Lys Phe Thr His Phe Leu
130 135 140

Pro Arg Pro Val Asp Pro Asp Lys Val Pro Glu Leu Tyr Lys Asp Ile
145 150 155 160

Leu Ser Gln Ser

<210> SEQ ID NO 7
<211> LENGTH: 172
<212> TYPE: PRT
<213> ORGANISM: Homo sapiens

<400> SEQUENCE: 7

Met Gly Gln Ser Glu Ala Gly Gly Leu Pro Arg Gly Pro Ala Val Thr
1 5 10 15

Asp Leu Asp His Leu Lys Gly Ile Leu Arg Arg Arg Gln Leu Tyr Cys
20 25 30

Arg Thr Gly Phe His Leu Glu Ile Phe Pro Asn Gly Thr Ile Gln Gly
35 40 45

Thr Arg Lys Asp His Ser Arg Phe Gly Ile Leu Glu Phe Ile Ser Ile
50 55 60

Ala Val Gly Leu Val Ser Ile Arg Gly Val Asp Ser Gly Leu Tyr Leu
65 70 75 80

Gly Met Asn Glu Lys Gly Glu Leu Tyr Gly Ser Glu Lys Leu Thr Gln
85 90 95

Glu Cys Val Phe Arg Glu Gln Phe Glu Glu Asn Trp Tyr Asn Thr Tyr
100 105 110

Ser Ser Asn Leu Tyr Lys His Val Asp Thr Gly Arg Arg Tyr Tyr Val
115 120 125

Ala Leu Asn Lys Asp Gly Thr Pro Arg Glu Gly Thr Arg Thr Lys Arg
130 135 140

His Gln Lys Phe Thr His Phe Leu Pro Arg Pro Val Asp Pro Asp Lys
145 150 155 160

Val Pro Glu Leu Tyr Lys Asp Ile Leu Ser Gln Ser
165 170

<210> SEQ ID NO 8
<211> LENGTH: 161
<212> TYPE: PRT
<213> ORGANISM: Homo sapiens

<400> SEQUENCE: 8

His His His His His His Ser Ser Gly Leu Val Pro Arg Gly Ser His
1 5 10 15

Met Gln Leu Tyr Cys Arg Thr Gly Phe His Leu Glu Ile Phe Pro Asn
20 25 30

Gly Thr Ile Gln Gly Thr Arg Lys Asp His Ser Arg Phe Gly Ile Leu
35 40 45

Glu Phe Ile Ser Ile Ala Val Gly Leu Val Ser Ile Arg Gly Val Asp
50 55 60

Ser Gly Leu Tyr Leu Gly Met Asn Glu Lys Gly Glu Leu Tyr Gly Ser
65 70 75 80

Glu Lys Leu Thr Gln Glu Cys Val Phe Arg Glu Gln Phe Glu Glu Asn
85 90 95

Trp Tyr Asn Thr Tyr Ser Ser Asn Leu Tyr Lys His Val Asp Thr Gly
100 105 110

-continued

```
Arg Arg Tyr Tyr Val Ala Leu Asn Lys Asp Gly Thr Pro Arg Glu Gly
        115                 120                 125

Thr Arg Thr Lys Arg His Gln Lys Phe Thr His Phe Leu Pro Arg Pro
    130                 135                 140

Val Asp Pro Asp Lys Val Pro Glu Leu Tyr Lys Asp Ile Leu Ser Gln
145                 150                 155                 160

Ser


<210> SEQ ID NO 9
<211> LENGTH: 127
<212> TYPE: PRT
<213> ORGANISM: Homo sapiens

<400> SEQUENCE: 9

Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu Pro Arg
        115                 120                 125


<210> SEQ ID NO 10
<211> LENGTH: 117
<212> TYPE: PRT
<213> ORGANISM: Homo sapiens

<400> SEQUENCE: 10

Met His Leu Glu Ile Phe Pro Asn Gly Thr Ile Gln Gly Thr Arg Lys
1               5                   10                  15

Asp His Ser Arg Phe Gly Ile Leu Glu Phe Ile Ser Ile Ala Val Gly
            20                  25                  30

Leu Val Ser Ile Arg Gly Val Asp Ser Gly Leu Tyr Leu Gly Met Asn
        35                  40                  45

Glu Lys Gly Glu Leu Tyr Gly Ser Glu Lys Leu Thr Gln Glu Cys Val
    50                  55                  60

Phe Arg Glu Gln Phe Glu Glu Asn Trp Tyr Asn Thr Tyr Ser Ser Asn
65                  70                  75                  80

Leu Tyr Lys His Val Asp Thr Gly Arg Arg Tyr Tyr Val Ala Leu Asn
                85                  90                  95

Lys Asp Gly Thr Pro Arg Glu Gly Thr Arg Thr Lys Arg His Gln Lys
            100                 105                 110

Phe Thr His Phe Leu
        115


<210> SEQ ID NO 11
<211> LENGTH: 119
<212> TYPE: PRT
```

-continued

<213> ORGANISM: Homo sapiens

<400> SEQUENCE: 11

```
Met His Leu Glu Ile Phe Pro Asn Gly Thr Ile Gln Gly Thr Arg Lys
1               5                   10                  15

Asp His Ser Arg Phe Gly Ile Leu Glu Phe Ile Ser Ile Ala Val Gly
            20                  25                  30

Leu Val Ser Ile Arg Gly Val Asp Ser Gly Leu Tyr Leu Gly Met Asn
        35                  40                  45

Glu Lys Gly Glu Leu Tyr Gly Ser Glu Lys Leu Thr Gln Glu Cys Val
    50                  55                  60

Phe Arg Glu Gln Phe Glu Glu Asn Trp Tyr Asn Thr Tyr Ser Ser Asn
65                  70                  75                  80

Leu Tyr Lys His Val Asp Thr Gly Arg Arg Tyr Tyr Val Ala Leu Asn
                85                  90                  95

Lys Asp Gly Thr Pro Arg Glu Gly Thr Arg Thr Lys Arg His Gln Lys
            100                 105                 110

Phe Thr His Phe Leu Pro Arg
        115
```

<210> SEQ ID NO 12
<211> LENGTH: 125
<212> TYPE: PRT
<213> ORGANISM: Homo sapiens

<400> SEQUENCE: 12

```
Met Gln Leu Tyr Cys Arg Thr Gly Phe His Leu Glu Ile Phe Pro Asn
1               5                   10                  15

Gly Thr Ile Gln Gly Thr Arg Lys Asp His Ser Arg Phe Gly Ile Leu
            20                  25                  30

Glu Phe Ile Ser Ile Ala Val Gly Leu Val Ser Ile Arg Gly Val Asp
        35                  40                  45

Ser Gly Leu Tyr Leu Gly Met Asn Glu Lys Gly Glu Leu Tyr Gly Ser
    50                  55                  60

Glu Lys Leu Thr Gln Glu Cys Val Phe Arg Glu Gln Phe Glu Glu Asn
65                  70                  75                  80

Trp Tyr Asn Thr Tyr Ser Ser Asn Leu Tyr Lys His Val Asp Thr Gly
                85                  90                  95

Arg Arg Tyr Tyr Val Ala Leu Asn Lys Asp Gly Thr Pro Arg Glu Gly
            100                 105                 110

Thr Arg Thr Lys Arg His Gln Lys Phe Thr His Phe Leu
        115                 120                 125
```

<210> SEQ ID NO 13
<211> LENGTH: 125
<212> TYPE: PRT
<213> ORGANISM: Homo sapiens

<400> SEQUENCE: 13

```
Met Tyr Cys Arg Thr Gly Phe His Leu Glu Ile Phe Pro Asn Gly Thr
1               5                   10                  15

Ile Gln Gly Thr Arg Lys Asp His Ser Arg Phe Gly Ile Leu Glu Phe
            20                  25                  30

Ile Ser Ile Ala Val Gly Leu Val Ser Ile Arg Gly Val Asp Ser Gly
        35                  40                  45

Leu Tyr Leu Gly Met Asn Glu Lys Gly Glu Leu Tyr Gly Ser Glu Lys
    50                  55                  60
```

-continued

```
Leu Thr Gln Glu Cys Val Phe Arg Glu Gln Phe Glu Glu Asn Trp Tyr
65                  70                  75                  80

Asn Thr Tyr Ser Ser Asn Leu Tyr Lys His Val Asp Thr Gly Arg Arg
                85                  90                  95

Tyr Tyr Val Ala Leu Asn Lys Asp Gly Thr Pro Arg Glu Gly Thr Arg
            100                 105                 110

Thr Lys Arg His Gln Lys Phe Thr His Phe Leu Pro Arg
        115                 120                 125
```

<210> SEQ ID NO 14
<211> LENGTH: 627
<212> TYPE: DNA
<213> ORGANISM: Homo sapiens
<220> FEATURE:
<221> NAME/KEY: misc_feature
<222> LOCATION: (430)..(432)
<223> OTHER INFORMATION: nnn is other than tgg, taa, tag or tga.

<400> SEQUENCE: 14

```
atggctccct taggtgaagt tgggaactat ttcggtgtgc aggatgcggt accgtttggg     60

aatgtgcccg tgttgccggt ggacagcccg gttttgttaa gtgaccacct gggtcagtcc    120

gaagcagggg ggctccccag gggacccgca gtcacggact tggatcattt aaaggggatt    180

ctcaggcgga ggcagctata ctgcaggact ggatttcact tagaaatctt ccccaatggt    240

actatccagg gaaccaggaa agaccacagc cgatttggca ttctggaatt tatcagtata    300

gcagtgggcc tggtcagcat tcgaggcgtg gacagtggac tctacctcgg gatgaatgag    360

aaggggagc tgtatggatc agaaaaacta acccaagagt gtgtattcag agaacagttc    420

gaagaaaacn nntataatac gtactcgtca aacctatata agcacgtgga cactggaagg    480

cgatactatg ttgcattaaa taaagatggg accccgagag aagggactag gactaaacgg    540

caccagaaat tcacacattt tttacctaga ccagtggacc ccgacaaagt acctgaactg    600

tataaggata ttctaagcca aagttga                                        627
```

<210> SEQ ID NO 15
<211> LENGTH: 519
<212> TYPE: DNA
<213> ORGANISM: Homo sapiens
<220> FEATURE:
<221> NAME/KEY: misc_feature
<222> LOCATION: (322)..(324)
<223> OTHER INFORMATION: nnn IS OTHER THAN tgg, taa, tag OR tga

<400> SEQUENCE: 15

```
atgggtcagt ccgaagcagg ggggctcccc aggggacccg cagtcacgga cttggatcat     60

ttaaagggga ttctcaggcg gaggcagcta tactgcagga ctggatttca cttagaaatc    120

ttccccaatg gtactatcca gggaaccagg aaagaccaca gccgatttgg cattctggaa    180

tttatcagta tagcagtggg cctggtcagc attcgaggcg tggacagtgg actctacctc    240

gggatgaatg agaaggggga gctgtatgga tcagaaaaac taacccaaga gtgtgtattc    300

agagaacagt tcgaagaaaa cnnntataat acgtactcgt caaacctata taagcacgtg    360

gacactggaa ggcgatacta tgttgcatta aataaagatg ggaccccgag agaagggact    420

aggactaaac ggcaccagaa attcacacat tttttaccta gaccagtgga ccccgacaaa    480

gtacctgaac tgtataagga tattctaagc caaagttga                          519
```

<210> SEQ ID NO 16

-continued

<211> LENGTH: 627
<212> TYPE: DNA
<213> ORGANISM: Homo sapiens
<220> FEATURE:
<221> NAME/KEY: misc_feature
<222> LOCATION: (427)..(429)
<223> OTHER INFORMATION: nnn IS OTHER THAN aac, aat, taa, tag OR tga

<400> SEQUENCE: 16
atggctccct taggtgaagt tgggaactat ttcggtgtgc aggatgcggt accgtttggg 60
aatgtgcccg tgttgccggt ggacagcccg gttttgttaa gtgaccacct gggtcagtcc 120
gaagcagggg ggctccccag gggacccgca gtcacggact tggatcattt aaaggggatt 180
ctcaggcgga ggcagctata ctgcaggact ggatttcact tagaaatctt ccccaatggt 240
actatccagg gaaccaggaa agaccacagc cgatttggca ttctggaatt tatcagtata 300
gcagtgggcc tggtcagcat tcgaggcgtg gacagtggac tctacctcgg gatgaatgag 360
aagggggagc tgtatggatc agaaaaacta acccaagagt gtgtattcag agaacagttc 420
gaagaannnt ggtataatac gtactcgtca aacctatata agcacgtgga cactggaagg 480
cgatactatg ttgcattaaa taaagatggg accccgagag aagggactag gactaaacgg 540
caccagaaat tcacacattt tttacctaga ccagtggacc ccgacaaagt acctgaactg 600
tataaggata ttctaagcca aagttga 627

<210> SEQ ID NO 17
<211> LENGTH: 519
<212> TYPE: DNA
<213> ORGANISM: Homo sapiens
<220> FEATURE:
<221> NAME/KEY: misc_feature
<222> LOCATION: (319)..(321)
<223> OTHER INFORMATION: nnn IS OTHER THAN aac,aat, taa, tag OR tga

<400> SEQUENCE: 17
atgggtcagt ccgaagcagg ggggctcccc aggggacccg cagtcacgga cttggatcat 60
ttaaagggga ttctcaggcg gaggcagcta tactgcagga ctggatttca cttagaaatc 120
ttccccaatg gtactatcca gggaaccagg aaagaccaca gccgatttgg cattctggaa 180
tttatcagta tagcagtggg cctggtcagc attcgaggcg tggacagtgg actctacctc 240
gggatgaatg agaaggggga gctgtatgga tcagaaaaac taacccaaga gtgtgtattc 300
agagaacagt tcgaagaann ngggtataat acgtactcgt caaacctata taagcacgtg 360
gacactggaa ggcgatacta tgttgcatta aataaagatg ggaccccgag agaagggact 420
aggactaaac ggcaccagaa attcacacat tttttaccta gaccagtgga ccccgacaaa 480
gtacctgaac tgtataagga tattctaagc caaagttga 519

<210> SEQ ID NO 18
<211> LENGTH: 438
<212> TYPE: DNA
<213> ORGANISM: Homo sapiens

<400> SEQUENCE: 18
atgcagctat actgcaggac tggatttcac ttagaaatct tccccaatgg tactatccag 60
ggaaccagga aagaccacag ccgatttggc attctggaat ttatcagtat agcagtgggc 120
ctggtcagca ttcgaggcgt ggacagtgga ctctacctcg ggatgaatga gaagggggag 180
ctgtatggat cagaaaaact aacccaagag tgtgtattca gagaacagtt cgaagaaaac 240
tggtataata cgtactcgtc aaacctatat aagcacgtgg acactggaag gcgatactat 300

-continued

```
gttgcattaa ataaagatgg gaccccgaga gaagggacta ggactaaacg gcaccagaaa    360

ttcacacatt ttttacctag accagtggac cccgacaaag tacctgaact gtataaggat    420

attctaagcc aaagttga                                                  438
```

<210> SEQ ID NO 19
<211> LENGTH: 495
<212> TYPE: DNA
<213> ORGANISM: Homo sapiens

<400> SEQUENCE: 19

```
atgcccaggg gacccgcagt cacggacttg gatcatttaa aggggattct caggcggagg     60

cagctatact gcaggactgg atttcactta gaaatcttcc ccaatggtac tatccaggga    120

accaggaaag accacagccg atttggcatt ctggaattta tcagtatagc agtgggcctg    180

gtcagcattc gaggcgtgga cagtggactc tacctcggga tgaatgagaa gggggagctg    240

tatggatcag aaaaactaac ccaagagtgt gtattcagag aacagttcga agaaaactgg    300

tataatacgt actcgtcaaa cctatataag cacgtggaca ctggaaggcg atactatgtt    360

gcattaaata aagatgggac cccgagagaa gggactagga ctaaacggca ccagaaattc    420

acacattttt tacctagacc agtggacccc gacaaagtac ctgaactgta taaggatatt    480

ctaagccaaa gttga                                                     495
```

<210> SEQ ID NO 20
<211> LENGTH: 519
<212> TYPE: DNA
<213> ORGANISM: Homo sapiens

<400> SEQUENCE: 20

```
atgggtcagt ccgaagcagg ggggctcccc aggggacccg cagtcacgga cttggatcat     60

ttaaagggga ttctcaggcg gaggcagcta tactgcagga ctggatttca cttagaaatc    120

ttccccaatg gtactatcca gggaaccagg aaagaccaca gccgatttgg cattctggaa    180

tttatcagta tagcagtggg cctggtcagc attcgaggcg tggacagtgg actctacctc    240

gggatgaatg agaaggggga gctgtatgga tcagaaaaac taacccaaga gtgtgtattc    300

agagaacagt tcgaagaaaa ctggtataat acgtactcgt caaacctata taagcacgtg    360

gacactggaa ggcgatacta tgttgcatta aataaagatg ggaccccgag agaagggact    420

aggactaaac ggcaccagaa attcacacat tttttaccta gaccagtgga ccccgacaaa    480

gtacctgaac tgtataagga tattctaagc caaagttga                           519
```

<210> SEQ ID NO 21
<211> LENGTH: 486
<212> TYPE: DNA
<213> ORGANISM: Homo sapiens

<400> SEQUENCE: 21

```
catcatcatc atcatcacag cagcggcctg gtgccgcgcg gcagccatat gcagctatac     60

tgcaggactg gatttcactt agaaatcttc cccaatggta ctatccaggg aaccaggaaa    120

gaccacagcc gatttggcat tctggaattt atcagtatag cagtgggcct ggtcagcatt    180

cgaggcgtgg acagtggact ctacctcggg atgaatgaga agggggagct gtatggatca    240

gaaaaactaa cccaagagtg tgtattcaga gaacagttcg aagaaaactg gtataatacg    300

tactcgtcaa acctatataa gcacgtggac actggaaggc gatactatgt tgcattaaat    360
```

-continued aaagatggga ccccgagaga agggactagg actaaacggc accagaaatt cacacatttt 420
ttacctagac cagtggaccc cgacaaagta cctgaactgt ataaggatat tctaagccaa 480
agttga 486

<210> SEQ ID NO 22
<211> LENGTH: 384
<212> TYPE: DNA
<213> ORGANISM: Homo sapiens

<400> SEQUENCE: 22
atgcagctat actgcaggac tggatttcac ttagaaatct tccccaatgg tactatccag 60
ggaaccagga aagaccacag ccgatttggc attctggaat ttatcagtat agcagtgggc 120
ctggtcagca ttcgaggcgt ggacagtgga ctctacctcg ggatgaatga gaagggggag 180
ctgtatggat cagaaaaact aacccaagag tgtgtattca gagaacagtt cgaagaaaac 240
tggtataata cgtactcgtc aaacctatat aagcacgtgg acactggaag gcgatactat 300
gttgcattaa ataaagatgg gaccccgaga gaagggacta ggactaaacg gcaccagaaa 360
ttcacacatt ttttacctag atga 384

<210> SEQ ID NO 23
<211> LENGTH: 354
<212> TYPE: DNA
<213> ORGANISM: Homo sapiens

<400> SEQUENCE: 23
atgcacttag aaatcttccc caatggtact atccagggaa ccaggaaaga ccacagccga 60
tttggcattc tggaatttat cagtatagca gtgggcctgg tcagcattcg aggcgtggac 120
agtggactct acctcgggat gaatgagaag ggggagctgt atggatcaga aaaactaacc 180
caagagtgtg tattcagaga acagttcgaa gaaaactggt ataatacgta ctcgtcaaac 240
ctatataagc acgtggacac tggaaggcga tactatgttg cattaaataa agatgggacc 300
ccgagagaag ggactaggac taaacggcac cagaaattca cacatttttt atga 354

<210> SEQ ID NO 24
<211> LENGTH: 360
<212> TYPE: DNA
<213> ORGANISM: Homo sapiens

<400> SEQUENCE: 24
atgcacttag aaatcttccc caatggtact atccagggaa ccaggaaaga ccacagccga 60
tttggcattc tggaatttat cagtatagca gtgggcctgg tcagcattcg aggcgtggac 120
agtggactct acctcgggat gaatgagaag ggggagctgt atggatcaga aaaactaacc 180
caagagtgtg tattcagaga acagttcgaa gaaaactggt ataatacgta ctcgtcaaac 240
ctatataagc acgtggacac tggaaggcga tactatgttg cattaaataa agatgggacc 300
ccgagagaag ggactaggac taaacggcac cagaaattca cacatttttt acctagatga 360

<210> SEQ ID NO 25
<211> LENGTH: 378
<212> TYPE: DNA
<213> ORGANISM: Homo sapiens

<400> SEQUENCE: 25
atgcagctat actgcaggac tggatttcac ttagaaatct tccccaatgg tactatccag 60
ggaaccagga aagaccacag ccgatttggc attctggaat ttatcagtat agcagtgggc 120

-continued

```
ctggtcagca ttcgaggcgt ggacagtgga ctctacctcg ggatgaatga gaagggggag    180

ctgtatggat cagaaaaact aacccaagag tgtgtattca gagaacagtt cgaagaaaac    240

tggtataata cgtactcgtc aaacctatat aagcacgtgg acactggaag gcgatactat    300

gttgcattaa ataaagatgg gaccccgaga gaagggacta ggactaaacg gcaccagaaa    360

ttcacacatt ttttatga                                                  378
```

<210> SEQ ID NO 26
<211> LENGTH: 378
<212> TYPE: DNA
<213> ORGANISM: Homo sapiens

<400> SEQUENCE: 26

```
atgtactgca ggactggatt tcacttagaa atcttcccca atggtactat ccagggaacc     60

aggaaagacc acagccgatt tggcattctg gaatttatca gtatagcagt gggcctggtc    120

agcattcgag gcgtggacag tggactctac ctcgggatga atgagaaggg ggagctgtat    180

ggatcagaaa aactaaccca agagtgtgta ttcagagaac agttcgaaga aaactggtat    240

aatacgtact cgtcaaacct atataagcac gtggacactg gaaggcgata ctatgttgca    300

ttaaataaag atgggacccc gagagaaggg actaggacta aacggcacca gaaattcaca    360

cattttttac ctagatga                                                  378
```

<210> SEQ ID NO 27
<211> LENGTH: 142
<212> TYPE: PRT
<213> ORGANISM: Homo sapiens

<400> SEQUENCE: 27

```
Met Asp His Leu Lys Gly Ile Leu Arg Arg Arg Gln Leu Tyr Cys Arg
1               5                   10                  15

Thr Gly Phe His Leu Glu Ile Phe Pro Asn Gly Thr Ile Gln Gly Thr
            20                  25                  30

Arg Lys Asp His Ser Arg Phe Gly Ile Leu Glu Phe Ile Ser Ile Ala
        35                  40                  45

Val Gly Leu Val Ser Ile Arg Gly Val Asp Ser Gly Leu Tyr Leu Gly
    50                  55                  60

Met Asn Glu Lys Gly Glu Leu Tyr Gly Ser Glu Lys Leu Thr Gln Glu
65                  70                  75                  80

Cys Val Phe Arg Glu Gln Phe Glu Glu Asn Trp Tyr Asn Thr Tyr Ser
                85                  90                  95

Ser Asn Leu Tyr Lys His Val Asp Thr Gly Arg Arg Tyr Tyr Val Ala
            100                 105                 110

Leu Asn Lys Asp Gly Thr Pro Arg Glu Gly Thr Arg Thr Lys Arg His
        115                 120                 125

Gln Lys Phe Thr His Phe Leu Pro Arg Pro Val Asp Pro Asp
    130                 135                 140
```

<210> SEQ ID NO 28
<211> LENGTH: 429
<212> TYPE: PRT
<213> ORGANISM: Homo sapiens

<400> SEQUENCE: 28

```
Ala Thr Gly Gly Ala Thr Cys Ala Thr Thr Thr Ala Ala Ala Gly Gly
1               5                   10                  15
```

-continued

```
Gly Gly Ala Thr Thr Cys Thr Cys Ala Gly Gly Cys Gly Gly Ala Gly
            20                  25                  30

Gly Cys Ala Gly Cys Thr Ala Thr Ala Cys Thr Gly Cys Ala Gly Gly
        35                  40                  45

Ala Cys Thr Gly Gly Ala Thr Thr Thr Cys Ala Cys Thr Thr Ala Gly
    50                  55                  60

Ala Ala Ala Thr Cys Thr Thr Cys Cys Cys Cys Ala Ala Thr Gly Gly
65                  70                  75                  80

Thr Ala Cys Thr Ala Thr Cys Cys Ala Gly Gly Gly Ala Ala Cys Cys
                85                  90                  95

Ala Gly Gly Ala Ala Ala Gly Ala Cys Cys Ala Cys Ala Gly Cys Cys
            100                 105                 110

Gly Ala Thr Thr Thr Gly Gly Cys Ala Thr Thr Cys Thr Gly Gly Ala
        115                 120                 125

Ala Thr Thr Thr Ala Thr Cys Ala Gly Thr Ala Thr Ala Gly Cys Ala
    130                 135                 140

Gly Thr Gly Gly Gly Cys Cys Thr Gly Gly Thr Cys Ala Gly Cys Ala
145                 150                 155                 160

Thr Thr Cys Gly Ala Gly Gly Cys Gly Thr Gly Gly Ala Cys Ala Gly
                165                 170                 175

Thr Gly Gly Ala Cys Thr Cys Thr Ala Cys Cys Thr Cys Gly Gly Gly
            180                 185                 190

Ala Thr Gly Ala Ala Thr Gly Ala Gly Ala Ala Gly Gly Gly Gly Gly
        195                 200                 205

Ala Gly Cys Thr Gly Thr Ala Thr Gly Gly Ala Thr Cys Ala Gly Ala
    210                 215                 220

Ala Ala Ala Ala Cys Thr Ala Ala Cys Cys Cys Ala Ala Gly Ala Gly
225                 230                 235                 240

Thr Gly Thr Gly Thr Ala Thr Thr Cys Ala Gly Ala Gly Ala Ala Cys
                245                 250                 255

Ala Gly Thr Thr Cys Gly Ala Ala Gly Ala Ala Ala Ala Cys Thr Gly
            260                 265                 270

Gly Thr Ala Thr Ala Ala Thr Ala Cys Gly Thr Ala Cys Thr Cys Gly
        275                 280                 285

Thr Cys Ala Ala Ala Cys Cys Thr Ala Thr Ala Thr Ala Ala Gly Cys
    290                 295                 300

Ala Cys Gly Thr Gly Gly Ala Cys Ala Cys Thr Gly Gly Ala Ala Gly
305                 310                 315                 320

Gly Cys Gly Ala Thr Ala Cys Thr Ala Thr Gly Thr Thr Gly Cys Ala
                325                 330                 335

Thr Thr Ala Ala Ala Thr Ala Ala Ala Gly Ala Thr Gly Gly Gly Ala
            340                 345                 350

Cys Cys Cys Cys Gly Ala Gly Ala Gly Ala Ala Gly Gly Gly Ala Cys
        355                 360                 365

Thr Ala Gly Gly Ala Cys Thr Ala Ala Ala Cys Gly Gly Cys Ala Cys
    370                 375                 380

Cys Ala Gly Ala Ala Ala Thr Thr Cys Ala Cys Ala Cys Ala Thr Thr
385                 390                 395                 400

Thr Thr Thr Thr Ala Cys Cys Thr Ala Gly Ala Cys Cys Ala Gly Thr
                405                 410                 415

Gly Gly Ala Cys Cys Cys Cys Gly Ala Cys Thr Gly Ala
            420                 425
```

-continued

<210> SEQ ID NO 29
<211> LENGTH: 208
<212> TYPE: PRT
<213> ORGANISM: Homo sapiens

<400> SEQUENCE: 29

```
Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
            20                  25                  30

Leu Ser Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205
```

<210> SEQ ID NO 30
<211> LENGTH: 208
<212> TYPE: PRT
<213> ORGANISM: Mus musculus

<400> SEQUENCE: 30

```
Met Ala Pro Leu Gly Glu Val Gly Ser Tyr Phe Gly Val Gln Asp Ala
1               5                   10                  15

Val Pro Phe Gly Asn Val Pro Val Leu Pro Val Asp Ser Pro Val Leu
            20                  25                  30

Leu Asn Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
```

-continued

```
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205


<210> SEQ ID NO 31
<211> LENGTH: 208
<212> TYPE: PRT
<213> ORGANISM: Gallus sp.

<400> SEQUENCE: 31

Met Ala Pro Leu Gly Glu Val Gly Asn Tyr Phe Gly Val Gln Asp Ala
1               5                   10                  15

Val Pro Phe Gly Asn Val Pro Ala Leu Pro Ala Asp Ser Pro Val Leu
            20                  25                  30

Leu Ser Asp His Leu Gly Gln Ala Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Gln Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
    130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205


<210> SEQ ID NO 32
<211> LENGTH: 9
<212> TYPE: PRT
<213> ORGANISM: Homo sapiens
<300> PUBLICATION INFORMATION:
<308> DATABASE ACCESSION NUMBER: NCBI/A33665  GI:105188
<309> DATABASE ENTRY DATE: 2000-12-08
<313> RELEVANT RESIDUES: (104)..(112)

<400> SEQUENCE: 32

Leu Glu Glu Asn His Tyr Asn Thr Tyr
1               5


<210> SEQ ID NO 33
<211> LENGTH: 9
```

-continued

<212> TYPE: PRT
<213> ORGANISM: Homo sapiens
<300> PUBLICATION INFORMATION:
<308> DATABASE ACCESSION NUMBER: NCBI/A32398 GI:482272
<309> DATABASE ENTRY DATE: 2000-07-21
<313> RELEVANT RESIDUES: (162)..(170)

<400> SEQUENCE: 33

Leu Glu Ser Asn Asn Tyr Asn Thr Tyr
1 5

<210> SEQ ID NO 34
<211> LENGTH: 9
<212> TYPE: PRT
<213> ORGANISM: Homo sapiens
<300> PUBLICATION INFORMATION:
<308> DATABASE ACCESSION NUMBER: NCBI/P11487 GI:122748
<309> DATABASE ENTRY DATE: 2002-06-15
<313> RELEVANT RESIDUES: (121)..(129)

<400> SEQUENCE: 34

Ile His Glu Leu Gly Tyr Asn Thr Tyr
1 5

<210> SEQ ID NO 35
<211> LENGTH: 9
<212> TYPE: PRT
<213> ORGANISM: Homo sapiens
<300> PUBLICATION INFORMATION:
<308> DATABASE ACCESSION NUMBER: NCBI/P08620 GI:122750
<309> DATABASE ENTRY DATE: 2002-06-15
<313> RELEVANT RESIDUES: (161)..(169)

<400> SEQUENCE: 35

Leu Leu Pro Asn Asn Tyr Asn Ala Tyr
1 5

<210> SEQ ID NO 36
<211> LENGTH: 9
<212> TYPE: PRT
<213> ORGANISM: Homo sapiens
<300> PUBLICATION INFORMATION:
<308> DATABASE ACCESSION NUMBER: NCBI/P12034 GI:13637763
<309> DATABASE ENTRY DATE: 2001-10-16
<313> RELEVANT RESIDUES: (166)..(174)

<400> SEQUENCE: 36

Phe Gln Glu Asn Ser Tyr Asn Thr Tyr
1 5

<210> SEQ ID NO 37
<211> LENGTH: 9
<212> TYPE: PRT
<213> ORGANISM: Homo sapiens
<300> PUBLICATION INFORMATION:
<308> DATABASE ACCESSION NUMBER: NCBI/NP_066276.2 GI:15147343
<309> DATABASE ENTRY DATE: 2003-04-06
<313> RELEVANT RESIDUES: (163)..(171)

<400> SEQUENCE: 37

Leu Leu Pro Asn Asn Tyr Asn Thr Tyr
1 5

<210> SEQ ID NO 38
<211> LENGTH: 9
<212> TYPE: PRT
<213> ORGANISM: Homo sapiens
<300> PUBLICATION INFORMATION:
<308> DATABASE ACCESSION NUMBER: NCBI/NP_002000.1 GI:4503705

-continued

<309> DATABASE ENTRY DATE: 2000-04-03
<313> RELEVANT RESIDUES: (143)..(151)

<400> SEQUENCE: 38

Ile Leu Glu Asn His Tyr Asn Thr Tyr
1 5

<210> SEQ ID NO 39
<211> LENGTH: 9
<212> TYPE: PRT
<213> ORGANISM: Homo sapiens
<300> PUBLICATION INFORMATION:
<308> DATABASE ACCESSION NUMBER: NCBI/NP_149354.1 GI:15147348
<309> DATABASE ENTRY DATE: 2003-04-06
<313> RELEVANT RESIDUES: (151)..(159)

<400> SEQUENCE: 39

Val Leu Glu Asn Asn Tyr Thr Ala Leu
1 5

<210> SEQ ID NO 40
<211> LENGTH: 9
<212> TYPE: PRT
<213> ORGANISM: Homo sapiens
<300> PUBLICATION INFORMATION:
<308> DATABASE ACCESSION NUMBER: NCBI/BAA03572.1 GI:391719
<309> DATABASE ENTRY DATE: 2003-02-11
<313> RELEVANT RESIDUES: (140)..(148)

<400> SEQUENCE: 40

Phe Glu Glu Asn Trp Tyr Asn Thr Tyr
1 5

<210> SEQ ID NO 41
<211> LENGTH: 9
<212> TYPE: PRT
<213> ORGANISM: Homo sapiens
<300> PUBLICATION INFORMATION:
<308> DATABASE ACCESSION NUMBER: NCBI/BAA22331.1 GI:2440221
<309> DATABASE ENTRY DATE: 1999-05-13
<313> RELEVANT RESIDUES: (156)..(164)

<400> SEQUENCE: 41

Ile Glu Glu Asn Gly Tyr Asn Thr Tyr
1 5

<210> SEQ ID NO 42
<211> LENGTH: 9
<212> TYPE: PRT
<213> ORGANISM: Homo sapiens
<300> PUBLICATION INFORMATION:
<308> DATABASE ACCESSION NUMBER: NCBI/Q92914 GI:2494457
<309> DATABASE ENTRY DATE: 1997-11-01
<313> RELEVANT RESIDUES: (149)..(157)

<400> SEQUENCE: 42

Val Phe Glu Asn Tyr Tyr Val Leu Tyr
1 5

<210> SEQ ID NO 43
<211> LENGTH: 9
<212> TYPE: PRT
<213> ORGANISM: Homo sapiens
<300> PUBLICATION INFORMATION:
<308> DATABASE ACCESSION NUMBER: NCBI/Q92912 GI:2494459
<309> DATABASE ENTRY DATE: 2002-06-15
<313> RELEVANT RESIDUES: (151)..(159)

<400> SEQUENCE: 43

-continued

```
Val Phe Glu Asn Tyr Tyr Val Ile Tyr
1               5


<210> SEQ ID NO 44
<211> LENGTH: 9
<212> TYPE: PRT
<213> ORGANISM: Homo sapiens
<300> PUBLICATION INFORMATION:
<308> DATABASE ACCESSION NUMBER: NCBI/NP_003858.1  GI:4503693
<309> DATABASE ENTRY DATE: 2003-04-06
<313> RELEVANT RESIDUES: (147)..(155)

<400> SEQUENCE: 44

Val Phe Glu Asn Tyr Tyr Val Thr Tyr
1               5


<210> SEQ ID NO 45
<211> LENGTH: 9
<212> TYPE: PRT
<213> ORGANISM: Homo sapiens
<300> PUBLICATION INFORMATION:
<308> DATABASE ACCESSION NUMBER: NCBI/Q92915  GI:2494463
<309> DATABASE ENTRY DATE: 2002-06-15
<313> RELEVANT RESIDUES: (149)..(157)

<400> SEQUENCE: 45

Val Phe Glu Asn Tyr Tyr Val Ile Tyr
1               5


<210> SEQ ID NO 46
<211> LENGTH: 9
<212> TYPE: PRT
<213> ORGANISM: Homo sapiens
<300> PUBLICATION INFORMATION:
<308> DATABASE ACCESSION NUMBER: NCBI/NP_003859.1  GI:4503691
<309> DATABASE ENTRY DATE: 1999-07-15
<313> RELEVANT RESIDUES: (133)..(141)

<400> SEQUENCE: 46

Met Asp Cys Leu Gly Tyr Asn Gln Tyr
1               5


<210> SEQ ID NO 47
<211> LENGTH: 9
<212> TYPE: PRT
<213> ORGANISM: Homo sapiens
<300> PUBLICATION INFORMATION:
<308> DATABASE ACCESSION NUMBER: NCBI/NP_003859.1  GI:4503691
<309> DATABASE ENTRY DATE: 1998-04-16
<313> RELEVANT RESIDUES: (139)..(147)
<300> PUBLICATION INFORMATION:
<308> DATABASE ACCESSION NUMBER: NCBI/NP_003859.1  GI:4503691
<309> DATABASE ENTRY DATE: 2003-04-16
<313> RELEVANT RESIDUES: (139)..(147)

<400> SEQUENCE: 47

Phe Glu Glu Asn Trp Tyr Asn Thr Tyr
1               5


<210> SEQ ID NO 48
<211> LENGTH: 9
<212> TYPE: PRT
<213> ORGANISM: Homo sapiens
<300> PUBLICATION INFORMATION:
<308> DATABASE ACCESSION NUMBER: NCBI/BAA25429.1  GI:3041790
<309> DATABASE ENTRY DATE: 1998-04-16
<313> RELEVANT RESIDUES: (133)..(141)

<400> SEQUENCE: 48
```

-continued

Val Leu Glu Asn Asn Tyr Thr Ala Phe
1 5

<210> SEQ ID NO 49
<211> LENGTH: 9
<212> TYPE: PRT
<213> ORGANISM: Homo sapiens
<300> PUBLICATION INFORMATION:
<308> DATABASE ACCESSION NUMBER: NCBI/AAC62240.1 GI:3687843
<309> DATABASE ENTRY DATE: 1998-10-02
<313> RELEVANT RESIDUES: (133)..(141)

<400> SEQUENCE: 49

Val Leu Glu Asn Asn Tyr Thr Ala Leu
1 5

<210> SEQ ID NO 50
<211> LENGTH: 9
<212> TYPE: PRT
<213> ORGANISM: Homo sapiens
<300> PUBLICATION INFORMATION:
<308> DATABASE ACCESSION NUMBER: NCBI/BAA75500.1 GI:4514718
<309> DATABASE ENTRY DATE: 1999-03-02
<313> RELEVANT RESIDUES: (126)..(134)

<400> SEQUENCE: 50

Ile Arg Pro Asp Gly Tyr Asn Val Tyr
1 5

<210> SEQ ID NO 51
<211> LENGTH: 9
<212> TYPE: PRT
<213> ORGANISM: Homo sapiens
<300> PUBLICATION INFORMATION:
<308> DATABASE ACCESSION NUMBER: NCBI/Q9NP95 GI:13626702
<309> DATABASE ENTRY DATE: 2001-10-16
<313> RELEVANT RESIDUES: (143)..(151)

<400> SEQUENCE: 51

Phe Glu Glu Asn Trp Tyr Asn Thr Tyr
1 5

<210> SEQ ID NO 52
<211> LENGTH: 9
<212> TYPE: PRT
<213> ORGANISM: Homo sapiens
<300> PUBLICATION INFORMATION:
<308> DATABASE ACCESSION NUMBER: NCBI/BAA99415.1 GI:9049445
<309> DATABASE ENTRY DATE: 2000-08-03
<313> RELEVANT RESIDUES: (127)..(135)

<400> SEQUENCE: 52

Leu Leu Glu Asp Gly Tyr Asn Val Tyr
1 5

<210> SEQ ID NO 53
<211> LENGTH: 9
<212> TYPE: PRT
<213> ORGANISM: Homo sapiens
<300> PUBLICATION INFORMATION:
<308> DATABASE ACCESSION NUMBER: NCBI/BAB13479.1 GI:10119767
<309> DATABASE ENTRY DATE: 2001-02-23
<313> RELEVANT RESIDUES: (119)..(127)

<400> SEQUENCE: 53

Ile Glu Glu Asn Gly His Asn Thr Tyr
1 5

<210> SEQ ID NO 54
<211> LENGTH: 9
<212> TYPE: PRT
<213> ORGANISM: Homo sapiens
<300> PUBLICATION INFORMATION:
<308> DATABASE ACCESSION NUMBER: NCBI/BAB13477.1 GI:10119774
<309> DATABASE ENTRY DATE: 2000-11-11
<313> RELEVANT RESIDUES: (119)..(127)

<400> SEQUENCE: 54

Thr Leu Glu Asn Gly Tyr Asp Val Tyr
1 5

<210> SEQ ID NO 55
<211> LENGTH: 9
<212> TYPE: PRT
<213> ORGANISM: Homo sapiens

<400> SEQUENCE: 55

Phe Glu Glu Asn Trp Tyr Asn Thr Tyr
1 5

<210> SEQ ID NO 56
<211> LENGTH: 25
<212> TYPE: DNA
<213> ORGANISM: Artificial
<220> FEATURE:
<223> OTHER INFORMATION: primer

<400> SEQUENCE: 56
cgaagaaaac gggtataata cgtac 25

<210> SEQ ID NO 57
<211> LENGTH: 25
<212> TYPE: DNA
<213> ORGANISM: Artificial
<220> FEATURE:
<223> OTHER INFORMATION: primer

<400> SEQUENCE: 57
gtacgtatta tacccgtttt cttcg 25

<210> SEQ ID NO 58
<211> LENGTH: 22
<212> TYPE: DNA
<213> ORGANISM: Artificial
<220> FEATURE:
<223> OTHER INFORMATION: primer

<400> SEQUENCE: 58
cgaagaaaac cggtataata cg 22

<210> SEQ ID NO 59
<211> LENGTH: 22
<212> TYPE: DNA
<213> ORGANISM: Artificial
<220> FEATURE:
<223> OTHER INFORMATION: primer

<400> SEQUENCE: 59
cgtattatac cggttttctt cg 22

<210> SEQ ID NO 60
<211> LENGTH: 22
<212> TYPE: DNA
<213> ORGANISM: Artificial

-continued

<220> FEATURE:
<223> OTHER INFORMATION: primer

<400> SEQUENCE: 60
cgaagaaaac gtgtataata cg 22

<210> SEQ ID NO 61
<211> LENGTH: 22
<212> TYPE: DNA
<213> ORGANISM: Artificial
<220> FEATURE:
<223> OTHER INFORMATION: primer

<400> SEQUENCE: 61
cgtattatac acgttttctt cg 22

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
cgaagaaaac gagtataata cg 22

<210> SEQ ID NO 63
<211> LENGTH: 22
<212> TYPE: DNA
<213> ORGANISM: Artificial
<220> FEATURE:
<223> OTHER INFORMATION: primer

<400> SEQUENCE: 63
cgtattatac tcgttttctt cg 22

<210> SEQ ID NO 64
<211> LENGTH: 22
<212> TYPE: DNA
<213> ORGANISM: Artificial
<220> FEATURE:
<223> OTHER INFORMATION: primer

<400> SEQUENCE: 64
cgaagaaaac gcgtataata cg 22

<210> SEQ ID NO 65
<211> LENGTH: 22
<212> TYPE: DNA
<213> ORGANISM: Artificial
<220> FEATURE:
<223> OTHER INFORMATION: primer

<400> SEQUENCE: 65
cgtattatac gcgttttctt cg 22

<210> SEQ ID NO 66
<211> LENGTH: 22
<212> TYPE: DNA
<213> ORGANISM: Artificial
<220> FEATURE:
<223> OTHER INFORMATION: primer

<400> SEQUENCE: 66
cgaagaaaac aattataata cg 22

-continued

<210> SEQ ID NO 67
<211> LENGTH: 22
<212> TYPE: DNA
<213> ORGANISM: Artificial
<220> FEATURE:
<223> OTHER INFORMATION: primer

<400> SEQUENCE: 67
cgtattataa ttgttttctt cg 22

<210> SEQ ID NO 68
<211> LENGTH: 32
<212> TYPE: DNA
<213> ORGANISM: Artificial
<220> FEATURE:
<223> OTHER INFORMATION: primer

<400> SEQUENCE: 68
agctggatcc tcaactttgg cttagaatat cc 32

<210> SEQ ID NO 69
<211> LENGTH: 29
<212> TYPE: DNA
<213> ORGANISM: Artificial
<220> FEATURE:
<223> OTHER INFORMATION: primer

<400> SEQUENCE: 69
acgtgaccat atgggtcagt ccgaagcag 29

<210> SEQ ID NO 70
<211> LENGTH: 33
<212> TYPE: DNA
<213> ORGANISM: Artificial
<220> FEATURE:
<223> OTHER INFORMATION: primer

<400> SEQUENCE: 70
gggaattcca tatgcagcta tactgcagga ctg 33

<210> SEQ ID NO 71
<211> LENGTH: 27
<212> TYPE: DNA
<213> ORGANISM: Artificial
<220> FEATURE:
<223> OTHER INFORMATION: primer

<400> SEQUENCE: 71
gttcgaagaa agctggtata atatacg 27

<210> SEQ ID NO 72
<211> LENGTH: 25
<212> TYPE: DNA
<213> ORGANISM: Artificial
<220> FEATURE:
<223> OTHER INFORMATION: primer

<400> SEQUENCE: 72
cgtattatac cagctttctt cgaac 25

<210> SEQ ID NO 73
<211> LENGTH: 31
<212> TYPE: DNA
<213> ORGANISM: Artificial
<220> FEATURE:
<223> OTHER INFORMATION: primer -continued

<400> SEQUENCE: 73
ggccctaggt catctaggta aaaaatgtgt g 31

<210> SEQ ID NO 74
<211> LENGTH: 33
<212> TYPE: DNA
<213> ORGANISM: Artificial
<220> FEATURE:
<223> OTHER INFORMATION: primer

<400> SEQUENCE: 74
gggaattcca tatgcagcta tactgcagga ctg 33

<210> SEQ ID NO 75
<211> LENGTH: 32
<212> TYPE: DNA
<213> ORGANISM: Artificial
<220> FEATURE:
<223> OTHER INFORMATION: primer

<400> SEQUENCE: 75
agctggatcc tcaactttgg cttagaatat cc 32

<210> SEQ ID NO 76
<211> LENGTH: 23
<212> TYPE: DNA
<213> ORGANISM: Artificial
<220> FEATURE:
<223> OTHER INFORMATION: primer

<400> SEQUENCE: 76
gagtgaccat atgggtcagt cgc 23

<210> SEQ ID NO 77
<211> LENGTH: 34
<212> TYPE: DNA
<213> ORGANISM: Artificial
<220> FEATURE:
<223> OTHER INFORMATION: primer

<400> SEQUENCE: 77
gggaattcca tatgcccagg ggacccgcag tcac 34

<210> SEQ ID NO 78
<211> LENGTH: 30
<212> TYPE: DNA
<213> ORGANISM: Artificial
<220> FEATURE:
<223> OTHER INFORMATION: primer

<400> SEQUENCE: 78
cgatacgtac atatgcactt agaaatcttc 30

<210> SEQ ID NO 79
<211> LENGTH: 28
<212> TYPE: DNA
<213> ORGANISM: Artificial
<220> FEATURE:
<223> OTHER INFORMATION: primer

<400> SEQUENCE: 79
gcaaggatcc tcaatgtgtg aatttctg 28

<210> SEQ ID NO 80

-continued

```
<211> LENGTH: 30
<212> TYPE: DNA
<213> ORGANISM: Artificial
<220> FEATURE:
<223> OTHER INFORMATION: primer

<400> SEQUENCE: 80

acgatcgtac atatgtactg caggactgga                                   30
```

ACTIVE VARIANTS OF FGF WITH IMPROVED SPECIFICITY

CROSS-REFERENCE

This application is a continuation of the U.S. National Stage designation of International Application PCT/IL01/00962, filed on Oct. 18, 2001. The content of which is expressly incorporated herein by reference thereto.

FIELD OF THE INVENTION

The present invention concerns active mutants and variants of fibroblast growth factors (FGFs) with improved properties, including modifications to the loop comprising residues of a major receptor binding domain involved in receptor specificity and modifications in the N-terminus and C-terminus that provide highly active FGF polypeptides, pharmaceutical compositions comprising these variants and methods for use thereof.

BACKGROUND OF THE INVENTION

Fibroblast growth factors (FGFs) comprise a family of at least 24 multifunctional polypeptides involved in a variety of biological processes including morphogenesis, angiogenesis, and tissue remodeling as well as in the pathogenesis of numerous diseases (for review see Ornitz, Bioessays 22, 108, 2000). The various members of this family stimulate the proliferation of a wide spectrum of cells, ranging from mesenchymal to epithelial and neuroectodermal origin in vitro and in vivo. Types of cells responding to FGF mitogenic stimuli include fibroblasts, corneal and vascular endothelial cells, granulocytes, adrenal cortical cells, chondrocytes, myoblasts, vascular smooth muscle cells, lens epithelial cells, melanocytes, keratinocytes, oligodendrocytes, astrocytes, osteoblasts, and hematopoietic cells. FGFs are expressed in a strict temporal and spatial pattern during development and have important roles in patterning and limb formation (Ornitz et al., J. Biol. Chem. 271, 15292, 1996).

FGFs are powerful mitogens and are critical in regulation of many biological processes including angiogenesis, vasculogenesis, wound healing, limb formation, tumorigenesis and cell survival. The biological response of cells to FGF is mediated through specific, high affinity (Kd 20-500 pM) cell surface receptors that possess intrinsic tyrosine kinase activity and are phosphorylated upon binding of FGF (Coughlin et al. J Biol. Chem. 263, 988, 1988). Five distinct Fibroblast Growth Factor Receptors (FGFRs) have been identified (Johnson and Williams, Adv. Cancer Res. 60, 1993; Sleeman et al., Gene 271, 171, 2001). The FGFR extracellular domain consists of three immunoglobulin-like (Ig-like) domains (D1, D2 and D3), a heparin binding domain and an acidic box. Alternative splicing of the FGF receptor mRNAs generates different variants of the receptors. In general, the FGF family members bind to all of the known FGFRs, however, some FGFs bind to specific receptors with higher degrees of affinity. The FGFR genes have been cloned and identified in mammals and their homologues described in birds, *Xenopus* and *Drosophila* (Givol and Yayon, FASEB J. 6, 3369, 1992).

Another critically functional component in receptor activation is the binding to proteoglycans such as heparan sulfate. FGFs fail to bind and activate FGF receptors in cells deprived of endogenous heparan sulfate. Different models have been suggested in attempts to explain the role of heparan sulfate proteoglycan (HSPG) in FGF signaling, including the formation of a functional tertiary complex between FGF, FGFR and the appropriate HSPG (Yayon et al., Cell 64, 841, 1991).

A number of birth defects are associated with mutations in the genes encoding FGF receptors. For example a mutation in FGFR1 is associated with Pfeiffer syndrome. Certain other mutations in FGFR2 are associated with Crouzon, Pfeiffer, Jackson-Weiss, Apert or Beare-Stevenson syndromes. The clinical manifestation of Apert syndrome (AS) is characterized by both bony and cutaneous fusion of digits of the hands and the feet. Broad thumbs and halluces distinguish Pfeiffer syndrome, while in Crouzon syndrome limbs are normal but a high degree of proptosis is evident. The most prominent malformation syndrome associated with these mutations is craniosynostosis (the premature fusion of the skull bones sutures). Mutations in FGFR3 are responsible for achondroplasia, the most common form of human genetic dwarfism. Thanatophoric dysplasia is a severe and lethal form of FGFR3 mutations, while hypochondroplasia is a milder form of achondroplasia. Examination of the sequence of FGFR3 in achondroplasia patients identified a mutation in the transmembrane domain of the receptor (reviewed in Vajo et al., Endocrine Rev. 21, 23, 2000).

The FGFRs have been implicated in certain malignancies. FGFR3 is the most frequently mutated oncogene in bladder cancer where it is mutated in more than 30% of the cases (Cappellen et al., Nature Genet. 23, 18, 1999). Recently, Dvorakova et al. (Br. J. Haematol. 113, 832, 2001) have shown that the FGFR3IIIc isoform is overexpressed in the white blood cells of chronic myeloid leukemia (CML) patients. Yee et al. (J. Natl. Cancer 92, 1848, 2000) have identified a mutation in FGFR3 linked to cervical carcinoma.

A great deal of work was invested in structure-function studies of FGFs and their receptor binding elements. These have led to the determination of the major and minor receptor binding domains, heparin-binding residues, peptomimetics having structures based on FGFs and FGF peptides that were constructed from phage-display technology.

It has been well characterized that some FGFs, such as FGF-1, stimulate all of the receptor isoforms, however, some FGFs bind specifically to selected receptors with orders of magnitude higher affinities. Specificity may also be achieved by other factors, such as different proteoglycans, expressed in different tissues (Ornitz, Bioessays, 22, 108, 2000). Recently, site-directed mutagenesis and X-ray crystallography were used to investigate the basis of specificity of FGFs to their receptors. These were based mostly on the structures of the extracellular domain of FGFR1 and FGFR2 bound to FGF-1 and FGF-2 (Plotnikov et al., Cell 98, 641, 1999; Plotnikov et al., Cell 101, 413, 2000; Stauber et al., PNAS USA 97, 49, 2000; Pellegrini, et al., Nature, 407, 1029, 2000; Schlessinger et al., Mol Cell, 6, 43, 2000).

Generation of specific ligands would be useful for the purpose of research as well as for the purpose of developing possible medicaments for treatment of diseases and disorders including tumor progression, skin lesions, neurodegenerative diseases, bone fracture healing, achondroplasia, and other skeletal disorders. Additionally, the focus of FGFR3 as the receptor involved in achondroplasia, as well as in cancer including but not limited to transitional cell carcinoma (TCC) of the bladder, multiple myeloma, chronic myeloid leukemia (CML) and cervical carcinoma has raised the unmet need for ligands specific for this receptor, which do not substantially bind to the other four FGFRs. In light of the large number of FGFs and receptor variants, a major question regarding FGF function is their receptor specificity. In fact, all FGFRs tested so far bind FGF-1 and FGF-4 with moderate to high affinity, demonstrating an apparent redundancy in the FGF system. In contrast to FGFR1 and FGFR2, the third receptor subtype, FGFR3 was found to bind with high affinities to FGF-8, FGF-17 and FGF-18 and with improved selectivity to FGF-9. Producing FGF ligands with enhanced receptor selectivity, higher stimulative activity in vivo, and ease of expression mode, is highly needed for treatment of various pathological conditions.

Attempts have been made to alter FGF receptor specificity by deletions or truncations of its ligands, by means of mutations introduced at certain locations within the gene encoding for the proteins. Mutations affecting the binding affinity as well as binding to heparin have been demonstrated by several investigators. For example Seno et al. (Eur. J. Biochem. 188, 239, 1990) studied the effect of the carboxy and amino termini of basic FGF on the affinity for heparin. Truncation of more than 6 amino acids from the C-terminus of bFGF decreased the affinity for heparin, though removal of up to 46 amino acids showed a significant stimulation of the proliferative effect. Removal of 40 amino acids from the N-terminus exhibited comparable affinity to heparin as that of intact bFGF, and induced stimulation of DNA synthesis.

Additional truncated versions of molecules of the FGF family have been reported by Kuroda et al., (Bone, 25, 431, 1999). Kuroda et al., produced amino terminus truncated human FGF-4 of various sizes, and tested the effects on growth stimulation and increase in bone density. The full-length polypeptide, and a shortened version containing 134 amino acid residues demonstrated comparable cellular proliferation and effect on increase of bone density. The shortest form of FGF-4 tested, containing only 111 amino acid residues exhibited limited growth stimulatory activity.

A spontaneous truncation of 34 amino acid residues, including the methionine residue encoded by the initiation codon, was discovered in the N-terminus of FGF-16 expressed in *E. coli*. The variant retained biological activity as measured as induction of cell proliferation in vitro as well as in vivo (Danilenko et al., Arch. Biochem. Biophys. 1, 361, 1999). In addition, FGF-16 having from one to thirty-four amino acids deleted from the N-terminus or from one to eighteen amino acids deleted from the C-terminus, was shown to retain biological activity (U.S. Pat. No. 5,998,170).

The human FGF-9 gene was found to code for a 208 amino acid protein, which shares approximately 30% homology with other FGFs and presents a unique spectrum of biological activity as it stimulates the proliferation of glial cells, PC-12 cells and BALB/C 3T3 fibroblasts, but not endothelial cells (U.S. Pat. Nos. 5,622,928, and 5,512,460). A 152 amino acid fragment of the FGF-9 comprising a truncation of 53 amino acids from the N-terminus and 13 amino acids from the C-terminus is further disclosed in U.S. Pat. No. 5,512,460. Deletion of 54 amino acids from the N-terminus of the protein yielded a 154 amino acid protein retaining its biological activity (U.S. Pat. No. 5,571,895).

Basic FGF (FGF-2) has been modified to alter biological properties and binding specificity. U.S. Pat. No. 5,491,220 discloses structural analogues of FGF-2 that comprise substitution of the β9-β10 loop with that of another FGF or IL-1β to alter biological properties and binding specificity. Human FGF-2 (basic FGF) has been designed with substitutions at either one or more of the following amino acids glutamate 89, aspartate 101 and/or leucine 137, which impart beneficial therapeutic properties (U.S. Pat. No. 6,274,712). U.S. Pat. No. 6,294,359 discloses analogs of FGF-2 that comprise amino acid substitutions at heparin and receptor binding domains. The patent presents analogs that are either agonist or antagonist with respect to wild type FGF in a cell proliferation assay but does not teach receptor specificity changes.

Mutant forms of FGF-10 (also known as KGF-2) including amino and carboxy terminal truncations and amino acid substitutions have been disclosed in U.S. Pat. No. 6,077,692. The patent discloses variants that exhibit enhanced activity, higher yields or increased stability but neither teaches nor suggests a change in receptor specificity.

WO 01/39788 discloses targeting cells expressing FGFR2 or FGFR3 by using compositions comprising FGF-18.

The extensive efforts made to produce truncation, deletion and point mutation variants in FGF have resulted in changes in affinity to the receptors but not in significant alterations in receptor specificity. Thus, there is an unmet need for highly active and selective ligands for the various types of FGF receptors that would be useful in stimulation or inhibition of these receptors thereby addressing the clinical manifestations associated with the above-mentioned mutations, and modulating various biological functions.

It is explicitly to be understood that known active fragments of FGFs are excluded from the present invention.

SUMMARY OF THE INVENTION

It is an object of the present invention to provide active mutants and/or variants of members of the FGF family wherein specific modifications render them advantageous in that they have enhanced receptor specificity, and/or are more stable, and/or have higher in vivo activity.

It is another object of the present invention to provide FGFs with improved receptor subtype specificity having mutations in a major receptor-binding domain. It is a further object of the present invention to provide active variants of members of the FGF family wherein certain specific truncations of the carboxy and/or amino termini renders them advantageous in that they are more stable, with improved receptor specificity, and/or higher in vivo activity. It is still a further object of the present invention to provide a small and stable FGF that retains mitogenic activity and receptor specificity.

It is yet another object to provide methods for the use of FGF variants to prepare medicaments useful in bone formation and fracture healing, as well as in the detection and treatment of various FGFR related disorders including but not limited to skeletal and cartilage defects.

Certain modifications will prevent or decrease activity at specific FGF receptors, such as, but not limited to, FGF Receptor 3, providing variants with therapeutic benefits for treating certain types of cancer including but not limited to multiple myeloma, epithelial cancers such as transitional cell carcinoma (TCC) of the bladder and cervical carcinoma.

Conversely, other modifications will enhance activity at specific FGF receptors, such as, but not limited to, FGF Receptor 3, providing variants with therapeutic benefits for promoting neovascularization in indications including burns, cuts, lacerations, bed sores, ulcers such as those seen in diabetic patients and in tissue repair following ischemic insults and myocardial infarction.

All members of the FGF family share in their primary sequence a homology core of about 120 amino acids, twenty-eight amino acid residues are highly conserved and six are identical. Structural studies on FGF-1, FGF-2, FGF-4, FGF-7 and FGF-9 identified 12 antiparallel β strands, conserved throughout the family. The core domain comprises the primary FGFR and heparin binding sites. Regions thought to be involved in receptor binding are distinct from regions that bind heparin (reviewed in Omitz and Itoh, Gen. Biol. 2, 30005.1, 2001).

According to the principles of the present invention it is now disclosed that mutations in the loop between the β8 and β9 strands of FGF-9, herein defined as β8-β9, previously determined to comprise a major binding site demonstrated to interact with the receptor, and homologous loops in the other members of the FGF family, provide enhanced receptor subtype specificity. Thus according to a certain currently preferred embodiment of the invention there is provided an FGF having a substitution of at least one residue in a major binding site of the molecule with the receptor. An amino acid substitution according to the invention affects binding of the variant to one receptor but not to another thereby providing a basis for receptor specific mutants of FGFs. The FGF variant has enhanced specificity for one receptor subtype compared to the corresponding wild type FGF, by decreasing the biological activity mediated by at least one receptor subtype while retaining the activity mediated through another receptor subtype.

According to one currently preferred embodiment of the present invention it is possible to diminish the biological activity resulting from binding to FGFR1 while retaining a high level of biological activity elicited through FGFR3. Preferably the activity mediated through FGFR2 is largely unaffected. More preferably the activity ratio of the variants on FGFR1 versus FGFR3 decreases.

Preferably the mutation results in a substitution of tryptophan 144, as numbered according to FGF-9, or an amino acid in the corresponding position of the β8-β9 loop of an FGF. More preferably the mutation is in the β8-β9 loop of FGF-9 or FGF-16 or FGF-20. Here we disclose increased receptor specificity by a point mutation in FGF-9 resulting in an amino acid substitution in the loop between the β8 and β9 strands.

According to one currently most preferred embodiment of the present invention Trp144 (W144) of FGF-9 is replaced with other amino acid residues providing altered levels of biological activity and receptor specificity. Introduction of glycine at position 144 of FGF-9 abolishes its binding to FGFR1, while retaining significant affinity towards FGFR3 and to lesser extent, FGFR2. This mutation is denoted herein W144G-FGF9.

According to additional preferred embodiments of the invention Trp144 of FGF-9, or the equivalent position in other FGFs, is substituted with amino acid residues including, but not limited to arginine, valine or glutamate to abolish the binding to FGFR1 while retaining high affinity binding to FGFR3 and a lesser affinity to FGFR2.

Another aspect of the invention provides a substitution of another residue in the β8-β9 loop, namely the amino acid adjacent to Trp144, asparagine 143 (Asp143 or N143) of FGF-9, or the equivalent position in other FGFs, with another amino acid residue including, but not limited to serine, to diminish binding to FGFR1 while retaining high affinity binding to FGFR3 and a lesser affinity to FGFR2. This variant is denoted herein N143S-FGF9.

According to additional features of the present invention, it is now disclosed that the carboxy and amino termini of the molecule can be varied, thereby yielding active variants with improved properties. The variants thus obtained will have the inherent mitogenic properties of the FGF molecules but may be designed to have improved properties in terms of receptor specificity, stability or affinity. Furthermore, the variants so obtained may further be advantageous in terms of their ability to be expressed in commercially relevant quantities using recombinant molecular biological techniques as are known in the art.

Unexpectedly, it is now disclosed that truncated variants may indeed be less active in promoting growth of transformed cells than their corresponding full-length wild type growth factor. Truncated variants of the invention that are most preferred may further comprise at least one mutation in at least one binding site to the receptor and are more selective than the corresponding full length wild type growth factor.

The present invention is directed to novel variants of FGF, and in particular to variants of FGF-9. It is within the scope of the present invention to delete fragments of FGF-9 from either the N-terminus or the C-terminus or both termini or to modify one or both termini, while retaining the mitogenic activity mediated via FGFRs with unimpaired or improved affinities compared to the wild type FGF-9, from which it was derived.

A currently preferred embodiment of the present invention provides for the first time the shortest active variant of FGF-9, denoted R64M-FGF9, also designated FGF9-1, wherein truncation of 63 amino acids from the N-terminus yields a ligand with high specificity towards FGFR3.

Another currently more preferred embodiment of the invention provides a fusion protein comprising R64M-FGF9 which yields an active ligand with high specificity towards FGFR3, which further comprises a 6× His tag and a thrombin cleavage site fused to the N-terminus of R64M-FGF9, herein denoted as hisR64M-FGF9.

Another currently most preferred embodiment according to the present invention comprises a receptor selective active variant obtained by substitution of an amino acid within a binding site to the receptor, which further comprises a 36 amino acid truncation from the N terminus of FGF. This mutant is denoted herein as L37M-W144G-FGF9.

These specific novel mutants are particularly useful in:

(i) high expression systems suitable for pharmaceutical production since the truncated variants of the invention generate a high yield in an expression system;
(ii) compositions with therapeutic utility in bone fracture healing, repair of cartilage defects, wound healing, and as anti-osteoporosis agents;
(iii) targeting of drugs or other agents to tissues and cells having specific FGFR subtypes;
(iv) serving as a template for the formation of improved agonists and antagonists of FGFRs in various disorders such as skeletal disorders and cancer.

Currently most preferred embodiments in accordance to the invention comprising mutated forms of FGF are denoted herein as follows:

1) W144X-FGF9 (SEQ ID NO: 1) wherein X at position 144 of FGF-9 is other than Trp (W), and wherein the currently preferred substitution is selected from Gly (G), Arg (R), Val (V) or Glu (E).
2) L37M-W144X-FGF9 (SEQ ID NO: 2) having 172 amino acids with an amino terminus truncation of 36 amino acids, the leucine at position 37 of the native FGF-9 replaced by methionine and wherein X at position 144 of FGF-9 is other than Trp (W), and wherein the currently preferred substitution is selected from Gly (G), Arg (R), Val (V) or Glu (E).
3) N143X-FGF9 (SEQ ID NO: 3) wherein X at position 143 of FGF-9 is other than Asn (N), and wherein the currently preferred substitution is Ser (S).
4) L37M-N143X-FGF9 (SEQ ID NO: 4) having 172 amino acids with an amino terminus truncation of 36 amino acids, the leucine at position 37 of the native FGF-9 replaced by methionine and wherein X at position 143 is other than Asn (N) and wherein the currently preferred substitution is Ser (S).

Additional currently preferred embodiments in accordance with the present invention, comprising truncated forms of FGF-9 are denoted herein as follows:

5) R64M-FGF9 (SEQ ID NO:5) having 145aa with a truncation of 63 amino acid residues from the amino terminus, the arginine at position 64 of the native FGF-9 replaced by methionine.

6) L45M-FGF-9 (SEQ ID NO:6) having 164aa with a truncation of 44 amino acids from the amino terminus of the native FGF-9 and the leucine at position 45 of the native FGF-9 replaced by methionine.

7) L37M-FGF-9 (SEQ ID NO:7) having 172aa with a truncation of 36 amino acids from the amino terminus of native FGF-9 and the leucine at position 37 of the native FGF-9 replaced by methionine.

8) hisR64M-FGF9 (SEQ ID NO:8) having 161 aa with a truncation of 63 amino acids at the amino terminus of native FGF-9 and an arginine at position 64 of the native FGF-9 replaced by methionine with 16 aa fused at the N-terminus comprising a 6× His tag and thrombin cleavage site originating from the pET expression vector.

The core structure of approximately 120 amino acids (about amino acids 66-192 of FGF-9) has been shown to be crucial for FGF function. The following examples, in which truncations were extended into the core structure, having decreased activity include:

9) FGF9-2 (SEQ ID NO:9) having 127aa with a truncation of 63 amino acids from the amino terminus, the arginine at position 64 of the native FGF-9 replaced by methionine and a truncation of 18 amino acids from the carboxy terminus of native FGF-9, the proline at position 189 of the native FGF-9 replaced with a termination signal.

10) F72M-P189stop-F9 (SEQ ID NO:10) having 117aa with a truncation of 71 amino acids from the N terminus and the phenylalanine at position 72 of the native FGF-9 replaced by methionine and a truncation of 20 amino acids from the C terminus, the proline at position 189 of the native FGF-9 replaced with a termination signal.

11) F72M-P191Stop-F9 (SEQ ID NO:11) having 119aa with a truncation of 71 amino acids from the N terminus, the phenylalanine at position 72 of the native FGF-9 replaced by methionine and a truncation of 18 amino acids from the C terminus, the proline at position 191 of the native FGF-9 replaced with a termination signal.

12) R64M-P191Stop-F9 (SEQ ID NO:12) having 127aa with a truncation of 63 amino acids from the N terminus and an arginine at position 64 of the native FGF-9 replaced by methionine and a truncation of 18 amino acids from the C terminus, the proline at position 191 of the native FGF-9 replaced with a termination signal.

13) L66M-P191Stop-F9-2 (SEQ ID NO:13) having 125aa with a truncation of 65 amino acids from the N terminus and a leucine at position 66 replaced by methionine and a truncation of 18 amino acids from the C terminus, the proline at position 191 of the native FGF-9 replaced with a termination signal.

The polynucleotide sequences corresponding to these novel mutated and/or truncated forms of FGF-9 are disclosed herein as follows:

14) W144X-FGF9 DNA (SEQ ID NO:14).
15) L37M-W144X-FGF9 DNA (SEQ ID NO:15).
16) N143X-FGF9 DNA (SEQ ID NO:16).
17) L37M-N144X-FGF9 DNA (SEQ ID NO:17).
18) R64M-FGF9 DNA (SEQ ID NO:18).
19) L45M-FGF9 DNA (SEQ ID NO:19).
20) L37M-FGF9 DNA (SEQ ID NO:20).
21) hisR64M-FGF9 (SEQ ID NO:21).
22) FGF9-2 DNA (SEQ ID NO:22).
23) F72M-P189stop-F9 DNA (SEQ ID NO:23).
24) F72M-P191Stop-F9 DNA (SEQ ID NO:24).
25) R64M-P189Stop-F9 DNA (SEQ ID NO:25).
26) L66M-P191Stop-F9-2 DNA (SEQ ID NO:26)

A known fragment of FGF-9 (U.S. Pat. No. 5,512,460) is denoted herein as L54M-K196 Stop-FGF-9-Protein (SEQ ID NO:27).

The DNA sequence of this known fragment (U.S. Pat. No. 5,512,460) of FGF-9 is designated herein as L54M-K196 Stop-FGF-9-DNA (SEQ ID NO:28).

The methods of producing the mutants by Polymerase Chain Reaction (PCR) using specific mutual primers to incorporate the mutations encoding amino acid substitutions and to create the truncated variants, separation and purification of fragments on agarose gel, construction in an expression vector and transfection into host cells is disclosed.

By way of exemplification, the truncation of one currently most preferred embodiment denoted L37M-W144G-FGF9 was prepared by PCR using oligonucleotides designed to substitute a Met at position 37 for the Leu of the wild type FGF-9 thus initiating the transcription at position 37 and to incorporate an amino acid substitution at W144 thus replacing a Trp with a Gly. The resulting DNA sequence was cloned in an expression plasmid, which was used to transfect suitable host cells.

According to another aspect of the present invention it is disclosed that the preferred variant FGFs have improved therapeutic utility in diseases and disorders associated with FGF receptors. The therapeutic utility of these novel variants is disclosed in bone formation and fracture healing, cartilage repair as well as for diseases involving both normal and abnormal FGF receptors, including but not limited to skeletal disorders including but not limited to Achondroplasia, Hypochondroplasia, and osteoporosis.

The present invention further provides pharmaceutical compositions useful for the regulation of vasculogenesis or angiogenesis, and thus can be used for treating or diminishing malignant or benign tumors, tumor progression or to promote wound healing.

BRIEF DESCRIPTION OF THE FIGURES

FIGS. 1A and 1B depict alignment of the FGF core structures.

FIGS. 9A and 9B illustrate the results of treating a bone fracture with FGF-9 or L73M-W144G-FGF9. A) Autoradiograph analysis of callus formation as an index of bone healing at 4 weeks post operation (p.o.) untreated ulnas, treated with FGF-9 and HA or L37M-W144G-FGF9 (W144G) and HA. B) Level of bone mineral density as determined by DEXA (Dual X-ray Absorptiometry) at 4 weeks post surgery untreated ulnas, treated with FGF-9 and HA orL37M-W144G-FGF9 (W144G) and HA.

DETAILED DESCRIPTION OF THE PREFERRED EMBODIMENTS

Figure 6:
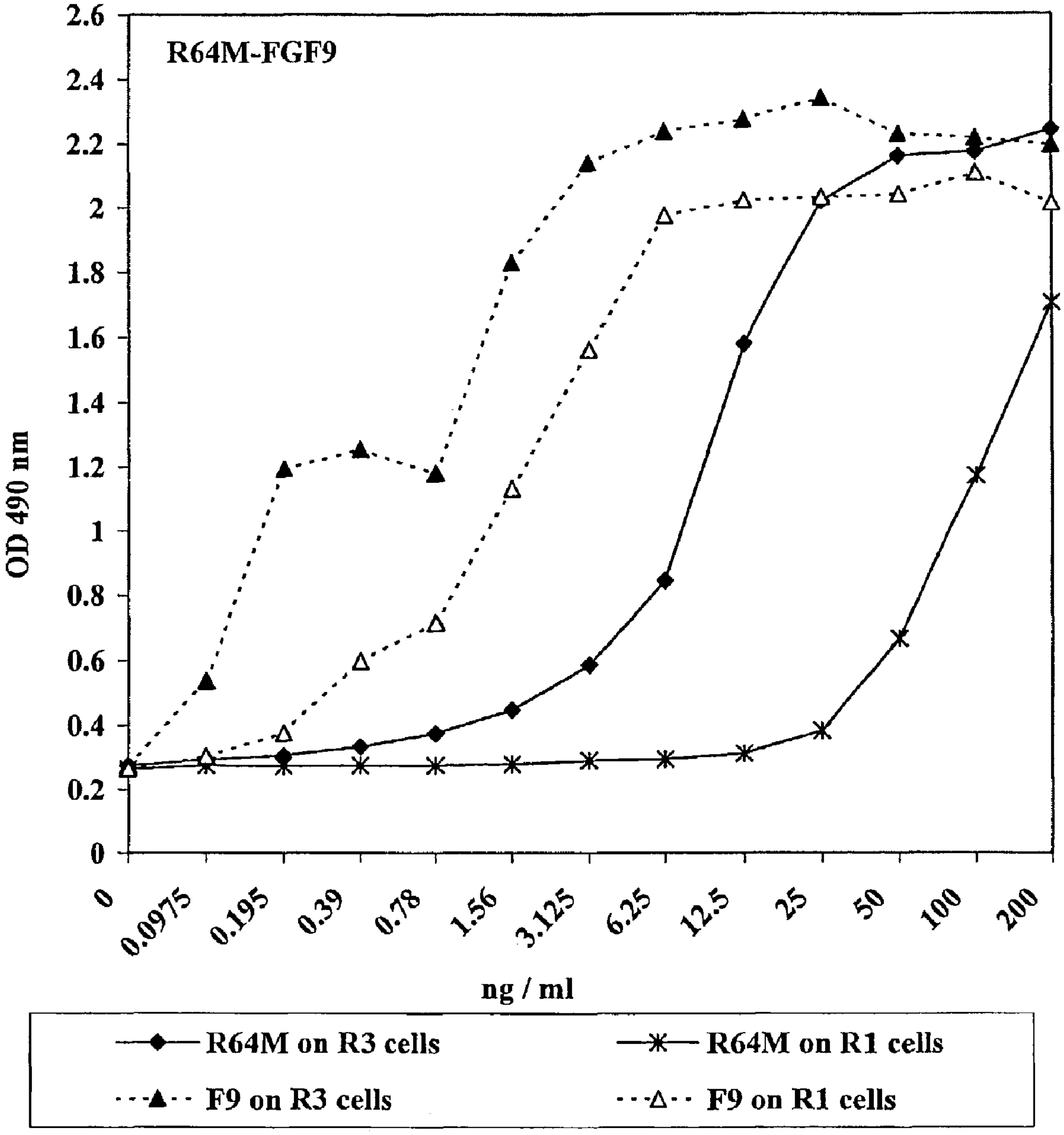
FIG. 6 shows the level of mitogenic activity induced by the R64M-FGF9 variant compared wild type FGF-9 on FGFR1 or FGFR3 transfected FDCP cells.

Fibroblast growth factors (FGFs) constitute a family of at least twenty-two structurally related, heparin binding polypeptides which are expressed in a wide variety of cells and tissues. Overall, the FGFs share between 17-72% amino acid sequence homology and a high level of structural similarity. A homology core of around 120 amino acids, of which six are identical and twenty-eight are highly conserved and has been identified in all members. The core domain comprises the residues that interact with both the FGFR and heparin. Twelve antiparallel β strands have been identified in the core structure, labeled β1 through β12, linked one to another by loops of variable lengths, organized into a trefoil internal symmetry (Faham, et al., Curr Opin Struc Biol 8, 578 1998). Sequence alignment and location and length of the β strands for FGF-1 through FGF-19 is depicted in FIG. 6 of Plotnikov et al. (Cell 101, 413, 2000). The core structure of the known FGFs is depicted in FIGS. 1A and 1B. The biological response of cells to FGF is mediated through specific, high affinity (Kd 20-500 pM) cell surface receptors that possess intrinsic tyrosine kinase activity and are phosphorylated upon binding of FGF (Coughlin et al. J Biol. Chem. 263, 988).

According to the principles of the present invention it is now disclosed that amino acid substitutions in the loop between the β8 and β9 strands of the core structure of the FGFs yield variants with altered specificity to FGFRs. Similarly, the core structure can be preserved while the carboxy and amino termini of the molecule are varied, thereby yielding active variants with improved properties. The variants thus obtained will have the inherent mitogenic properties of the FGF molecules but may be designed to have improved properties in terms of receptor specificity, stability or affinity. Furthermore, the variants so obtained may be advantageous in terms of their ability to be expressed using recombinant molecular biological techniques as are known in the art.

For convenience certain terms employed in the specification, examples and claims are described here.

As used herein and in the claims the term "FGFR" denotes a receptor specific for FGF which is necessary for transducing the signal exerted by FGF to the cell interior, typically comprising an extracellular ligand-binding domain, a single transmembrane helix, and a cytoplasmic domain that contains a tyrosine kinase activity.

As used herein and in the claims the term "active FGF" denotes any FGF molecule which after binding to an FGF receptor elicits stimulation of mitogenesis at least twice that of the same cells not exposed to said FGF molecule, as measured by methods known in the art.

As used herein and in the claims the term "FGF receptor specificity" denotes the fact that a certain FGF molecule binds to and activates a particular FGF receptor eliciting a biological response or affinity at least twice as high as its activity or affinity towards another FGFR. Biological responses and receptor affinity are measured by methods known in the art.

As used herein and in the claims the term "core", "core domain" or "core structure" denotes a region of homology of around 120 amino acids that is found in all native FGFs. Twenty eight amino acid residues are highly conserved and six are identical. Twelve structurally conserved anti-parallel β strands have been identified in all the FGFs. The core domain comprises the FGFR and heparin binding sites.

As used herein and in the claims the term "β8-β9" or "β8-β9 loop" refers to the loop of 2 to 5 amino acid residues that lie between the eighth and ninth β-pleated strands of the core structure as disclosed herein.

As used herein and in the claims the terms "amino terminus" and "N terminus" of a polypeptide may be used interchangeably. Similarly, the terms "carboxy terminus" and "C terminus" may be used interchangeably.

The term "variant" as used herein refers to a polypeptide sequence that possesses some modified structural property of the native protein. For example, the variant may be truncated at either the amino or carboxy termini or both termini or may have amino acids deleted or substituted. It may be antagonistic or agonistic with respect to normal properties of the native protein. An antagonist is defined as a substance that to some extent abolishes the action of another. An agonist is defined as a substance that induces a cellular or physiologic response. For example, a molecule that binds to a receptor and elicits a biological response. A biological response may be, for example, the stimulation of cell division, differentiation, angiogenesis or wound repair. A biological response may encompass other functional properties of the native protein and would be well known to those practicing the art. It is contemplated in this invention that a variant may have altered binding to a receptor than the native protein. This binding may enhance or depress a biological response. Accordingly, the variant may have altered specificity for one or more receptors.

The variant may be generated through recombinant DNA technologies, well known to those skilled in the art. As used herein, the term "polymerase chain reaction" ("PCR") refers to the methods disclosed in U.S. Pat. Nos. 4,683,195, 4,683,202, and 4,965,188, hereby incorporated by reference.

The term "expression vector" and "recombinant expression vector" as used herein refers to a recombinant DNA molecule containing a desired coding sequence and appropriate nucleic acid sequences necessary for the expression of the operably linked coding sequence in a particular host organism. The expression vector may comprise sequences encoding heterologous domains including but not limited to protein detection, purification or cleavage sequences that may be fused at the N- or C-terminus to the desired coding sequence, to yield a fusion protein. It is contemplated that the present invention encompasses expression vectors that are integrated into host cell genomes, as well as vectors that remain unintegrated into the host genome.

As used herein, the "amino acids" used in the invention are those which are available commercially or are available by routine synthetic methods. Certain amino acid residues may require special methods for incorporation into the peptide, and either sequential, divergent or convergent synthetic approaches to the peptide sequence are useful in this invention. Natural coded amino acids and their derivatives are represented by either the one-letter code or three-letter codes according to IUPAC conventions. When there is no indication, the L isomer was used. Other pharmaceutically active amino acids, including synthetic amino acids, are known in the art and are intended to be included in the invention.

FGF activity is conveniently determined using a series of biological assays performed in-vitro, ex-vivo and in vivo. These assays are used to demonstrate the activity elicited upon binding of FGF to its receptors. The biological assays routinely used to test activities of truncated FGFs include, but are not limited to, the following:

i. binding of variant FGFs to cloned FGF receptors expressed on immortalized cell lines, thereby eliciting a biological response including cell proliferation or inhibition of cell proliferation,
ii. binding to soluble receptors utilizing enzyme markers such as Alkaline Phosphatase,
iii. stimulation of bone growth in fetal bone cultures ex vivo,
iv. promotion of bone formation and fracture healing in animal models of bone growth and fractures.

Design of Variants

One currently preferred embodiment of the invention is an FGF molecule in which an amino acid substitution is incorporated into the β8-β9 loop. Structural data has recently identified that domain as a major binding site demonstrated to interact with the link connecting the Ig-like 2 (D2) and Ig-like 3 (D3) domains of the receptor (Plotnikov et al., Cell 98, 641 1999). Plotnikov et al., (Cell 101, 413, 2000) have shown that certain domains in the FGFR such as βC'-βE (D2-D3 linker) and βF-βG (of D3) regulate FGF-2 binding specificity by interacting with the β4-β5 loop and the amino terminus of FGF. The authors have further shown that a residue in β8-β9 of FGF-2, specifically Asn102, is involved in ligand/receptor interactions. Here we disclose Trp144 of FGF-9 as a contributor to specificity, thus replacing it with other amino acid residues affects ligand binding and receptor specificity.

In order to further understand the molecular basis for this specificity Hecht, Yayon and coworkers (Hecht et al., Acta Crystallogr. D. Biol. Crystallogr., 57, 378, 2001) have explored the three-dimensional structure of FGF-9. The elucidation of this crystal structure has clearly delineated the core structure of the FGF-9 molecule.

Superimposing FGF-9 on FGF-2 co-crystallized with FGFR1, show two major interfaces that appear different: the β8-β9 strands, which bind the inter-domain linker of D2 and D3 of the receptor, and the N-terminus helix, which sterically clashes with the receptor. These findings suggest accordingly that these regions would require major changes in backbone conformation to allow an engagement with FGFR1. Furthermore, FGF-9 amino acid residues predicted to bind the D3 domain show little conservation, which might point to increased specificity (Plotnikov et al, Cell 98, 641 1999; Plotnikov et al., Cell 101, 413, 2000). Table1 depicts the amino acid alignment of the residues in the β8-β9 loop of the known FGFs and 1-3 adjacent residues from the β strand on either side. The Trp 144 of FGF-9 is highlighted in bold and underlined.

TABLE 1

Amino acid sequence alignment of the β8-β9 residues

| | | |
|---|---|---|
| FGF-1 | LEENHYNTY | Residues:104-112 (SEQ ID NO:32) |
| FGF-2 | LESNNYNTY | Residues:107-115 (SEQ ID NO:33) |
| FGF-3 | IHELGYNTY | Residues:121-129 (SEQ ID NO:34) |
| FGF-4 | LLPNNYNAY | Residues:161-169 (SEQ ID NO:35) |
| FGF-5 | FQENSYNTY | Residues:166-174 (SEQ ID NO:36) |
| FGF-6 | LLPNNYNTY | Residues:163-171 (SEQ ID NO:37) |
| FGF-7 | ILENHYNTY | Residues:143-151 (SEQ ID NO:38) |
| FGF-8 | VLENNYTAL | Residues:151-159 (SEQ ID NO:39) |
| FGF-9 | FEEN**W**YNTY | Residues:140-148 (SEQ ID NO:40) |
| FGF-10 | IEENGYNTY | Residues:156-164 (SEQ ID NO:41) |
| FGF-11 | VFENYYVLY | Residues:149-157 (SEQ ID NO:42) |
| FGF-12 | VFENYYVIY | Residues:151-159 (SEQ ID NO:43) |
| FGF-13 | VFENYYVTY | Residues:147-155 (SEQ ID NO:44) |
| FGF-14 | VFENYYVIY | Residues:149-157 (SEQ ID NO:45) |
| FGF-15 | MDCLGYNQY | Residues:133-141 (SEQ ID NO:46) |
| FGF-16 | FEENWYNTY | Residues:139-147 (SEQ ID NO:47) |
| FGF-17 | VLENNYTAF | Residues:133-141 (SEQ ID NO:48) |
| FGF-18 | VLENNYTAL | Residues:133-141 (SEQ ID NO:49) |
| FGF-19 | IRPDGYNVY | Residues:126-134 (SEQ ID NO:50) |
| FGF-20 | FEENWYNTY | Residues:143-151 (SEQ ID NO:51) |
| FGF-21 | LLEDGYNVY | Residues:127-135 (SEQ ID NO:52) |
| FGF-22 | IEENGHNTY | Residues:119-127 (SEQ ID NO:53) |
| FGF-23 | TLENGYDVY | Residues:119-127 (SEQ ID NO:54) |
| FGF-CX | FEENWYNTY | Residues:143-151 (SEQ ID NO:55) |

Note: FGF-2 includes the 9 a.a. due to the propeptide sequences (Pro-FGF-2). Amino acid 107 would be 98 in the protein without the propeptide.

Sequence alignment for FGF-1-FGF-19 is according to Plotnikov et al. (Cell 101, 413, 2000). FGF-20-23 sequences were identified in Kirikoshi et al. (Biochem Biophys Res Commun 274, 337, 2000), Nishimura et al. (Biochim Biophys Acta 1492, 203, 2000), Nakatake et al. (Biochim Biophys Acta 1517, 460, 2001) and Yamashita et al. (Biochem Biophys Res Commun 277, 494, 2000), respectively. The FGF-CX sequence is disclosed in WO 01/07595.

Preferred Embodiments

Here we disclose increased receptor specificity of FGF-9 by amino acid substitutions in the β8-β9 loop between the strands. Introduction of glycine at position 144 of FGF-9 abolished its binding towards FGFR1 while retaining significant affinity towards FGFR3 and to a lesser extent, FGFR2. Furthermore, the L37M-W144G-FGF9 variant, featuring both the W144G mutation and a 36 amino acid truncation induces growth-arrest in RCS cells, which constitutively express FGFR2 and FGFR3 (Sahni, M. et al, Genes Devel. 13, 1361, 1999 and shown in FIG. 8). A significant decrease in the affinity of L37M-W144G-FGF9 towards the alternatively spliced variant of FGFR3IIIb was noted in a proliferation assay of FDCP cells expressing FGFR3IIIb. Although FGF-9 is a poor ligand of FGFR3IIIb, almost no mitogenic activity could be monitored by the L37M-W144G-FGF9 variant. Thus, the W144G-FGF9 mutant exhibits a higher specificity towards FGFR3IIIc as it loses binding to both FGFR1 and to the IIIb spliced isoform of FGFR3.

According to additional preferred embodiments, the FGF comprises the substitution of tryptophan 144(W144) of FGF-9 with either glycine (G), valine (V), glutamate (E) or arginine (R). W144 is located in β8-β9 with adjacent residues which are highly conserved among most FGFs. Substitution of aligned residues in FGF-2, exemplified by Asn 102 with Ala (N102A) (Zhu et al., Protein Eng, 10, 417, 1997) had no receptor specificity alterations. We generated variants with other substitutions at the W144 site and tested them for receptor specificity. The tryptophan was replaced with either Gly (G), Ala (A), Val (V), Asn (N), Glu (E) or Arg (R). The W144G, W144V, W144E and W144R variants showed diminished specificity towards FGFR1 and retention of specificity towards the FGFR3 receptor. The W144A or W144N variants behaved as native FGF-9. In addition, a substitution of the adjacent Asn at position 143 to a Ser, N143S, resulted in activation of FGFR3 and not FGFR1. Table 2 shows the specificity of the FGF variants to FDCP cells transfected with FGFR1 or FGFR3 as determined in a cell proliferation assay.

TABLE 2

Variant specificity towards FGFR1 or FGF3-expressing FDCP cells.

| Mutant | FGFR-1 | FGFR-3 |
|---|---|---|
| WT-FGF-9 | + | + |
| W144G-FGF-9 | − | + |
| W144A-FGF-9 | + | + |
| W144V-FGF-9 | − | + |
| W144N-FGF-9 | + | + |
| W144E-FGF-9 | − | + |
| W144R-FGF-9 | − | + |
| N143S-FGF-9 | − | + |

Figure 2:
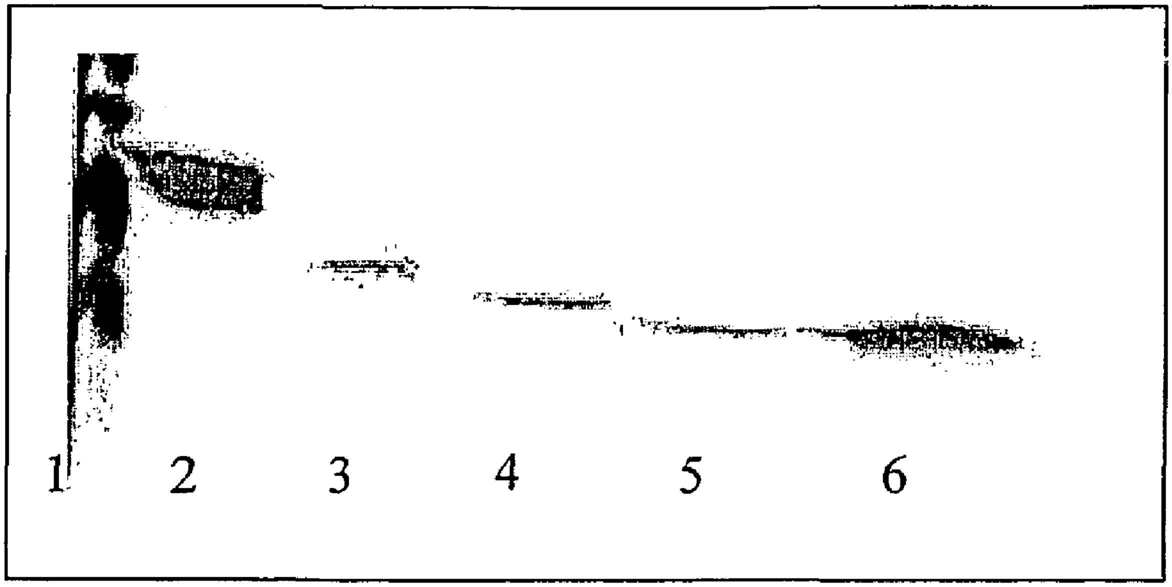
FIG. 2 displays the electrophoresis pattern of FGF-9 variants on SDS-PAGE.

FIG. 2 depicts the electrophoretic pattern of several of the preferred variants on SDS-PAGE. Lane 1 contains molecular weight markers [Lysozyme (20.7 kDa), Soybean trypsin inhibitor (28.8 kDa), Carbonic anhydrase (34.3 kDa), Ovalbumin (50 kDa)]; Lane 2 contains native FGF-9; Lane 3 contains the L37M-FGF9 variant; Lane 4 contains the L45M-FGF9 variant; Lane 5 contains the R64M-FGF9 variant; Lane 6 contains the FGF9-2 variant.

Figure 3:
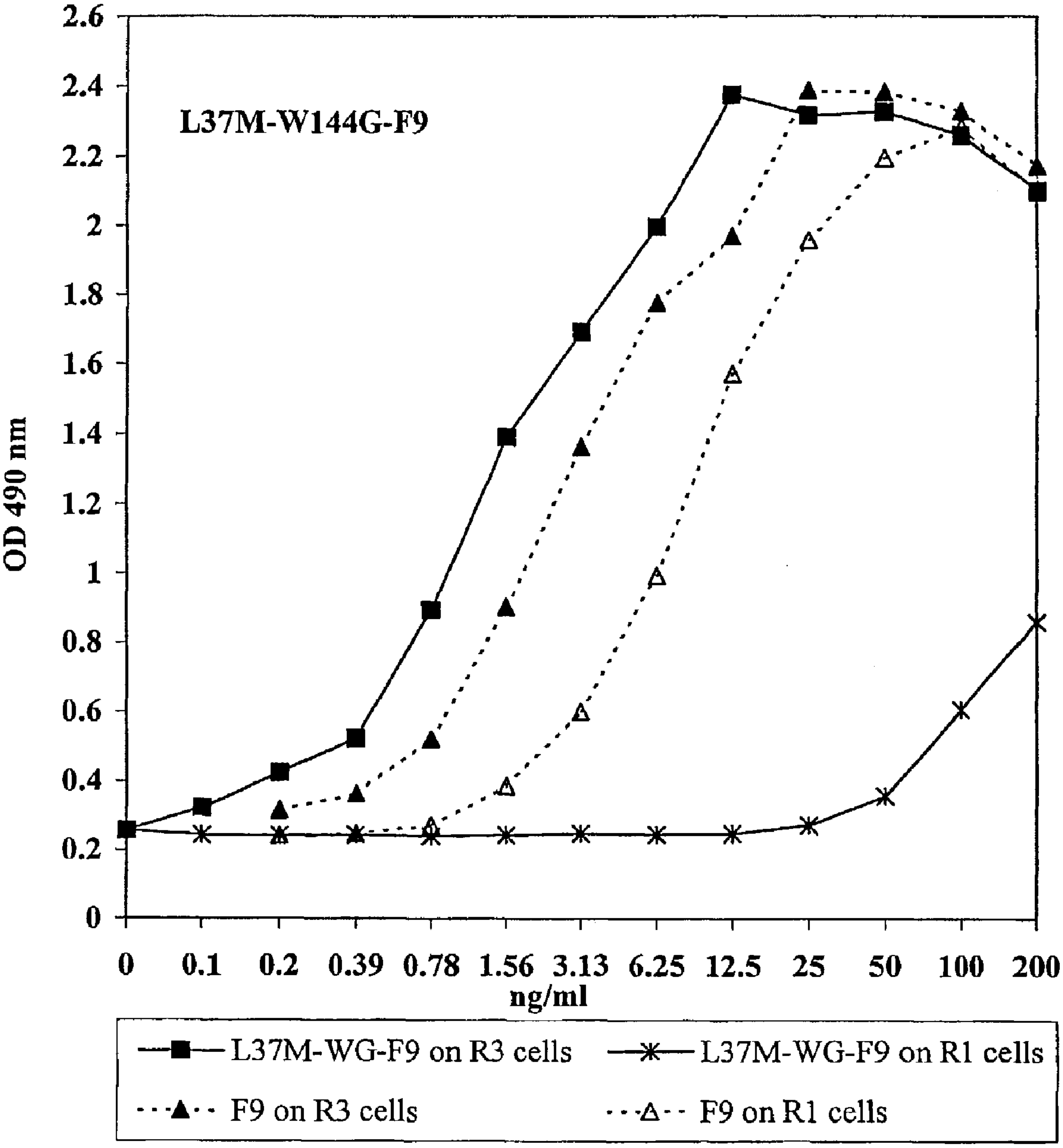
FIG. 3 shows the level of mitogenic activity induced by variant L37M-W 144G-FGF9 compared to wild type FGF-9 on FGFR1 or FGFR3 transfected FDCP cells.
Figure 4:
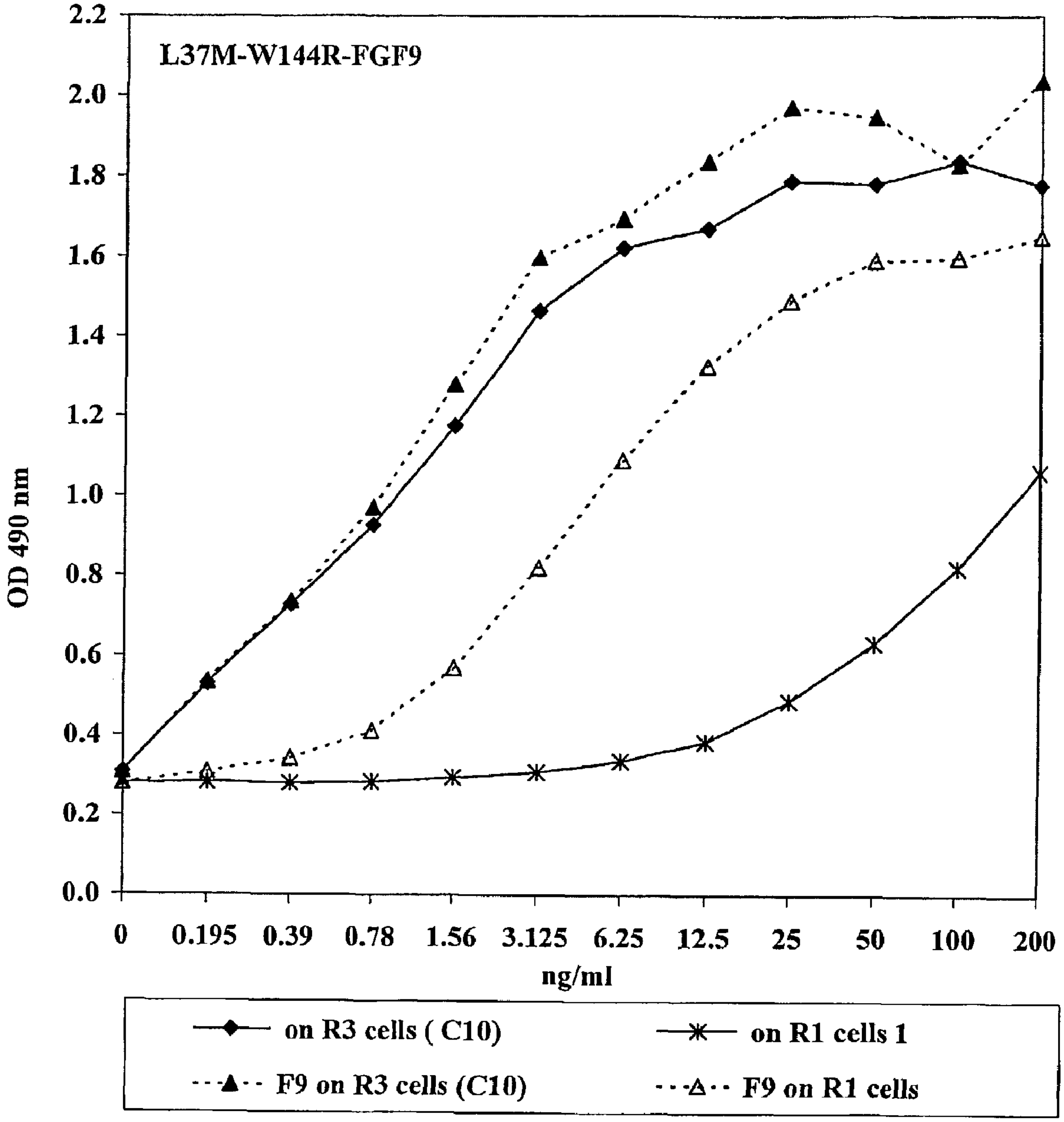
FIG. 4 shows the level of mitogenic activity induced by variant L37M-W144R-FGF9 compared to wild type FGF-9 on FGFR1 or FGFR3 transfected FDCP cells.
Figure 5:
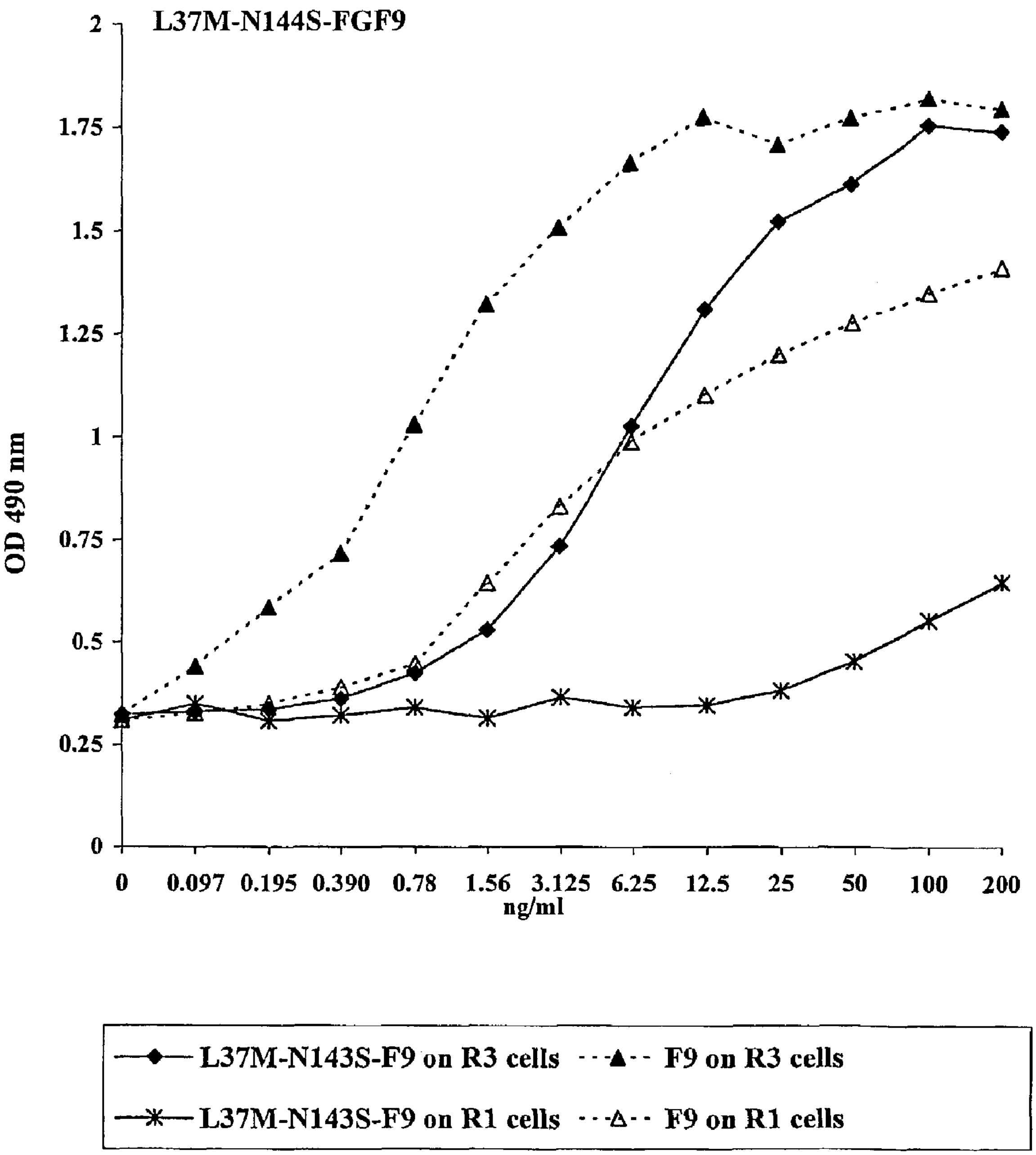
FIG. 5 shows the level of mitogenic activity induced by variant L37M-N143S-FGF9 compared to wild type FGF-9 on FGFR1 or FGFR3 transfected FDCP cells.

In a preferred embodiment of the present invention, the variant comprises one or more amino acid substitutions in the β8-β9 loop and a truncation at either or both the N or C terminus. These variants would be advantageous in terms of their stability and/or solubility and receptor affinity and specificity. FIGS. 3, 4 and 5 show the increased level of mitogenic activity of certain preferred variants in a proliferation assay in FGFR1 or FGFR3-transfected FDCP cells. The X axis in all figures is concentration of FGF-9 or variant measured in ng/ml, while the Y axis depicts absorbtion at 490 nm and reflects mitogenicity. The L37M-W144G-FGF9 variant (FIG. 3) elicits a biological response similar to FGF-9 on FGFR3-expressing cells but at a lower concentration and fails to elicit a response at less that 50 ng/ml on the FGFR1-expressing cells. The L37M-W144R-FGF9 variant and FGF-9 (FIG. 4) display a similar biological response on FGFR3 expressing cells but said variant elicits a poor response on FGFR1 expressing cells. The L37M-N143S-FGF9 variant (FIG. 5), induces a lower level of mitogenicity than FGF-9, however it too displays a loss of specificity to the FGFR1 while maintaining specificity for the FGFR3. An active variant will elicit a mitogenic response through a specific receptor at a level not to be lower than two-fold of that of the corresponding native FGF at a concentration not higher than 50-fold of that of the native FGF, more preferably not higher than 20-fold and most preferably not higher than 10-fold than that of the native FGF receptor ligand. In order to further understand the molecular basis for this specificity Hecht, Yayon and coworkers (Hecht et al., Acta Crystallogr. D. Biol. Crystallogr., 57, 378, 2001) have explored the three-dimensional structure of FGF-9. The elucidation of this crystal structure has clearly delineated the core structure of the FGF-9 molecule. The active variants according to the present invention now provide the shortest active fragments which retain the selectivity and affinity of the intact FGF-9. It is now disclosed that a series of truncation variants was prepared and tested for FGF activity. Among these mutants some were found to be more active than the parent molecule, while others were as active as the parent FGF molecule, whereas others were less active or inactive. The present invention further discloses the DNA sequences of FGF-9 variants, as well as the polypeptides expressed.

Currently preferred embodiments include the two active variants of FGF-9 denoted herein as R64M-FGF9 and hisR64M-FGF9, the amino acid sequences of which are represented as SEQ ID NO:5 and SEQ ID NO:8, respectively. The corresponding polynucleotide sequences of these two active variants are represented by SEQ ID NO:18 and SEQ ID NO:21, respectively.

Figure 7:
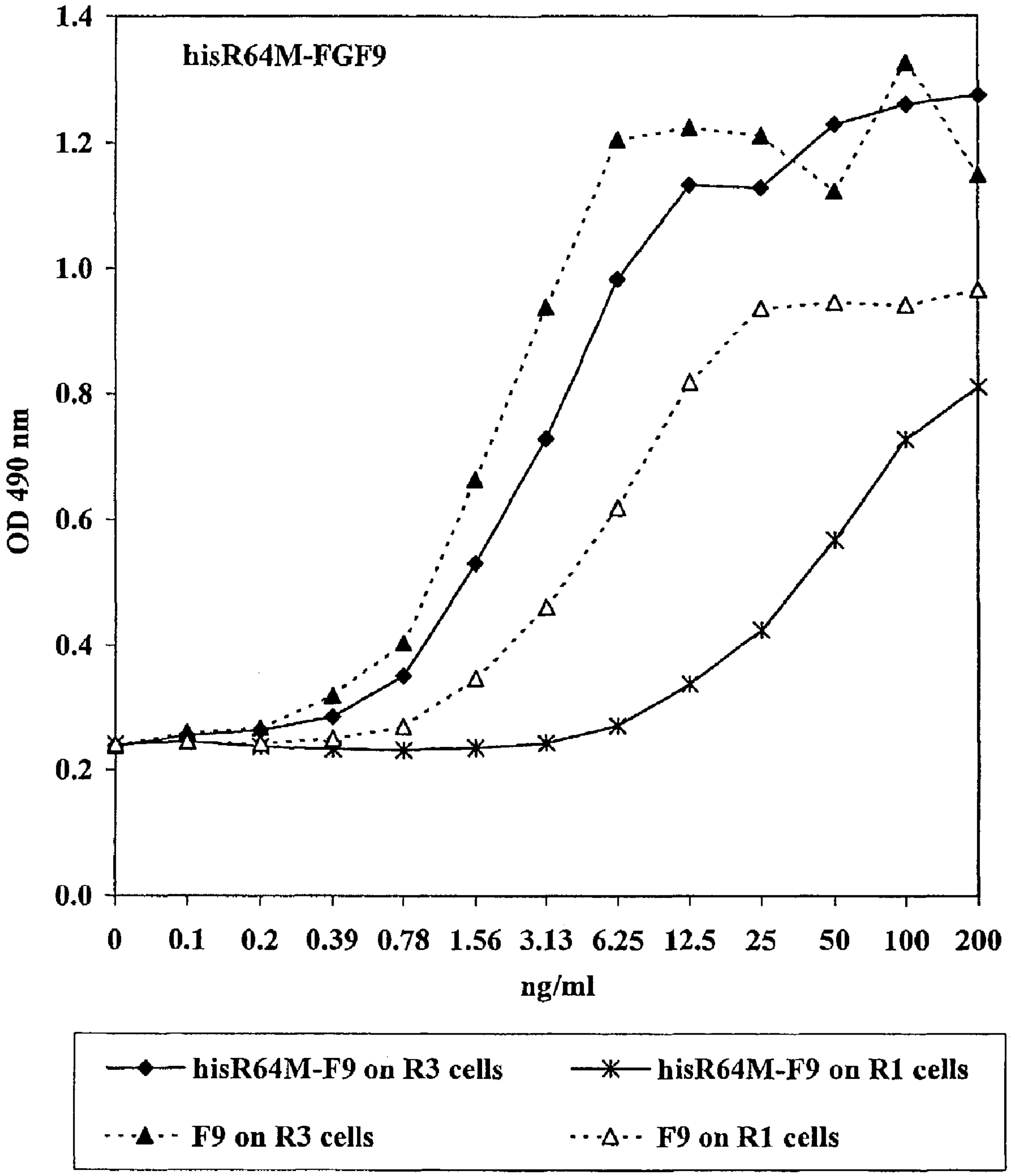
FIG. 7 shows the level of mitogenic activity induced by the hisR64M-FGF9 variant compared wildtype FGF-9 on FGFR1 or FGFR3 transfected FDCP cells.

Upon removal of amino acid residues near and into the core structure, the FGF protein loses receptor binding capacity. FGF9-2, a 127 aa variant of the invention represented as SEQ ID NO:9 has reduced mitogenic capacity relative to wild type FGF-9. The R64M-FGF9 variant of 145 aa, represented as SEQ ID NO:5, provides the shortest FGF-9 polypeptide that retains binding specificity toward FGFR3 and has lost the binding capacity toward FGFR1, as determined in a mitogenic assay. The hisR64M-FGF9 variant, represented as SEQ ID NO:8, which includes a heterologous 16 amino acid stretch fused to the 145 polypeptide of R64M-FGF9, and retains the same level of receptor specificity. FIG. 6 shows that although the mitogenic activity of R64M-FGF9 is reduced in comparison to that of wild type FGF-9 the variant retains high specificity towards FGFR3 and does not elicit a response through FGFR1. FIG. 7 depicts the significant increase in mitogenic activity of hisR64M-FGF9 while preserving FGFR3 specificity.

Currently more preferred embodiments include the active variants of FGF-9 denoted herein as W144X-FGF9 and L37-W144X-FGF9, the amino acid sequences of which are represented as SEQ ID NO:1 and SEQ ID NO:2, respectively, wherein X is other than tryptophan and the corresponding polynucleotide sequences of these two variants are represented by SEQ ID NO:14, and SEQ ID NO:15. Currently most preferred embodiments include the active variants of FGF-9 denoted herein as W144G-FGF9, W144R-FGF9, L37M-W144G-FGF9 and L37M-W144R-FGF9.

Additional more preferred embodiments include the active variants denoted herein as N143X-FGF9 and L37-N143X-FGF9, the amino acid sequences of which are represented as SEQ ID NO:3 and SEQ ID NO:4 respectively, wherein X is other than aparagine and the corresponding polynucleotide sequences of these two variants are represented by SEQ ID NO:16, and SEQ ID NO:17. Currently most preferred embodiments include the active variants of FGF-9 denoted herein as N143S-FGF9 and L37-N143S-FGF9.

Additional FGF variants, represented as SEQ ID NOS: 10-13 with corresponding polynucleotide SEQ ID NOS:23-26, have been shown to have reduced mitogenic activity.

Methods of Producing and Using Variants

Figure 8:
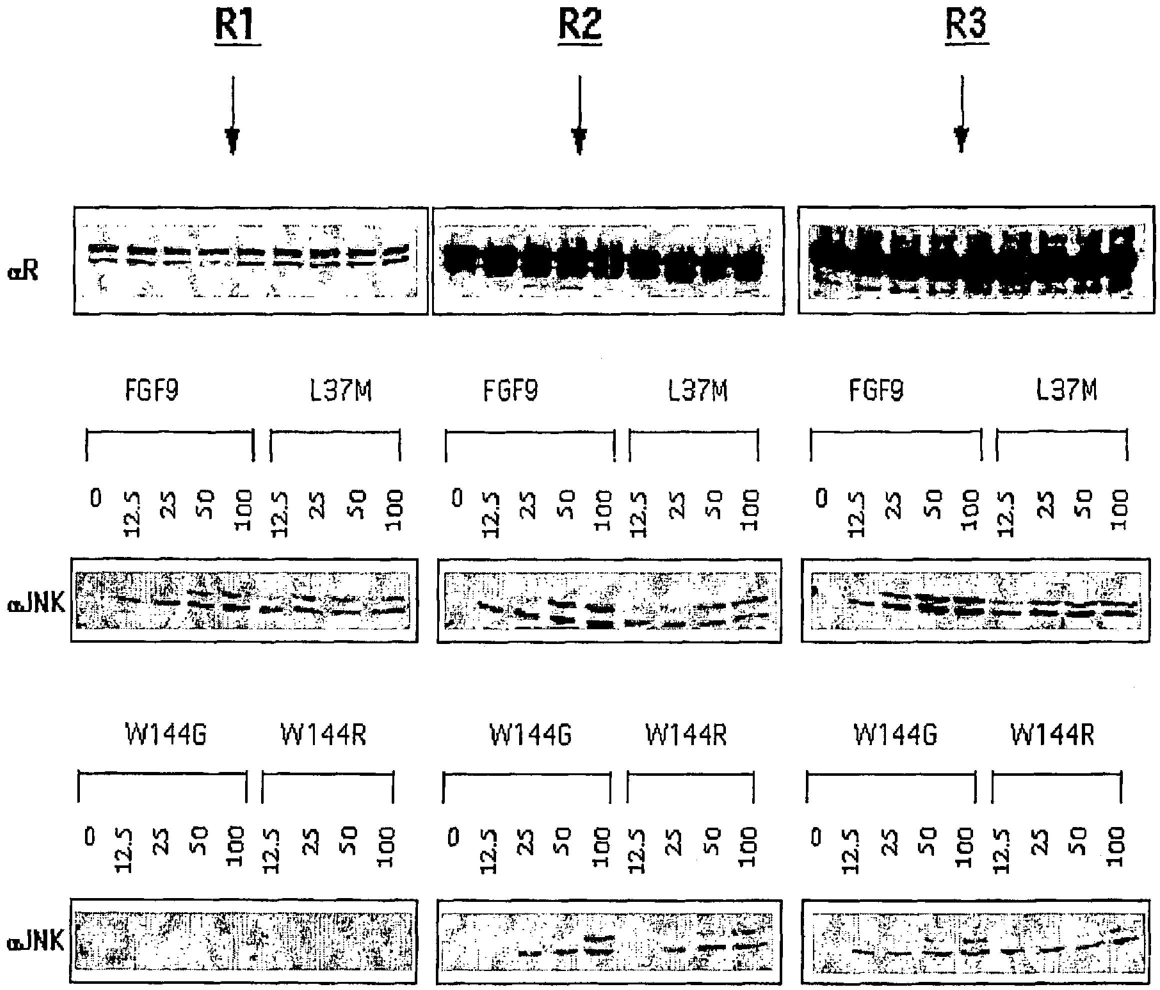
FIG. 8 shows FGF/FGFR-dependent JNK activation signal transduction in a Western assay using anti-diphosphorylated JNK antibodies.

The L37M-W144G-FGF9 variant and a corresponding L37M-W144R-FGF9 variant, wherein an arginine substitution at the W144 position, were tested for JNK activation in RCS cells. FIG. 8 depicts Western blot assays of the relative activity of the a sample of the variants as viewed with an anti-activated JNK antibody. Jnk (Jun kinase) is a serine/threonine kinase activated in response to receptor tyrosine kinase activation, as that of the FGFRs. RCJ cells constitutively express relatively high levels of FGFR2 and FGFR3 and low levels of FGFR1 (row labeled as αR). JNK activation was induced by the wild type FGF-9 (FGF-9) and the L37M-FGF9 (L37M) variant at comparable levels. Conversely, JNK activation by the L37M-W144G-FGF9 and L37M-W144R-FGF9 variants was abolished with respect to the FGFR1 and only slightly reduced with respect to FGFR2 and 3. These results demonstrate the loss of binding of the variants to the FGFR1 and retaining of binding to FGFR3.

The most preferred method for producing the variants is through recombinant DNA technologies, well known to those skilled in the art. For example, the variants may be prepared by Polymerase Chain Reaction (PCR) using specific primers for each of the truncated forms or the amino acid substitutions as disclosed herein below. The PCR fragments may be purified on an agarose gel and the purified DNA fragment may be cloned into an expression vector and transfected into host cells. The host cells may be cultured and the protein harvested according to methods known in the art. According to another aspect of the present invention it is disclosed that the preferred variant FGFs have improved therapeutic utility in diseases and disorders involving FGF receptors.

The therapeutic utility of these novel mutants is disclosed for both normal and abnormal FGF receptors, including but not limited to malignant cells overexpressing FGFR receptors, Achondroplasia, Hypochondroplasia, (a condition associated with moderate but variable, disproportionate shortness of limbs), Osteoporosis, as well as in bone fracture healing and bone growth.

FIGS. 9A and 9B show the results of treating a bone fracture with L37M-W144G-FGF9 (W144G) compared to untreated and FGF-9 alone. Two parameters are given, the autoradiograph over the course of 4 weeks post osteotomy (p.o.) (FIG. 9A) and the level of bone mineral density at 4 weeks p.o (FIG. 9B). Following two weeks a large callus was observed in the W144G treated ulna, with a smaller one seen in FGF9 treated animals and none in the untreated animals.

Figure 10:
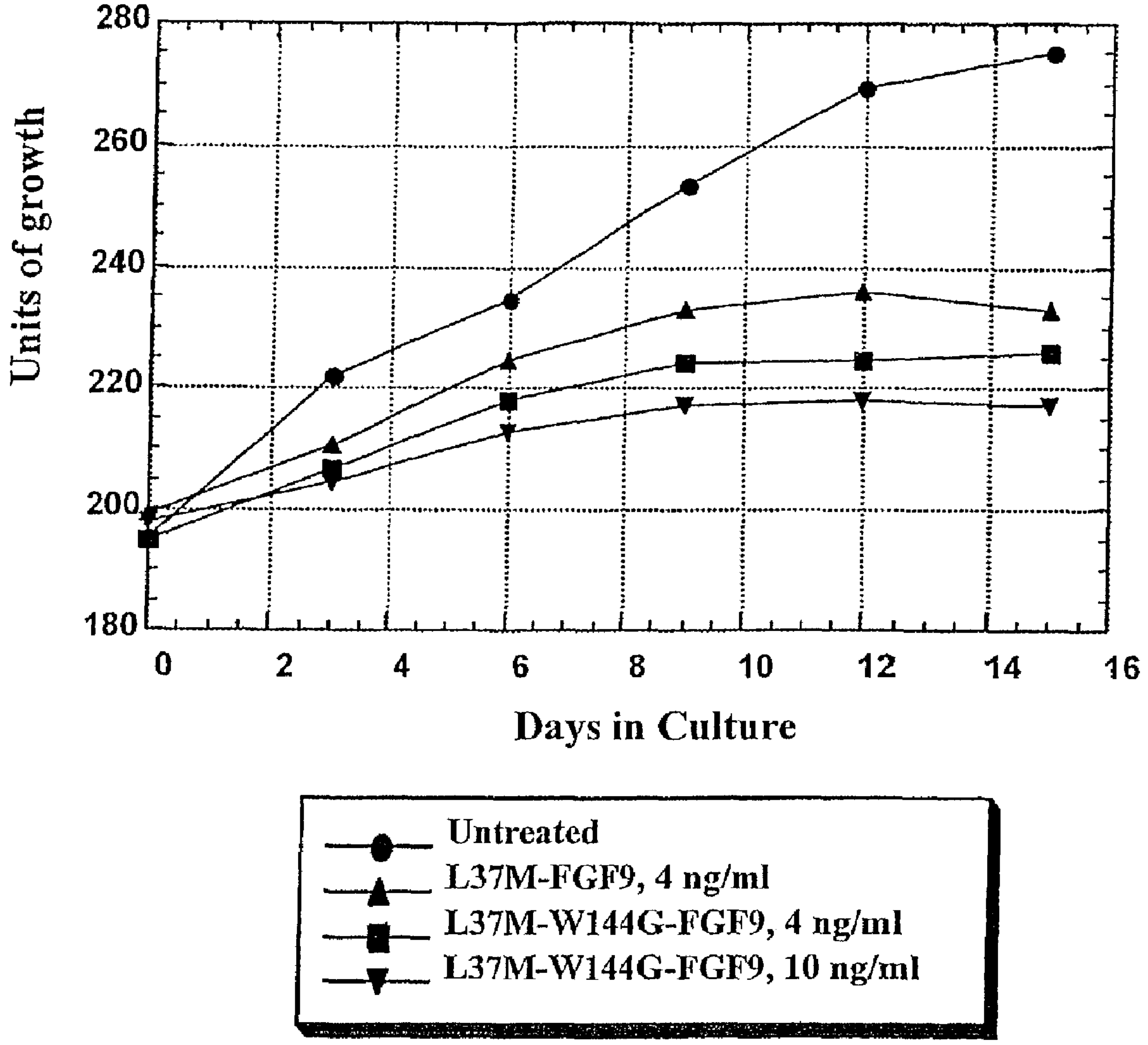
FIG. 10 shows the effect of the L37M-FGF9 and L37M-W144G-FGF9 variants on femoral growth, ex vivo.

FIG. 10 shows the enhanced inhibition of growth induced by the L37M-FGF9 and L37M-W144G-FGF9 variants in ex vivo cultured femoras of wild type mice. The rationale is that an active FGF variant will activate an FGF receptor and mimic the constitutively up-regulated FGFR3 seen in Achondroplasia resulting in bone growth inhibition. Bone growth in the untreated femora is seen as the circles. Bone growth inhibition is enhanced by the L37M-FGF9 variant (triangle ▲) and more so by the L37M-W144G-FGF9 variant (square ■ and reversed triangle ▼).

Figure 11:
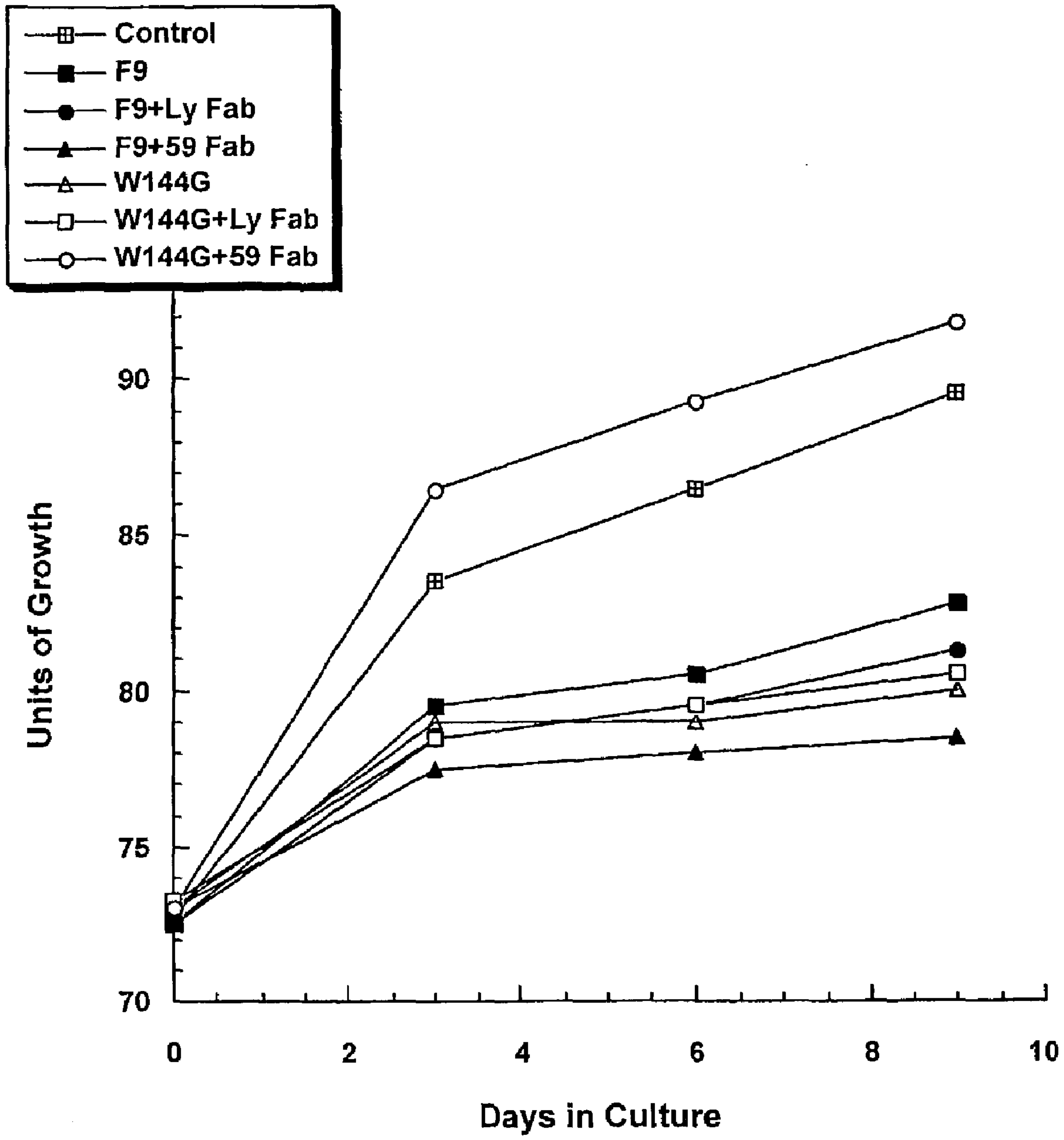
FIG. 11 depicts the effect of the FGFR3 neutralizing antibody, MSPRO-59 Fab fragment, on L37M-W144G-FGF9 induced femur growth inhibition.

In an experiment designed to demonstrate the receptor specificity of the variants, the effect of the variants on femoral growth inhibition was tested in the presence of an FGFR3 neutralizing antibody. The antibody, an Fab fragment identified in a phage display library and denoted MSPRO-59, was shown to bind specifically to FGFR3IIIb and c and neutralize their activity. FIG. 11 depicts growth inhibition in femoras from wild type mice induced by FGF-9, known to bind and activate FGFR3 and FGFR1, and a variant of the invention, L37-W144G-FGF9. Growth is inhibited in the samples induced by FGF-9 and MSPRO-59; although FGFR3 is neutralized FGFR1 is activated by FGF-9. Conversely the femoras exposed to L37-W 144G-FGF9 and MSPRO-59 grow normally since the antibody neutralizes FGFR3 and the variant cannot activate FGFR1.

According to currently more preferred embodiments it is possible to target drugs and other bioactive molecules, including but not limited to cytotoxic drugs, to cells bearing FGFR3 without appreciably affecting cells bearing FGFR1. This is accomplished by conjugating the drug of choice to a variant FGF of the invention. According to even more preferred embodiments of the present invention it is now possible to target drugs and other bioactive molecules, including but not limited to cytotoxic drugs, to one or more specific subtype of FGFR2 and/or FGFR3. Most preferred embodiments of the invention are particularly useful in conjugates with drugs for inhibiting cell proliferation and facilitating or enhancing the treatment of defects or tumors bearing a specific receptor subtype, without interfering with the growth of normal cells or tissues bearing other receptor subtypes. In a non-limiting example, L37M-W144G-FGF9 targeting compositions can comprise a L37M-W144G-FGF9 component and cytotoxin that are covalently bound to each other. For example, a L37M-W144G-FGF9 targeting composition can comprise a L37M-W144G-FGF9 conjugate. One example of a L37M-W144G-FGF9 conjugate is L37M-W144G-FGF9-saporine conjugate, another example is a conjugate with a tyrosine inhibitor such as, but not limited to, genistein.

Alternatively, L37M-W144G-FGF9 targeting compositions can comprise a L37M-W144G-FGF9 targeting fusion protein. Illustrative fusion proteins include polypeptides comprising a cytotoxin selected from the group consisting of type-I ribosome-inactivating protein, *Staphylococcal enterotoxin-A, diphtheria toxin, Pseudomonas exotoxin*, and *Pseudomonas endotoxin*. In another variation, the L37M-W144G-FGF9 targeting compositions comprise a L37M-W144G-FGF9 liposome.

Pharmacology

Apart from other considerations, the fact that the novel active ingredients of the invention are polypeptides dictates that the formulation be suitable for delivery of this type of compounds. Clearly, peptides are less suitable for oral administration due to susceptibility to digestion by gastric acids or intestinal enzymes. Specific formulations may be designed to circumvent these problems, including enterocoating, gelatin capsules, emulsions and the like. Nevertheless, bioavailability is impaired by poor gastrointestinal absorption and the routes of administration are preferably parenteral. The preferred routes of administration are intra-articular, intravenous, intramuscular, subcutaneous, intradermal, or intrathecal. A more preferred route is by direct injection at or near the site of disorder or disease.

As used herein a "pharmaceutical composition" refers to a preparation of one or more of the active variant selected from the sequences, SEQ ID NO:1 through SEQ ID NO:13 described herein, or physiologically acceptable salts or prodrugs thereof, with other chemical components such as physiologically suitable carriers and excipients. The purpose of a pharmaceutical composition is to facilitate administration of a compound to an organism.

The term "prodrug" refers to an agent, which is converted into an active parent drug in vivo. Prodrugs are often useful because in some instances they may be easier to administer than the parent drug. They may, for instance, be bioavailable by oral administration whereas the parent drug is not. The prodrug may also have improved solubility compared to the parent drug in pharmaceutical compositions.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols. Pharmaceutical compositions may also include one or more additional active ingredients.

Pharmaceutical compositions of the present invention may be manufactured by processes well known in the art, e.g., by means of conventional mixing, dissolving, granulating, grinding, pulverizing, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants for example DMSO, or polyethylene glycol are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration. For buccal administration, the compositions may take the form of tablets or lozenges formulated in conventional manner.

For administration by inhalation, the variants for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insulator may be formulated containing a powder mix of the peptide and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances which increase the viscosity of the suspension, including but not limited to natural substances and polymers such as collagen, sorbitol, dextran or hyaluronic acid (HA) and derivatives, synthetic polymers, cellulose derivatives including sodium carboxymethyl cellulose (CMC) and derivatives of said substances or any natural or synthetic carrier known in the art (Pillai and Panchagnula, Curr. Opin. Chem. Biol. 5, 447, 2001) Optionally, the suspension may also contain suitable stabilizers or agents, which increase the solubility of the compounds, to allow for the preparation of highly concentrated solutions. Alternatively, the active ingredient may be in powder form for reconstitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The formulations of the active variants may be administered topically as a gel, ointment, cream, emulsion or sustained release formulation including a transdermal patch. The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

For bone or tissue repair, administration may be preferred locally by means of a direct injection at or near the site of target or by means of a subcutaneous implant, staples or slow release formulation implanted at or near the target.

Pharmaceutical compositions suitable for use in context of the present invention include compositions wherein the active ingredients are contained in an amount effective to achieve the intended purpose. More specifically, a therapeutically effective amount means an amount of a compound effective to prevent, alleviate or ameliorate symptoms of a disease of the subject being treated. Determination of a therapeutically effective amount is well within the capability of those skilled in the art, especially in light of the detailed disclosure provided herein.

Toxicity and therapeutic efficacy of the peptides described herein can be determined by standard pharmaceutical procedures in cell cultures or experimental animals, e.g., by determining the $IC_{50}$ (the concentration which provides 50% inhibition) and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (e.g., Fingl, et al., 1975, in "The Pharmacological Basis of Therapeutics", Ch. 1 p.1).

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on the subject being treated, the severity of the affliction, the manner of administration, the judgment of the prescribing physician, and all other relevant factors.

The following example is an illustration only of a method of treating a subject with a variant according to the invention, in order to treat a pathological condition associated with tissue trauma or a related condition, and is not intended to be limiting.

The method includes the step of administering the active variant, in a pharmaceutically acceptable carrier as described above, to a subject to be treated. The medicament is administered according to an effective dosing methodology, preferably until a predefined endpoint is reached, such as a reduction or amelioration of the pathological condition in the subject.

The present invention also relates to methods of treatment of the various pathological conditions described above, by administering to a patient a therapeutically effective amount of the compositions of the present invention. The term administration as used herein encompasses oral, parenteral, intravenous, intramuscular, subcutaneous, transdermal, intrathecal, rectal and intranasal administration.

The present invention further relates to method for the use of the active FGF variants to prepare medicaments useful in inducing bone formation and fracture healing as well as in the detection and treatment of various FGFR-related disorders including skeletal disorders such as achondroplasia and thanatophoric dysplasia and certain types of cancer including but not limited to transitional cell carcinoma (TCC) of the bladder, multiple myeloma, chronic myeloid leukemia (CML) and cervical carcinoma.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification. In addition, citation or identification of any reference in this application shall not be construed as an admission that such reference is available as prior art to the present invention.

The following sequences are preferred embodiments according to the invention. Amino acid substitutions are marked in bold and underlined. The sequences listed are according to the human FGF-9; the amino acid changes for mouse FGF-9 are Asn9Ser and Ser34Asn, similarly the amino acid changes for the chicken FGF-9 are Val24Ala, Val27Ala, Ser40Ala and Lys87Gln.

Those skilled in the art will recognize that the polynucleotide sequences disclosed in SEQ ID NOs: 14-26 represent a single allele of the human FGF-9 gene and polypeptide, and that allelic variation are expected to occur. Allelic variants can be cloned by probing cDNA or genomic libraries or be generated by PCR from total RNA, cDNA or genomic DNA from different individuals according to standard procedures. Allelic variants of the polynucleotide sequence, including those containing silent mutations and those in which mutations result in amino acid sequence changes, are within the scope of the present invention, as are proteins which are allelic variants of SEQ ID NOS:1-13 and SEQ ID NOS:29-31.

Protein Sequence of Human W144X-FGF9 (SEQ ID NO: 1)

1 Met Ala Pro Leu Gly Glu Val Gly Asn Tyr Phe Gly Val Gln Asp 15 16 Ala Val Pro Phe Gly Asn Val Pro Val Leu Pro Val Asp Ser Pro 30 31 Val Leu Leu Ser Asp His Leu Gly Gln Ser Glu Ala Gly Gly Leu 45 46 Pro Arg Gly Pro Ala Val Thr Asp Leu Asp His Leu Lys Gly Ile 60 61 Leu Arg Arg Arg Gln Leu Tyr Cys Arg Thr Gly Phe His Leu Glu 75 76 Ile Phe Pro Asn Gly Thr Ile Gln Gly Thr Arg Lys Asp His Ser 90 91 Arg Phe Gly Ile Leu Glu Phe Ile Ser Ile Ala Val Gly Leu Val 105 106 Ser Ile Arg Gly Val Asp Ser Gly Leu Tyr Leu Gly Met Asn Glu 120 121 Lys Gly Glu Leu Tyr Gly Ser Glu Lys Leu Thr Gln Glu Cys Val 135 136 Phe Arg Glu Gln Phe Glu Glu Asn Xaa Tyr Asn Thr Tyr Ser Ser 150 151 Asn Leu Tyr Lys His Val Asp Thr Gly Arg Arg Tyr Tyr Val Ala 165 166 Leu Asn Lys Asp Gly Thr Pro Arg Glu Gly Thr Arg Thr Lys Arg 180 181 His Gln Lys Phe Thr His Phe Leu Pro Arg Pro Val Asp Pro Asp 195 196 Lys Val Pro Glu Leu Tyr Lys Asp Ile Leu Ser Gln Ser wherein Xaa is other than Trp and more preferably selected from Gly, Arg, Glu or Val.

Protein Sequence of L37M-W144X-FGF9 172aa (SEQ ID NO: 2)

Met Gly Gln Ser Glu Ala Gly Gly Leu Pro Arg Gly Pro Ala Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Xaa Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser wherein Xaa is other than Trp and more preferably selected from Gly, Arg, Glu or Val.

Protein Sequence of N143X-FGF9 208aa (SEQ ID NO: 3)

Met Ala Pro Leu Gly Glu Val Gly Asn Tyr Phe Gly Val Gln Asp Ala Val Pro Phe Gly Asn Val Pro Val Leu Pro Val Asp Ser Pro Val Leu Leu Ser Asp His Leu Gly Gln Ser Glu Ala Gly Gly Leu Pro Arg Gly Pro Ala Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Xaa Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser wherein Xaa is other than Asn and more preferably Ser.

Protein Sequence of L37M-N143X-FGF9 172aa (SEQ ID NO:4)

Met Gly Gln Ser Glu Ala Gly Gly Leu Pro Arg Gly Pro Ala Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu

Glu Xaa Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser

Wherein Xaa is other than Asn and more preferably Ser.

Additional preferred embodiments according to the invention:

Protein Sequence of R64M-FGF9 145aa (SEQ ID NO:5)

Met Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser

Protein Sequence of L45M-FGF9 164aa (SEQ ID NO:6)

Met Pro Arg Gly Pro Ala Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser

Protein Sequence of L37M-FGF9 172aa (SEQ ID NO:7)

Met Gly Gln Ser Glu Ala Gly Gly Leu Pro Arg Gly Pro Ala Val Thr Asp Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp Lys Val Pro Glu Leu Tyr Lys Asp Ile Leu Ser Gln Ser

Protein Sequence of hisR64M-FGF9 161aa (SEQ ID NO:8)

His His His His His His Ser Ser Gly Leu Val Pro Arg Gly Ser His Met Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Vat Asp Pro Asp Lys Val Pro Glu Leu Tyr Lys Asp Ile Leu Ser Gln Ser

The core of approximately 120 amino acids of FGF (amino acids 66-190 of FGF-9) has been shown to be crucial for FGF function. The following examples, in which truncations were extended into the core, having decreased activity include:

Protein Sequence of FGF9-2 127aa (SEQ ID NO:9)

Met Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg

Protein Sequence of F72M-P189stop-F9 117aa (SEQ ID NO:10)

Met His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu

Protein Sequence of F72M-Pro191Stop-F9 119aa (SEQ ID NO:11)

Met His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg

Protein Sequence of R64M-P189Stop-F9 125aa (SEQ ID NO:12)

Met Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu

Protein Sequence of L66M-191Stop-F9-2 125aa (SEQ ID NO:13)

Met Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg

The corresponding polynucleotide sequences of the preferred embodiments are disclosed as follows:

DNA Sequence of W144X-FGF9 (SEQ ID NO:14)

```
ATGGCTCCCT TAGGTGAAGT TGGGAACTAT TTCGGTGTGC AGGATGCGCT ACCGTTTGGG  60
AATGTGCCCG TGTTGCCGGT GGACAGCCCG GTTTTGTTAA GTGACCACCT GGGTCAGTCC  120
GAAGCAGGGG GGCTCCCCAG GGGACCCGCA GTCACGGACT TGGATCATTT AAAGGGGATT  180
CTCAGGCGGA GGCAGCTATA CTGCAGGACT GGATTTCACT TAGAAATCTT CCCCAATGGT  240
ACTATCCAGG GAACCAGGAA AGACCACAGC CGATTTGGCA TTCTCGAATT TATCAGTATA  300
GCAGTGGGCC TGGTCAGCAT TCGAGGCGTG GACAGTCGAC TCTACCTCGG GATGAATGAG  360
AAGGGGGAGC TGTATGGATC AGAAAAACTA ACCCAAGAGT GTGTATTCAG AGAACAGTTC  420
GAAGAAAACX XXTATAATAC GTACTCGTCA AACCTATATA AGCACGTGGA CACTGGAAGG  480
CGATACTATG TTGCATTAAA TAAAGATGGG ACCCCGAGAG AAGGGACTAG GACTAAACGG  540
CACCAGAAAT TCACACATTT TTTACCTAGA CCAGTGGACC CCGACAAAGT ACCTGAACTG  600
TATAAGGATA TTCTAAGCCA AAGTTGA 62
```

Wherein XXX is other than a codon coding for Trp (TGG) or a stop codon (TAA, TAG or TGA) and is more preferably a codon coding for amino acid Gly, Arg, Val, or Glu DNA Sequence of Human L37M-W144X-FGF9 DNA (SEQ ID NO:15)

```
                                                    AT GGGTCAGTCC  120
GAAGCAGGGG GGCTCCCCAG GGGACCCGCA GTCACGGACT TGGATCATTT AAAGGGGATT  180
CTCAGGCGGA GGCAGCTATA CTGCAGGACT GGATTTCACT TAGAAATCTT CCCCAATGGT  240
ACTATCCAGG GAACCAGGAA AGACCACAGC CGATTTGGCA TTCTGGAATT TATCAGTATA  300
GCAGTGGGCC TGGTCAGCAT TCGAGGCGTG GACAGTGGAC TCTACCTCGG GATGAATGAG  360
AAGGGGGAGC TGTATGGATC AGAAAAACTA ACCCAAGAGT GTGTATTCAG AGAACAGTTC  420
GAAGAAAACX XXTATAATAC GTACTCGTCA AACCTATATA AGCACGTGGA CACTGGAAGG  480
CGATACTATG TTGCATTAAA TAAAGATGGG ACCCCGAGAG AAGGGACTAG GACTAAACGG  540
CACCAGAAAT TCACACATTT TTTACCTAGA CCAGTGGACC CCGACAAAGT ACCTGAACTG  600
TATAAGCATA TTCTAAGCCA AAGTTGA 627
```

Wherein XXX is other than a codon coding for Trp (TGG) or a stop codon (TAA, TAG or TGA) and is more preferably a codon coding for amino acid Gly, Arg, Val, or Glu DNA Sequence of N143X-FGF9 (SEQ ID NO:16)

```
ATGGCTCCCT TAGGTGAAGT TGGGAACTAT TTCGGTGTGC AGGATGCGGT ACCGTTTGGG  60
AATGTGCCCG TGTTGCCCGT GGACAGCCCG GTTTTGTTAA GTGACCACCT GGGTCAGTCC  120
GAAGCAGGGG GGCTCCCCAG GGGACCCGCA GTCACGGACT TGGATCATTT AAAGGGGATT  180
CTCAGGCGGA GGCAGCTATA CTGCAGGACT GGATTTCACT TAGAAATCTT CCCCAATGGT  240
ACTATCCAGG GAACCAGGAA AGACCACAGC CGATTTGGCA TTCTGGAATT TATCAGTATA  300
GCAGTGGGCC TGGTCAGCAT TCGACGCGTG CACAGTGGAC TCTACCTCGG GATGAATGAG  360
AAGGGGGAGC TGTATGGATC AGAAAAACTA ACCCAAGAGT GTGTATTCAG AGAACAGTTC  420
GAAGAAXXXT GGTATAATAC GTACTCGTCA AACCTATATA AGCACGTGGA CACTGGAAGG  480
```

-continued

```
CGATACTATG TTGCATTAAA TAAAGATGGG ACCCCGAGAG AAGGGACTAG CACTAAACGG  540

CACCAGAAAT TCACACATTT TTTACCTAGA CCAGTGGACC CCGACAAAGT ACCTGAACTG  600

TATAAGGATA TTCTAAGCCA AAGTTGA 627
```

wherein XXX is other than a codon coding for asparagine (AAC, AAC) or a stop codon (TAA, TAG or TGA).

DNA Sequence of Human L37M-N143X-FGF9 DNA (SEQ ID NO:17)

```
                                                    A_T GGGTCAGTCC 120

GAAGCAGGGG GGCTCCCCAG GGGACCCGCA GTCACGGACT TGGATCATTT AAAGGGGATT  180

CTCAGGCGGA GGCAGCTATA CTGCAGGACT GGATTTCACT TAGAAATCTT CCCCAATGGT  240

ACTATCCAGG GAACCAGGAA AGACCACAGC CGATTTGGCA TTCTGGAATT TATCAGTATA  300

GCAGTGGGCC TGGTCAGCAT TCGAGGCGTG GACAGTGGAC TCTACCTCGG GATGAATGAG  360

AAGGGGGAGC TGTATGGATC AGAAAAACTA ACCCAAGAGT GTGTATTCAG AGAACAGTTC  420

GAAGAAXXXT GGTATAATAC GTACTCGTCA AACCTATATA AGCACGTGGA CACTGGAAGG  480

CGATACTATG TTGCATTAAA TAAAGATGGG ACCCCGAGAG AAGGGACTAG GACTAAACGG  540

CACCAGAAAT TCACACATTT TTTACCTAGA CCAGTGGACC CCGACAAAGT ACCTGAACTG  600

TATAAGGATA TTCTAAGCCA AAGTTGA 627
```

wherein XXX is other than a codon coding for asparagine (AAC, AAC) or a stop codon (TAA, TAG or TGA).

DNA sequence of R64M-FGF9-DNA (SEQ ID NO:18)

```
                                                            A

TGCAGCTATA CTGCAGGACT GGATTTCACT TAGAAATCTT CCCCAATGGT ACTATCCAGG

GAACCAGGAA AGACCACAGC CGATTTGGCA TTCTGGAATT TATCAGTATA GCAGTGGGCC

TGGTCAGCAT TCGAGGCGTG GACAGTGGAC TCTACCTCGG GATGAATGAG AAGGGGGAGC

TGTATGGATC AGAAAAACTA ACCCAAGAGT GTGTATTCAG AGAACAGTTC GAAGAAAACT

GGTATAATAC GTACTCGTCA AACCTATATA AGCACGTGGA CACTGGAAGG CGATACTATG

TTGCATTAAA TAAAGATGGG ACCCCGAGAG AAGGGACTAG GACTAAACGG CACCAGAAAT

TCACACATTT TTTACCTAGA CCAGTGGACC CCGACAAAGT ACCTGAACTG TATAAGGATA

TTCTAAGCCA AACTTGA
```

DNA sequence of L45M-FGF9-DNA (SEQ ID NO:19)

```
           ATGCCCAG GGGACCCGCA GTCACCGACT TGGATCATTT AAAGGGGATT

CTCAGGCGGA GGCAGCTATA CTGCAGGACT GGATTTCACT TAGAAATCTT CCCCAATGGT

ACTATCCAGG GAACCAGGAA AGACCACAGC CCATTTGGCA TTCTGGAATT TATCAGTATA

GCAGTGGGCC TGGTCAGCAT TCGAGGCGTG GACAGTGGAC TCTACCTCGG GATGAATGAG

AAGGGGGAGC TGTATGGATC AGAAAAACTA ACCCAAGAGT GTGTATTCAG AGAACAGTTC

GAAGAAAACT GGTATAATAC GTACTCGTCA AACCTATATA AGCACGTGGA CACTGGAAGG

CGATACTATG TTGCATTAAA TAAAGATGGG ACCCCGAGAG AAGGGACTAG GACTAAACGG
```

-continued

CACCAGAAAT TCACACATTT TTTACCTAGA CCAGTGGACC CCGACAAAGT ACCTGAACTG

TATAAGGATA TTCTAAGCCA AAGTTGA 627

DNA sequence of L37M-FGF9-DNA (SEQ ID NO:20)

AT

GGGTCAGTCC GAAGCAGGGG GGCTCCCCAG GGGACCCGCA GTCACGGACT TGGATCATTT

AAAGGGGATT CTCAGGCGGA GGCAGCTATA CTGCAGGACT GGATTTCACT TAGAAATCTT

CCCCAATGGT ACTATCCAGG GAACCAGGAA AGACCACAGC CGATTTGGCA TTCTGGAATT

TATCAGTATA GCAGTGGGCC TGGTCAGCAT TCGAGGCGTG GACAGTGGAC TCTACCTCGG

GATGAATGAG AAGGGGGAGC TGTATGGATC AGAAAAACTA ACCCAAGAGT GTGTATTCAG

AGAACAGTTC GAAGAAAACT GGTATAATAC CTACTCGTCA AACCTATATA AGCACGTGGA

CACTGGAAGG CGATACTATG TTGCATTAAA TAAAGATGGG ACCCCGAGAG AAGGGACTAG

GACTAAACGG CACCAGAAAT TCACACATTT TTTACCTAGA CCAGTGGACC CCGACAAAGT

ACCTGAACTG TATAAGGATA TTCTAAGCCA AAGTTGA

DNA sequence of hisR64M-FGF-DNA (SEQ ID NO:21)

CATCAT CATCATCATC ACAGCAGCGG CCTGGTGCCG CGCGGCAGCCAT A

TGCAGCTATA CTGCAGGACT GGATTTCACT TAGAAATCTT CCCCAATGGT ACTATCCAGG

GAACCAGGAA AGACCACAGC CGATTTGGCA TTCTGGAATT TATCAGTATA GCAGTGGGCC

TGGTCAGCAT TCGAGGCGTG GACAGTGGAC TCTACCTCCG GATGAATGAG AAGGGGGAGC

TGTATGGATC AGAAAAACTA ACCCAAGAGT GTGTATTCAG AGAACAGTTC GAAGAAAACT

GGTATAATAC GTACTCGTCA AACCTATATA AGCACGTGGA CACTGGAAGG CGATACTATG

TTGCATTAAA TAAAGATGGG ACCCCGAGAG AAGGGACTAG GACTAAACGG CACCAGAAAT

TCACACATTT TTTACCTAGA CCAGTGGACC CCGACAAAGT ACCTGAACTG TATAAGGATA

TTCTAAGCCA AAGTTGA

DNA sequence of FGF9-2-DNA (SEQ ID NO:22)

A

TGCAGCTATA CTGCAGGACT GGATTTCACT TAGAAATCTT CCCCAATGGT ACTATCCAGG

GAACCAGGAA ACACCACAGC CGATTTGGCA TTCTGGAATT TATCAGTATA GCAGTGGGCC

TGGTCAGCAT TCGAGGCGTG GACAGTGGAC TCTACCTCGG GATGAATGAG AAGGGGGAGC

TGTATGGATC AGAAAAACTA ACCCAAGAGT GTGTATTCAG AGAACAGTTC GAAGAAAACT

GGTATAATAC GTACTCGTCA AACCTATATA ACCACGTGGA CACTGGAAGG CGATACTATG

TTGCATTAAA TAAAGATGGG ACCCCGAGAG AAGGGACTAG GACTAAACGG CACCAGAAAT

TCACACATTT TTTACCTAGA TGA

DNA sequence of F72M-P189stop-F9-DNA (SEQ ID NO:23)

ATGCACT TAGAAATCTT CCCCAATGGT

ACTATCCAGG GAACCAGGAA AGACCACAGC CGATTTGGCA TTCTGGAATT TATCAGTATA

GCAGTGGGCC TGGTCAGCAT TCGAGGCGTG GACAGTGGAC TCTACCTCGG GATGAATGAG

AAGGGGGAGC TGTATGGATC AGAAAAACTA ACCCAAGAGT GTGTATTCAG AGAACAGTTC

GAAGAAAACT GGTATAATAC GTACTCGTCA AACCTATATA AGCACGTGGA CACTGGAAGG

CGATACTATG TTGCATTAAA TAAAGATGGG ACCCCGAGAG AAGGGACTAG GACTAAACGG

CACCAGAAAT TCACACATTT TTTATGA

-continued

DNA sequence of F72H-P191Stop-F9-DNA (SEQ ID NO:24)

ATGCACT TAGAAATCTT CCCCAATGGT ACTATCCAGG

GAACCAGGAA AGACCACAGC CGATTTGGCA TTCTGGAATT TATCAGTATA GCAGTGGGCC

TGGTCAGCAT TCGAGGCGTC GACAGTGGAC TCTACCTCGG GATGAATGAG AAGGGGGAGC

TGTATGGATC AGAAAAACTA ACCCAAGAGT GTGTATTCAG AGAACAGTTC GAAGAAAACT

GGTATAATAC GTACTCGTCA AACCTATATA AGCACGTGGA CACTGGAAGG CGATACTATG

TTGCATTAAA TAAAGATGGG ACCCCGAGAG AAGGGACTAG GACTAAACGG CACCAGAAAT

TCACACATTT TTTACCTAGA TGA

DNA sequence of R64M-P189Stop-F9-DNA (SEQ ID NO:25)

A

TGCAGCTATA CTGCAGGACT GGATTTCACT TAGAAATCTT CCCCAATGGT ACTATCCAGG

GAACCAGGAA AGACCACAGC CGATTTGGCA TTCTGGAATT TATCAGTATA GCAGTGGGCC

TGGTCAGCAT TCGAGGCGTG GACAGTGCAC TCTACCTCGG GATGAATGAG AAGGGGGAGC

TGTATGGATC AGAAAAACTA ACCCAAGAGT GTGTATTCAG AGAACAGTTC GAAGAAAACT

GGTATAATAC GTACTCGTCA AACCTATATA AGCACGTGGA CACTGGAAGG CGATACTATG

TTGCATTAAA TAAAGATGGG ACCCCGAGAG AAGCGACTAG GACTAAACGG CACCAGAAAT

TCACACATTT TTTATGA

DNA sequence of L66M-P191Stop-F9-DNA (SEQ ID NO:26)

ATGTA CTGCAGGACT GGATTTCACT TAGAAATCTT CCCCAATGGT

ACTATCCAGG GAACCAGGAA AGACCACAGC CGATTTGGCA TTCTGGAATT TATCAGTATA

GCAGTGGGCC TGGTCAGCAT TCGAGGCGTG GACAGTGGAC TCTACCTCGG GATGAATGAG

AAGGGGGAGC TGTATGGATC AGAAAAACTA ACCCAAGAGT GTGTATTCAG AGAACAGTTC

GAAGAAAACT GGTATAATAC GTACTCGTCA AACCTATATA AGCACGTGGA CACTGGAAGG

CGATACTATG TTGCATTAAA TAAAGATGGG ACCCCGAGAG AAGGGACTAG GACTAAACGG

CACCAGAAAT TCACACATTT TTTACCTAGA TGA

The Polypeptide Sequence of L54M-K196Stop-FGF-9 U.S. Pat. No. 5,512,460 KNOWN FRAGMENT) (SEQ ID NO:27)

Leu Asp His Leu Lys Gly Ile Leu Arg Arg Arg Gln Leu Tyr Cys Arg Thr Gly Phe His Leu Glu Ile Phe Pro Asn Gly Thr Ile Gln Gly Thr Arg Lys Asp His Ser Arg Phe Gly Ile Leu Glu Phe Ile Ser Ile Ala Val Gly Leu Val Ser Ile Arg Gly Val Asp Ser Gly Leu Tyr Leu Gly Met Asn Glu Lys Gly Glu Leu Tyr Gly Ser Glu Lys Leu Thr Gln Glu Cys Val Phe Arg Glu Gln Phe Glu Glu Asn Trp Tyr Asn Thr Tyr Ser Ser Asn Leu Tyr Lys His Val Asp Thr Gly Arg Arg Tyr Tyr Val Ala Leu Asn Lys Asp Gly Thr Pro Arg Glu Gly Thr Arg Thr Lys Arg His Gln Lys Phe Thr His Phe Leu Pro Arg Pro Val Asp Pro Asp

The Polynucleotide Sequence of L54M-K196Stop-FGF-9 U.S. Pat. No. 5,512,460 KNOWN FRAGMENT) (SEQ ID NO:28)

A TGGATCATTT

AAAGGGGATT CTCAGGCGGA GGCAGCTATA CTGCAGGACT GGATTTCACT TAGAAATCTT

CCCCAATGGT ACTATCCAGG GAACCAGGAA AGACCACAGC CGATTTGGCA TTCTCGAATT

TATCAGTATA GCAGTGGGCC TGGTCAGCAT TCGAGGCGTG GACAGTGGAC TCTACCTCGG

GATGAATGAG AAGGGGGAGC TGTATGGATC AGAAAAACTA ACCCAAGAGT GTGTATTCAG

AGAACAGTTC GAAGAAAACT GGTATAATAC GTACTCGTCA AACCTATATA AGCACGTGGA

-continued

```
CACTGGAAGG CGATACTATG TTGCATTAAA TAAAGATGGG ACCCCGAGAG AAGGGACTAG

GACTAAACGG CACCAGAAAT TCACACATTT TTTACCTAGA CCAGTGGACC CCGACTGA
```

The human, mouse and chicken FGF-9 sequences are shown for comparative purposes only. Amino acid difference between the mouse and chicken and the human sequences are marked in bold and underlined.

Protein Sequence of Human FGF-9 (SEQ ID NO:29)

1 Met Ala Pro Leu Gly Glu Val Gly Asn Tyr Phe Gly Val Gln Asp 15 16 Ala Val Pro Phe Gly Asn Val Pro Val Leu Pro Val Asp Ser Pro 30 31 Val Leu Leu Ser Asp His Leu Gly Gln Ser Glu Ala Gly Gly Leu 45 46 Pro Arg Gly Pro Ala Val Thr Asp Leu Asp His Leu Lys Gly Ile 60 61 Leu Arg Arg Arg Gln Leu Tyr Cys Arg Thr Gly Phe His Leu Glu 75 76 Ile Phe Pro Asn Gly Thr Ile Gln Gly Thr Arg Lys Asp His Ser 90 91 Arg Phe Gly Ile Leu Glu Phe Ile Ser Ile Ala Val Gly Leu Val 105 106 Ser Ile Arg Gly Val Asp Ser Gly Leu Tyr Leu Gly Met Asn Glu 120 121 Lys Gly Glu Leu Tyr Gly Ser Glu Lys Leu Thr Gln Glu Cys Val 135 136 Phe Arg Glu Gln Phe Glu Glu Asn Trp Tyr Asn Thr Tyr Ser Ser 150 151 Asn Leu Tyr Lys His Val Asp Thr Gly Arg Arg Tyr Tyr Val Ala 165 166 Leu Asn Lys Asp Gly Thr Pro Arg Glu Gly Thr Arg Thr Lys Arg 180 181 His Gln Lys Phe Thr His Phe Leu Pro Arg Pro Val Asp Pro Asp 195 196 Lys Val Pro Glu Leu Tyr Lys Asp Ile Leu Ser Gln Ser

Protein Sequence of Mouse FGF-9 (SEQ ID NO:30)

1 Met Ala Pro Leu Gly Glu Val Gly Ser Tyr Phe Gly Val Gln Asp 15 16 Ala Val Pro Phe Gly Asn Val Pro Val Leu Pro Val Asp Ser Pro 30 31 Val Leu Leu Asn Asp His Leu Gly Gln Ser Glu Ala Gly Gly Leu 45 46 Pro Arg Gly Pro Ala Val Thr Asp Leu Asp His Leu Lys Gly Ile 60 61 Leu Arg Arg Arg Gln Leu Tyr Cys Arg Thr Gly Phe His Leu Glu 75 76 Ile Phe Pro Asn Gly Thr Ile Gln Gly Thr Arg Lys Asp His Ser 90 91 Arg Phe Gly Ile Leu Glu Phe Ile Ser Ile Ala Val Gly Leu Val 105 106 Ser Ile Arg Gly Val Asp Ser Gly Leu Tyr Leu Gly Met Asn Glu 120 121 Lys Gly Glu Leu Tyr Gly Ser Glu Lys Leu Thr Gln Glu Cys Val 135 136 Phe Arg Glu Gln Phe Glu Glu Asn Trp Tyr Asn Thr Tyr Ser Ser 150 151 Asn Leu Tyr Lys His Val Asp Thr Gly Arg Arg Tyr Tyr Val Ala 165 166 Leu Asn Lys Asp Gly Thr Pro Arg Glu Gly Thr Arg Thr Lys Arg 180 181 His Gln Lys Phe Thr His Phe Leu Pro Arg Pro Val Asp Pro Asp 195 196 Lys Val Pro Glu Leu Tyr Lys Asp Ile Leu Ser Gln Ser

Protein Sequence of Chicken FGF-9 (SEQ ID NO:31)

1 Met Ala Pro Leu Gly Glu Val Gly Asn Tyr Phe Gly Val Gln Asp 15 16 Ala Val Pro Phe Gly Asn Val Pro Ala Leu Pro Ala Asp Ser Pro 30 31 Val Leu Leu Ser Asp His Leu Gly Gln Ala Glu Ala Gly Gly Leu 45 46 Pro Arg Gly Pro Ala Val Thr Asp Leu Asp His Leu Lys Gly Ile 60 61 Leu Arg Arg Arg Gln Leu Tyr Cys Arg Thr Gly Phe His Leu Glu 75 76 Ile Phe Pro Asn Gly Thr Ile Gln Gly Thr Arg Gln Asp His Ser 90 91 Arg Phe Gly Ile Leu Glu Phe Ile Ser Ile Ala Val Gly Leu Val 105 106 Ser Ile Arg Gly Val Asp Ser Gly Leu Tyr Leu Gly Met Asn Glu 120 121 Lys Gly Glu Leu Tyr Gly Ser Glu Lys Leu Thr Gln Glu Cys Val 135 136 Phe Arg Glu Gln Phe Glu Glu Asn Trp Tyr Asn Thr Tyr Ser Ser 150 151 Asn Leu Tyr Lys His Val Asp Thr Gly Arg Arg Tyr Tyr Val Ala 165 166 Leu Asn Lys Asp Gly Thr Pro Arg Glu Gly Thr Arg Thr Lys Arg 180 181 His Gln Lys Phe Thr His Phe Leu Pro Arg Pro Val Asp Pro Asp195 196 Lys Val Pro Glu Leu Tyr Lys Asp Ile Leu Ser Gln Ser

The principles of the invention are demonstrated by means of the following non-limitative examples.

EXAMPLE 1

Expression of FGF Variants Using High Expression System Construction of the p89Bluescript (p89BS) Construct Construction of p89BS was performed by a series of digestions of *T. brockii* (TB) genomic DNA, with restriction endonucleases, as described below. The TB adh gene was located on an EcoRi digest (2700 bp), and the altered fragment was first cloned into the EcoRI site of pBluescriptII. XbaI digestion of a positive clone produced a smaller (1673 bp) DNA fragment containing the entire TB adh gene, which was ligated to XbaI-digested pBluescriptII to form the plasmid pBS-M105/2. The insert included the DNA encoding the 352 amino acid residues of TBADH and flanking regions of 249 nucleotides upstream of the initiation codon and 342 nucleotides downstream of (and including) the termination codon. PBS-P89 was a deletion mutant in which the upstream region was limited to 89 bases preceding the initiation codon for the TB adh gene. This shortened fragment was cloned into the SacI-XbaI sites of pBluescriptII SK(+). Using site directed mutagenesis, the sequence ATGATG was mutated into CATATG, thus creating an NdeI site at the 5' starting codon. A GGATCC BamHI site was constructed right after the TGA stop codon, thus forming unique NdeI-BamHI sites, compatible with the pET vector systems. PCR-generated DNA fragments encompassing the coding region of a number of proteins and variants were produced having NdeI and BamHI sites at the 5' and 3' ends respectively. The genes encoding the tested proteins were ligated into the NdeI-BamHI digest of p89BS construct transformed into *E. coli* cells, such as JM109, TG1, TG2, DHα, and XL1blue.

Construction of FGF Variants

Construction of the FGF-9 variants was performed using PCR technique. Three constitutive PCR reactions were performed, where the variation or variations were introduced into the gene by amplifying DNA fragments from both ends of the mutation site(s). The primers used for the human variants were as follows:

```
WG-for           5'-CGAAGAAAACGGGTATAATACGTAC-3'          (SEQ ID NO: 56)
WG-back          5'-GTACGTATFATACCCGTTTTCTTCG-3'          (SEQ ID NO:57)
WR-for           5'-CGAAGAAAACCGGTATAATACG-3'             (SEQ ID NO:58)
WR-back          5'-CGTATTATACCGGTTTTCTTCG-3'             (SEQ ID NO:59)
WV-for           5'-CGAAGAAAACGTGTATAATACG-3'             (SEQ ID NO:60)
WV-back          5'-CGTATTATACACGYITITCTTCG-3'            (SEQ ID NO:61)
WE-for           5'-CGAAGAAAACGAGTATAATACG-3'             (SEQ ID NO:62)
WE-back          5'-CGTATTATACTCGTTTTCTTCG-3'             (SEQ ID NO:63)
WA-for           5'-CGAAGAAAACGCGTATAATACG-3'             (SEQ ID NO:64)
WA-back          5'-CGTATTATACGCGTTTTCTTCG-3'             (SEQ ID NO:65)
WN-for           5'-CGAAGAAAACAATTATAATACG-3'             (SEQ ID NO:66)
WN-back          5'-CGTATTATAATTGTTTTCTTCG-3'             (SEQ ID NO:67)
FGF9_Stop-back 5'-AGCTGGATCCTCAACTTTGGCTTAGAATATCC-3'   (SEQ ID NO:68)
L37M-for         5'-ACGTGACCATATGGGTCAGTCCGAAGCAG-3'      (SEQ ID NO:69)
R64M-for         5'-GGGAATTCCATATGCAGCTATACTGCAGGACTG-3' (SEQ ID NO:70)
NS-for           5'-GTTCGAAGAAAGCTGGTATAATATACG-3'        (SEQ ID NO:71)
NS-back          5'-CGTATTATACCAGCTTTCTTCGAAC             (SEQ ID NO:72)
```

For example:

WG-for codes for the 5'to 3' sequence of the mutation Trp144 into Gly in FGF-9.

WG-back codes for the 3'to 5' sequence of the mutation Trp144 into Gly in FGF-9.

WR-for codes for the 5'to 3' sequence of the mutation Trp144 into Arg in FGF-9.

WR-back codes for the 3'to 5' sequence of the mutation Trp144 into Arg in FGF-9.

NS-for codes for the 5'to 3' sequence of the mutation Asn143 into Ser in FGF-9.

NS-for codes for the 3'to 5' sequence of the mutation Asn143 into Ser in FGF-9.

FGF9_Stop-back codes for the end of the FGF9 and incorporates a BamHI site.

For example, to produce L37M-W144G-FGF9 DNA, WG-for and FGF9_Stop-Back primers were used for the first PCR reaction. For the second PCR reaction WG-back and L37M-for were used. To produce L37M-W144R-FGF9 DNA, the WR-for and FGF9_Stop-back primers were used for the first reaction and WR-back and L37M-for primers for the second reaction.

The amplified DNA fragments were combined and served as the template for an additional PCR reaction, using L37M-for and FGF9_Stop-back as the L37M-FGF9 primers.

The PCR conditions were as follows: annealing temperature was 54° C. followed by elongation at 72° C. for 30 cycles. The purified PCR fragment was digested with NdeI and BamHI, and ligated into the p89BS construct.

To create the hisR64M-FGF9 variant the DNA resulting from the R64M-FGF9 reaction was cloned into an expression vector comprising the 6'his tag and thrombin cleavage site from the pET cloning vectors (Novagen).

Protein Purification

The newly constructed expression plasmids were transferred into TG-1 and plated on LB-agar plates supplemented with 200 ug/ml ampicillin and later grown in a two-liter flask containing 800 ml of TB 125 medium (Tryptone15 gr/L, Yeast extract 30 gr/L, $KH_2PO_4$ 2.31 gr/L, $K_2HPO_4$ 12.5 gr/L, Glycerol 5 gr/L) supplemented with 200 ug/ml ampicillin for 16 hr at 37° C. The bacterial suspension was centrifuged at 4000 rpm (4° C.) for 10 minutes, and the medium was removed. The bacterial pellet was then suspended in 30 ml of 1×PBS buffer containing protease inhibitors, sonicated on ice, and centrifuged at 15000 rpm (4° C.) for 10 minutes. The protein supernatant was collected, and 5 ml of heparin-Sepharose& beads slurry was added and shaken gently for 6 hours at 4° C. The beads were rescued by centrifugation (400 rpm at 4° C. for 10 minutes) washed extensively with PBS buffer containing 0.7M NaCl, and eluted in 2 ml PBS containing 2M NaCl. The FGF-9 variant proteins were then dialyzed against 1xPBS containing 5% glycerol and 1% CHAPS, and repurified on FPLC using a heparin Sepharose column (HiTrap™Heparin,Amersham Pharmacia biotech) with a 0-2M NaCl linear gradient in the same dialysis buffer. The purified proteins were later stored at −70° C.

EXAMPLE 2

Preparation of Truncated FGF Variants

The truncated mutants were prepared by PCR, where exemplary primers used are listed. Primers:

```
35421                                   (SEQ ID NO: 73)
5'-GGCCCTAGGTCATCTAGGTAAAAAATGTGTG-3'

35422                                   (SEQ ID NO:74)
5'-GGGAATTCCATATGCAGCTATACTGCAGGACTG-3'
```

-continued

```
29522                                   (SEQ ID NO:75)
5'-AGCTGGATCCTCAACTTTGGCTTAGAATATCC-3'

29690                                   (SEQ ID NO:76)
5'-GAGTGACCATATGGGTCAGTCGC-3'

35423                                   (SEQ ID NO:77)
5'-GGGAATTCCATATGCCCAGGGGACCCGCAGTCAC-3'

40869                                   (SEQ ID NO:78)
5'-CGATACGTACATATGCACTTAGAAATCTTC-3'

40870                                   (SEQ ID NO:79)
5'-GCAAGGATCCTCAATGTGTGAATTTCTG-3

42142                                   (SEQ ID NO:80)
5'-ACGATCGTACATATGTACTGCAGGACTGGA-3'
```

Where:

35421 codes for the 3'to 5' of P191-Stop with a BamHI restriction enzyme site for the construction of an FGF-9 variant.

35422 codes for the 5'to 3' of R64M with an NdeI restriction enzyme site for the construction of an FGF-9 variant.

29522 codes for the 3'to 5' of Stop codon at the end of FGF-9 with a BamHI restriction enzyme site for the construction of an FGF-9 variant.

29690 codes for the 5'to 3' of L37M and an NdeI restriction enzyme site for the construction of an FGF-9 variant.

35423 codes for the 5'to 3' of L45M with an NdeI restriction enzyme site for the construction of an FGF-9 variant;

40869 codes for the 5'to 3' of F72M and an NdeI restriction enzyme site for the construction of an FGF-9 variant;

40870 codes for the 3'to 5' of P189Stop with a BamHI restriction enzyme site for the for the construction of an FGF-9 variant;

42142 codes for the 5'to 3' of L66M with an NdeI restriction enzyme site for the construction of an FGF-9 variant.

For the PCR reaction of R64M-FGF9-DNA (SEQ ID NO: 18) we have used primers 35422 and 29522.

For the PCR reaction of FGF9-2 DNA (SEQ ID NO: 24) we have used primers 35422 and 35421.

For the PCR reaction of L37M-FGF9-DNA, L37M-W144X-FGF9 DNA and L37-N143X-FGF9 DNA (SEQ ID NO: 20, SEQ ID NO: 17 and SEQ ID NO: 16 respectively) we have used primers 29690 and 29522.

For the PCR reaction of L45M-FGF9 DNA (SEQ ID NO:19) we have used primers 35423 and 29522.

For the PCR reaction of F72M-P189Stop-F9 DNA (SEQ ID NO:25) we have used primers 40869 and 40870.

For the PCR reaction of F72M-P191Stop-F9 DNA (SEQ ID NO:26) we have used primers 40869 and 35421.

For the PCR reaction of R64M-P189Stop-F9 DNA (SEQ ID NO:27) we have used primers 35422 and 40870.

For the PCR reaction of L66M-P191Stop-F9-2 DNA (SEQ ID NO:28) we have used primers 42142 and 35421.

The new mutant PCR fragments were digested with restriction enzymes NdeI and BamHI and cloned in p89BS, forming DNA constructs; p89BS-variant FGF-9, which encode the FGF variants identified as SEQ ID NOS:14-28, The constructs were introduced into electrocompetent *E. coli* TG-1 cells.

EXAMPLE 3

FGF Variant Binding to FGFR-Transfected FDCP Cell Lines

The FDCP cell line is a murine immortalized, interleukin 3 (IL-3)-dependent cell line of myelocytic bone marrow origin that does not express endogenous FGF Receptors (FGFR). Upon transfection with FGFR cDNA, the FDCP cell line exhibits a dose-dependent proliferative response to FGF that can replace the dependence on IL-3. FGFR transfected FDCP cells can therefore be used to screen variant FGFs for specific inhibitors, activators or for FGFR signaling. FDCP cells response to various ligands is quantitated by a cell proliferation assay with XTT reagent (Cell Proliferation Kit, Biological Industries Co.). The method is based on the capability of mitochondrial enzymes to reduce tetrazolium salts into a colorogenic compound, which can be quantitated and is indicative of cell viability.

Specifically, FDCP cells stabily expressing FGFR3, FGFR3-IIIb isoform or FGFR1 were grown in "full medium" [Iscove's Medium containing 2 ml glutamine, 10% FCS, 100 ug/ml penicillin, 100 ug/ml streptomycin] supplemented with 5 ug/ml heparin and 10 ng/ml FGF-9. Cells are split every 3 days and kept in culture no more than one month. One day prior to the experiment the cells are split. Before the experiment the cells are washed 3 times (1000 rpm, 6 min) with full medium. The cells are resuspended and counted with Trypan Blue. Twenty thousand ($2\times10^4$) cells are added to each well of 96-well plate in 50 ul full medium containing heparin. Condition medium containing FGF-9 or variant at varying concentrations was added in an additional volume of 50 ul full medium to bring the final volume to 100 ul. The plate was incubated for 48 hours at 37° C. To test cell proliferation, 100 ul of PMS reagent was added to 5 ml of XTT reagent and mixed well (according to manufacture protocol). 50 ul of the latter solution were aliquoted into each well, and the plates incubated at 37° C. for 4 hours and the color developed was read by a spectro-ELISA reader at $A_{490\ nm}$.

In this experiment FDCP cells expressing FGFR3 or FGFR1 were grown in the presence of varying concentrations of the FGF-9 variants.

Results

Table 2 in the specifications shows the specificity of the FGF variants to FDCP cells transfected with FGFR1 or FGFR3. FIGS. 3-7 depict the mitogenicity level and receptor specificity of a sample of the variants of the invention. Native FGF-9 is presented as control in all the assays.

FGF-9, L37M-FGF9 and L37M-W144G-FGF9 were tested for their ability to induce cell proliferation of FDCP cells expressing FGFR1, FGFR3 and FGFR3-IIIb isoform. FGF-9 and L37M-FGF9 induced proliferation of both FDCP-FGFR3 and FDCP-FGFR1, with comparable affinities. L37M-W144G-FGF9, on the other hand, induced proliferation of FDCP-FGFR3 as well as wild-type FGF-9, but no proliferation was observed on FDCP-FGFR1. Even a 100-fold higher concentration of the latter variant resulted in only a very low inducible proliferation. Furthermore, induction of proliferation by on FDCP cells expressing the FGFR3-IIIb isoform was more than twice the level of that induced by L37M-W144G-FGF9.

The L37M-W144R-FGF9 variant, in which the Trp144 is substituted with an arginine, induced proliferation on FDCP-FGFR3 at a 5-fold lower level than FGF-9, but had no apparent mitogenic activity on FDCP-FGFR1, and very low activity on FDCP-FGFR3-IIIb.

EXAMPLE 4

ERK ELISA Assay of FGF Variants

FGF/FGFR-dependent ERK activation signal transduction is measured in an ELISA assay using monoclonal anti-diphosphorylated ERK antibodies. The assay is followed by reading $A_{450\ nm}$ after addition of the TMB reagent to monitor the total ERK activation.

In summary, RCJ WT11/M14/R1/R2 cells, over-expressing FGFR, are grown in α-MEM$^{++}$ medium (15% FCS, G-418 600 μg/ml, tetracycline 2-3 μg/ml). The concentration of cells seeded ranges between $7.5\times10^4$ and $6\times10^5$ cells/well. The cell medium is removed 14-16 hrs prior to beginning of experiment. Four to 5 hours before addition of the FGF-9 or variants, the cells are serum starved. Either wild type or variant FGF-9 are added at a concentration range of 0.1-100 ng/ml for 6-7 minutes at 37° C. FGF stimulation is stopped by cooling the cells on ice followed by washing 3 times with cold PBS. The cells are lysed by addition of lysis buffer (1 mM EGTA, 1 mM EDTA, 25 mM Tris/50 mM Hepes, 25 mM NaF, 50 mM. β-glycerophosphate, 50 mM NaCl, 10% Glycerol, 1% NP40, pH 7.5, freshly prepared Orthovanadate to 2 mM, and Protease Inhibitors) for 10 minutes on ice. The cell lysates are collected and spun for 10 minutes at 15,000 rpm. SDS is added to the supernatants to 1.5% final concentration and the mixture incubated for 15 min at room temp. Following protein determination, the protein and SDS concentrations are adjusted with lysis buffer to a final concentration of 7 μg protein and 0.15% SDS in 100 μl. 100 μl of sample lysate is added to a Maxisorp 96 well plate (Nunc immuno-plate 430341) precoated with monoclonal anti-diphosphorylated MAPK/ERK (Sigma M8159) diluted to 1:3000 with a mixture 4% BSA in TBST and lysis buffer adjusted to 0.15% SDS. The plates are incubated, shaking, for 2 hrs at room temp. The wells are washed and each well incubated with 100 μl of 1:10,000 dilution of HRP-conjugated goat anti-mouse IgG (Jackson Immunoresearch 800-367-5296) in 2% BSA/TBST for 1-1.5 hrs at room temp, with shaking. Following incubation, the samples are washed 5-6 times with TBST, and 100 μl of developing medium (1:1 mixtures A and B of ImmunoPure TMB substrate kit) is added for 10 minutes at room temperature. The reaction is stopped by the addition of $H_2SO_4$ and the absorbance was read at 450 nm.

EXAMPLE 5

Effect of Variants on Growth Arrest of RCS Chondrocytes

RCS is a rat chondrosarcoma derived cell line expressing preferentially high levels of FGFR2 and FGFR3 and low levels of FGFR1. In this cell line FGFR functions as an inhibitor of cell proliferation similar to its expected role in the Achondroplasia phenotype. Analysis of RCS cell proliferation mediated by the addition of different FGFs, showed inhibition by aFGF, bFGF and FGF-9. The advantages in using this cell line for screening of FGF compounds is that in order to inhibit cell proliferation the compounds have to be (1) non-toxic, (2) specific to FGF induced signal transduction and (3) potent. Therefore, one can extrapolate FGF affinity and specificity to the FGFRs by the concentration dependence of induced growth arrest. The screening was performed on RCS parental cells in 96 wells plates. Cells were seeded at a concentration of 2,000 cells/well. The following day 10 ng/ml FGF-9 or variants and 5 μg/ml heparin were added to the cells. Positive and negative controls for cell proliferation are included in this assay at the same concentrations as the tested compounds. On the fourth day of incubation, plates were observed under the microscope. If all cells were viable, no quantitative assay to measure the effect of the variants was performed. If cell death was observed, the Cy-Quant assay kit is used to measure the amount of the cells. The results are measured in a fluoro ELISA reader.

Results

Figure 12:
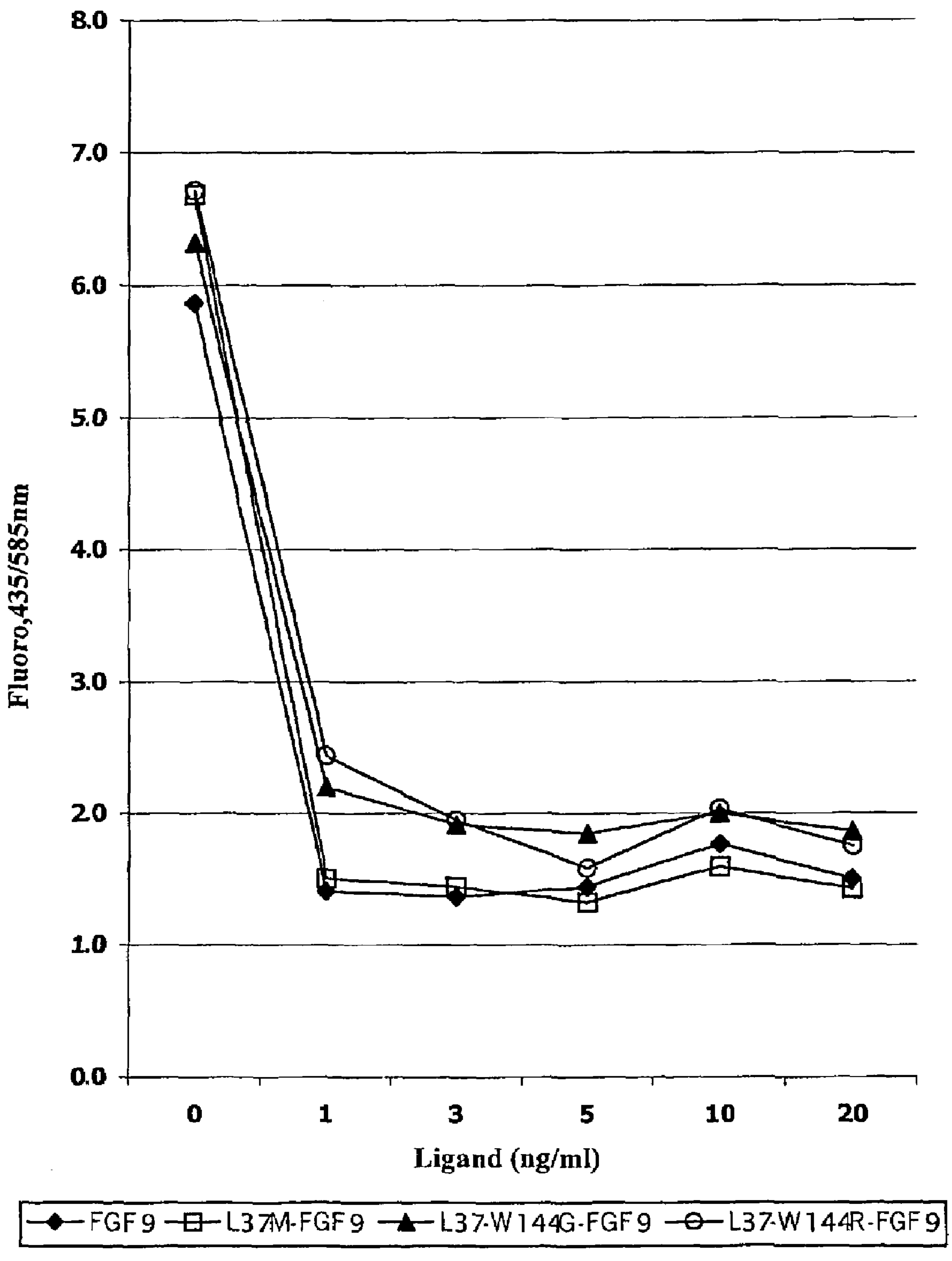
FIG. 12 illustrates the dose response of the FGF variants, L37M-FGF9, L37M-W144G-FGF9 and L37M-W144R-FGF9 as a measurement of growth arrest in RCS cells.

Similar levels of growth arrest are observed when RCS cells are exposed to FGF-9 or the variants L37M-FGF9, L37M-W144G-FGF9 or L37M-W144R-FGF9. FIG. 12 depicts the dose curve for a sample of the variants compared to FGF-9, which serves as a control.

EXAMPLE 6

Jnk Activation by FGF Variants

JNK activation by wildtype and variant FGF-9 proteins was determined in an in vitro cell assay using stably transfected RCJ (Rat calvaria) cell lines expressing either the FGFR1IIIC, 2IIIC or 3IIIC isoforms. Activation is viewed in a standard Western assay using Rabbit anti-active JNK antibodies (Promega). In each lane, cell lysate of RCS cells exposed to 0, 12.5, 25, 50 or 100 ng of FGF-9 or variant was loaded. The filters were probed with antibodies to FGFR1, FGFR2, FGFR3 or activated JNK.

Results

FIG. 8 depicts the results of the Western assay. Firstly, the upper row shows that the RCS cells express low levels of FGFR1, moderate levels of FGFR2 and very high levels of FGFR3, as detected by receptor-specific antibodies. FGF-9 and L37M-FGF9 induced JNK activation through all three receptors at concentrations as low as 12.5 ng/ml. L37M-W144G-FGF9 and L37M-W144R-FGF9 retained their ability to activate JNK through FGFR2 and FGFR3, but a significant reduction in the JNK activation level through FGFR1 was seen.

EXAMPLE 7

Effects of FGF Variants on Femoral Growth

Femoral bone cultures were performed by excising the hind limbs of wild type mice. The limbs were carefully cleaned from the surrounding tissue (skin and muscles) and the femora exposed. The femora were removed and further cleared from tissue remains and ligaments. The femora were measured for their initial length, using a binocular with an eyepiece micrometer ruler. The bones were grown in 1 ml of medium with FGF-9 or FGF-9 variants in a 24 well tissue culture dish. The growing medium is a-MEM supplemented with penicillin (100 units/ml), streptomycin (0.1 mg/ml) and nystatin (12.5 units/ml). In addition, the medium contains BSA (0.2%), β-glycerophosphate (1 mM) and freshly prepared ascorbic acid (50 μg/ml). The bones were cultured for 15 days. Measurements of bone length and medium replacement were performed every three days.

At the end of the experiment, the growth rate of the bones was determined. The growth rate of bones is calculated from the slope of a linear regression fit on the length measurements obtained from day 3 to 12. Units given can be converted to length, 40 units=1 mm.

Results

FIG. 10 depicts the growth inhibition induced by the L37M-FGF9 and L37M-W144G-FGF9 variants. The triangle ▲ depicts the effect of a truncated variant L37M-FGF-9, while the square ■ and solid ▼ show the level of growth inhibition of L37M-W144G-FGF-9 at two concentrations.

EXAMPLE 8

Effects of FGF Variants on Femoral Growth-Neutralizing Activity of the MSPRO-59 Antibody An FGFR3 specific neutralizing antibody, MSPRO-59 identified in phage display library, was used to determine the receptor specificity of the L37M-W144G-FGF9 variant. FGF-9 binds to both the FGFR1 and FGFR3 receptors, expressed in the growth plate of embryonic bones, and has the capacity to inhibit growth of wild type mouse femoras, ex vivo. The experiment is set up as in Example 7 except for the following changes. The FGFR3 neutralizing antibody (59), at a concentration of 100 μg/ml, or a non-relevant antibody anti-lysosyme (Ly) was added with FGF-9 or the L37M-W144G-FGF9 variant to femoras in an ex vivo culture.

Results

FIG. 11 shows that growth inhibition of FGF-9 is not affected by the addition of a neutralizing antibody, suggesting that this effect is dependent on activation of FGFR1, in addition to FGFR3. Conversely, no growth inhibition and even a slight growth stimulation is detected when the neutralizing antibody is incubated with the L37M-W144G-FGF9 variant, suggesting that the variant can no longer bind to and activate the FGFR1 and preferentially binds to and activates FGFR3. The control antibody, anti-lysosyme had no effect. Table 3 depicts the results of this experiment.

TABLE 3

| | Growth inhibition |
|---|---|
| FGF-9 | + |
| FGF-9 + MSPRO-59 | + |
| L37M-W144G-FGF9 | + |
| L37M-W144G-FGF9 + MSPRO-59 | − |

EXAMPLE 9

Effect of FGF-9 Variants in Bone Fracture Healing

Ulnas were fractured in New Zealand Rabbits in compliance with the Animal Care Committee of the Hebrew University. The ulna was chosen because it is only slightly weight-bearing and allows the creation of a bone defect without requiring a cast or other immobilization treatment. In addition, this gap constitutes a spontaneously healing defect that allows the evaluation of the tested agent. The primary indices of fracture healing are accelerated duration of healing and callus formation. The tested compounds consisted of FGF-9 or FGF-9 variant in a polymeric scaffold (hyaluronic acid, HA), which facilitates bone growth.

The treatments groups consisted of:

Osteotomy without treatment.

Osteotomy treated with 0.2 ml of HA alone.

Osteotomy treated with 0.2 ml HA containing 20 μg FGF-9.

Osteotomy treated with 0.2 ml HA containing 20 μg FGF-9 variant

A 0.6 cm radial gap osteotomy was created under anesthesia with rotary saw in both ulnas of each animal. About 1 ml of HA or HA containing the tested compounds was administrated by injection into the gap. The periosteum, which was not resected during the surgery, was used to close the gap. Fracture healing was radiologically evaluated every week up to 4 weeks p.o. (post osteotomy). An X-ray closure of both limbs in a lateral position was taken. X-ray films were examined by a Film Digitizer, and the following parameters were measured: Total area of regenerated bone appearing around and within the bone gap defect (callus area) and the relative density of the newly regenerated bone in the gap defect. Histopathlogical evaluation was made by preparing thin sections that were stained with hematoxylin and eosin for cytoplasm and nucleus. Indigo-Carmin staining was also applied for detection of new generated callus.

Results

FIG. 9A shows autoradiograph analysis of ulnas in the various treatment groups, performed 4 weeks post surgery. As can be observed, the bone union was a time dependent process and the course of fracture healing was dependent upon the given treatment. Callus formation was detected as early as one week post osteotomy in fracture treated with the FGF-9 variant, L37M-W144G-FGF9. This process was enhanced during the second week. In control animals callus formation was barely detected in at the same time intervals.

Histological specimens of bone treated with the various samples were prepared. Also, quantitative bone mineral content measurements by DEXA (Dual X-ray Absorptiometry) were performed at the defect site for the various treatments at 4 weeks post osteotomy (FIG. 9B).

The data indicate that a single local injection of 20 μg L37M-W144G-FGF9 in combination with HA as a scaffold promotes healing of the bone defect by stimulating callus formation. It can be speculated from this data that the effect of the treatments occurs relatively early in the healing process, e.g., about 1-2 weeks earlier when compared to the control treatment. It should be noted that the most common biological failure in fracture healing involves an improperly formed callus within the first weeks after the fracture. Therefore, the earlier stimulation of callus in addition to its larger amount formation in L37M-W144G-FGF9 treatments might resolve the problem of biologic failure associated with inadequate callus formation.

EXAMPLE 10

Binding Assay of FGF Variants

Binding of FGF proteins to different FGF receptors are determined by measuring the degree of competition for binding to different types of FGFR proteins between a radioiodinated FGF protein and various unlabelled proteins, or by the direct binding of radioiodinated FGF's to various receptor proteins. Binding studies are confirmed by chemical cross-linking of the radioiodinated FGF to soluble receptors in the presence and absence of excess unlabelled FGF.

Sodium heparin from porcine intestinal mucosa (PM-heparin) is obtained from Hepar Industries (Franklin, Ohio). KGF is obtained from UBI (Lake Placid, N.Y.). $^{125}I$ is purchased from Amersham (Buckinghamshire, England). FGFs are iodinated using chloramine T. Saline contains 0.05% trypsin, 0.01M sodium phosphate, and 0.02% EDTA (STV). Tissue culture dishes are from Falcon Labware Division, Becton Dickinson (Oxnard, Calif.). Four-well tissue culture plates are from Nunc (Rosklide, Denmark).

Soluble FGF receptor proteins are constructed by cloning of the extracellular region of murine FGF receptor 1 (FGFR-1; flg), FGF receptor 2 (FGFR-2; bek) or the KGF receptor (FGFR(IIIb); K-sam) into the alkaline phosphatase-tag expression vector, which encodes for a secreted form of placental alkaline phosphatase (AP). The FGF receptor alkaline phosphatase (FRAP) plasmids are cotransfected into NIH 3T3 cells by electroporation with a selectable neomycin resistance gene. Clonies are selected in G418 (600 .mu.g/ml) and screened for secreted AP enzyme activity in the conditioned medium. Clones of each receptor which produced a high level of AP activity (2 to 4 A.sub.405 units/min/ml) are then used to produce conditioned medium for binding assays.

Components of the soluble receptor binding reaction mixture include FRAP-conditioned medium (0.24 OD units/min), 2 ng/ml $^{125}$I-FGFs and 200 ng/ml heparin. The FGF:heparin:FRAP terniary complex is immunoprecipitated with 20 μl of a 1:1 slurry of anti-AP monoclonal antibodies coupled to protein A Sepharose.RTM. All components are mixed at room temperature. The total volume is adjusted to 200 μl by addition of DMEM containing 0.1% bovine serum albumin. Binding is allowed to proceed for 1 to 2 hours at 24° C., after which time bound receptor complex or the ligand is recovered by centrifugation at 4° C. (10 s at 2,000× g). The pelleted material is washed twice with 500 μl of an ice cold buffer containing HEPES (20 mM), NaCl (150 mM), glycerol (10%) and Triton®X-100 (1%). $^{125}$I-FGF binding is quantitated by counting of the samples in a gamma counter. Alternatively, AP enzyme activity of the FRAP protein is determined by transferring the FRAP receptor bound to heparin-Sepharose® to a flat-bottom microtiter plate in a volume of 50 μl of PBS. The reaction is initiated by addition of substrate (50 μl of 2× solution of AP assay buffer containing 2M diethanoiamine, 1 mM $MgCl_2$, 20 mM homoarginine and 12 mM p-nitrophenyl phosphate). The reaction is followed at room temperature at 405 nm in a kinetic microplate reader.

Receptor binding is determined by quantitating release of labelled FGF from receptors. Briefly, FGF bound to heparan sulfate low affinity sites is released from the cell surface by a 5 minute incubation with an ice cold solution containing 1.6M Nacl, 20 mM HEPES, pH 7.4, and the amount of radioactivity release determined in a gamma-counter. FGF bound to high affinity receptors is dissociated by a 2M NaCl (20 mM acetate buffer, pH 4.0) extraction, and the released labelled FGF is quantitated. Chemical cross-linking experiments are carried out at room temperature in a volume of 20 μl in siliconized 0.5-ml microcentrifuge tubes. The reaction mixtures contain FGF receptor immobilized to anti-AP monoclonal antibodies coupled to protein A Sepharose, 200 ng/ml heparin, 2 ng/ml $^{125}$I-FGF, 20 mM phosphate buffer (pH 7.4), and 140 mM NaCl. After a 90 minute incubation, 1 ml of a solution of disuccinimidyl suberate (Pierce) dissolved in dimethyl sulfoxide is added to give a final concentration of 0.15 mM, and the mixture incubated for an additional 30 minutes. The reaction is quenched by addition of 1 ml of 200 mM ethanolamine-HCl (pH 8.0) for 30 min. The reaction mixtures are diluted 1:1 with 2× SDS-polyacrylamide gel electrophoresis loading buffer and electrophoresed on an SDS-12% polyacrylamide gel. Cross-linked FGF to the FGF receptor are detected by autoradiography on Kodak XAR film.

While the present invention has been particularly described, persons skilled in the art will appreciate that many variations and modifications can be made. Therefore, the invention is not to be construed as restricted to the particularly described embodiments, rather the scope, spirit and concept of the invention will be more readily understood by reference to the claims which follow.

What is claimed is:

1. An active FGF-9 variant having at least one mutation in the beta 8 beta 9 loop of the core structure, wherein said FGF-9 variant has enhanced specificity for one receptor subtype compared to the corresponding wild type FGF-9, by decreasing the biological activity mediated by at least one receptor subtype while retaining the activity mediated through another receptor subtype wherein at least one substitution is replacement of tryptophan at position 144 of FGF-9 or asparagine at position 143 of FGF-9.

2. The active FGF-9 variant of claim 1 wherein the FGF-9 variant is selected from the group consisting of a human FGF-9 variant, mouse FGF-9 variant and chicken FGF-9 variant.

3. The active FGF-9 variant of claim 1 having the amino acid sequence of SEQ ID NO: 1 wherein at least one substitution is replacement of tryptophan at position 144.

4. The active FGF-9 variant of claim 3 wherein the tryptophan at position 144 is replaced by an amino acid selected from the group consisting of glycine, arginine, valine, serine and glutamate.

5. The active FGF-9 variant of claim 1 having the amino acid sequence of SEQ ID NO: 3 wherein at least one substitution is replacement of asparagine at position 143.

6. The active FGF-9 variant of claim 5 wherein the asparagine at position 143 is replaced by serine.

7. The active FGF-9 variant of claim 1 having fewer than 30 amino acid residues at the N-terminus or fewer than 15 residues at the C terminus extending beyond the core structure.

8. The active FGF-9 variant of claim 7 having the amino acid sequence of SEQ ID NO: 2.

9. The active FGF-9 variant of claim 8 wherein the tryptophan at position 144 is replaced by an amino acid selected from the group consisting of arginine, glycine, valine, serine and glutamate.

10. The active FGF-9 variant of claim 7 having the amino acid sequence of SEQ ID NO: 4.

11. The active FGF-9 variant of claim 10 wherein the asparagine at position 143 is replaced by a serine.

12. A polynucleotide molecule encoding an active FGF-9 variant according to claim 1.

13. The polynucleotide molecule of claim 12 having the nucleic acid sequence of SEQ ID NO: 14 or SEQ ID NO: 16.

14. The polynucleotide molecule of claim 12 wherein the variant having fewer than 30 amino acid residues at the N-terminus or fewer than 15 residues at the C terminus extending beyond the core structure.

15. The polynucleotide molecule of claim 14 having the nucleic acid sequence of SEQ ID NO: 15 or SEQ ID NO: 17.

16. The polynucleotide molecule of claim 12 having the nucleic acid sequence selected from the group consisting of SEQ ID NO: 18, SEQ ID NO: 19, SEQ ID NO: 20, and SEQ ID NO: 21.

17. A vector comprising a polynucleotide molecule according to claim 12.

18. A pharmaceutical composition comprising as an active ingredient an active FGF-9 variant according to claim 1.

19. An active FGF-9 variant wherein said variant is selected from the polypeptides having the amino acid sequence of SEQ ID NO:5, SEQ ID NO: 6 or SEQ ID NO: 7.

20. The active FGF-9 variant of claim 19 wherein said variant includes heterologous sequences at the N-terminus or C-terminus.

21. The active FGF-9 variant of claim 20 having the amino acid sequence of SEQ ID NO: 8.

22. A pharmaceutical composition comprising as an active ingredient an active FGF-9 variant according to claim 19.

* * * * *